(12) United States Patent
Heusser et al.

(10) Patent No.: US 9,688,768 B2
(45) Date of Patent: *Jun. 27, 2017

(54) SILENT FC VARIANTS OF ANTI-CD40 ANTIBODIES

(71) Applicants: Christoph Heusser, Oberwil (CH); James Rush, Thalwil (CH); Karen Vincent, Leymen (FR)

(72) Inventors: Christoph Heusser, Oberwil (CH); James Rush, Thalwil (CH); Karen Vincent, Leymen (FR)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/946,170

(22) Filed: Nov. 19, 2015

(65) Prior Publication Data

US 2016/0152721 A1 Jun. 2, 2016

Related U.S. Application Data

(63) Continuation of application No. 14/452,647, filed on Aug. 6, 2014, now Pat. No. 9,221,913, which is a continuation of application No. 13/295,141, filed on Nov. 14, 2011, now Pat. No. 8,828,396.

(60) Provisional application No. 61/413,567, filed on Nov. 15, 2010.

(51) Int. Cl.
*A61K 39/395* (2006.01)
*C07K 16/28* (2006.01)
*A61K 39/00* (2006.01)

(52) U.S. Cl.
CPC ...... *C07K 16/2878* (2013.01); *C07K 16/2866* (2013.01); *A61K 2039/505* (2013.01); *C07K 2317/52* (2013.01); *C07K 2317/565* (2013.01); *C07K 2317/60* (2013.01); *C07K 2317/71* (2013.01)

(58) Field of Classification Search
None
See application file for complete search history.

(56) References Cited

U.S. PATENT DOCUMENTS

| | | | |
|---|---|---|---|
| 5,397,703 A | 3/1995 | de Boer et al. | |
| 5,677,165 A | 10/1997 | de Boer et al. | |
| 5,801,227 A | 9/1998 | Fanslow, III et al. | |
| 5,874,082 A | 2/1999 | de Boer et al. | |
| 6,004,552 A | 12/1999 | de Boer et al. | |
| 6,056,959 A | 5/2000 | de Boer et al. | |
| 6,315,998 B1 | 11/2001 | de Boer et al. | |
| 6,899,879 B2 | 5/2005 | de Boer et al. | |
| 6,923,956 B1 | 8/2005 | Tschope et al. | |
| 7,063,845 B2 | 6/2006 | Mikayama et al. | |
| 7,193,064 B2 | 3/2007 | Mikayama et al. | |
| 7,537,763 B2 | 5/2009 | Mikayama et al. | |
| 7,790,166 B2 | 9/2010 | de Boer et al. | |
| 8,217,149 B2 | 7/2012 | Irving et al. | |
| 8,277,810 B2 | 10/2012 | Long et al. | |
| 8,333,970 B2 | 12/2012 | Aukerman et al. | |
| 8,637,032 B2 | 1/2014 | Long et al. | |
| 8,828,396 B2 | 9/2014 | Heusser et al. | |
| 9,221,913 B2 * | 12/2015 | Heusser | C07K 16/2878 |
| 2003/0211100 A1 | 11/2003 | Bedian et al. | |
| 2004/0110226 A1 | 6/2004 | Lazar et al. | |
| 2005/0053598 A1 | 3/2005 | Burke et al. | |
| 2007/0098717 A1 | 5/2007 | Long et al. | |
| 2007/0098718 A1 | 5/2007 | Long et al. | |
| 2007/0110754 A1 | 5/2007 | Long et al. | |
| 2007/0148163 A1 | 6/2007 | Takahashi et al. | |
| 2007/0218060 A1 | 9/2007 | Long et al. | |
| 2008/0057070 A1 | 3/2008 | Long et al. | |
| 2008/0175847 A1 | 7/2008 | Yan et al. | |
| 2008/0199471 A1 | 8/2008 | Bernett et al. | |
| 2008/0254026 A1 | 10/2008 | Long et al. | |
| 2009/0053230 A1 | 2/2009 | Martin | |
| 2009/0202531 A1 | 8/2009 | Aukerman et al. | |
| 2009/0204489 A1 | 8/2009 | Behrens et al. | |
| 2009/0304706 A1 | 12/2009 | Lu et al. | |
| 2010/0158914 A1 | 6/2010 | Desnoyers | |
| 2012/0087927 A1 | 4/2012 | Matsushima et al. | |
| 2014/0004131 A1 | 1/2014 | Mueller et al. | |
| 2014/0341898 A1 | 11/2014 | Heusser et al. | |

FOREIGN PATENT DOCUMENTS

| | | |
|---|---|---|
| CA | 2 759 146 A1 | 10/2010 |
| EP | 1 391 464 A1 | 2/2004 |
| EP | 1 707 627 A1 | 4/2006 |
| EP | 1 914 243 A2 | 4/2008 |
| WO | 94/01547 A3 | 1/1994 |
| WO | 95/17202 A1 | 6/1995 |
| WO | 96/18413 A1 | 6/1996 |
| WO | 97/04801 A1 | 2/1997 |

(Continued)

OTHER PUBLICATIONS

Amit et al., Three-dimensional structure of an antigen-antibody complex at 2.8 A resolution. Science. Aug. 15, 1986;233(4765):747-53.

Balint, R., et al., "Antibody Engineering by Parsimonious Mutagenesis," Gene, 1993, pp. 109-118, vol. 137, No. 27.

Benoit et al., "Increased Inhibition of proliferation of human B cell lymphomas following litigation of CD40, and either CD19, CD20, CD95 or surface immunoglobulin," Immunopharmacology, 1996, vol. 35, pp. 129-139.

Boon, L., et al., "Prevention of Experimental Autoimmune Encephalomyelitis in the Common Marmoset (*Callithrix jacchus*) Using a Chimeric Antagonist Monoclonal Antibody Against Human CD40 Is Associated with Altered B Cell Responses," Journal of Immunology, 2001, pp. 2942-2949, vol. 167, No. 5.

(Continued)

*Primary Examiner* — Phillip Gambel

(57) ABSTRACT

The present invention relates to silent Fc variants of anti-CD40 antibodies and compositions and methods of use of said antibodies for treating pathological disorders such as autoimmune and inflammatory disorders and/or for preventing or reducing the risk of graft rejection in transplantation.

10 Claims, 5 Drawing Sheets

(56) References Cited

FOREIGN PATENT DOCUMENTS

| WO | 97/31025 A1 | 8/1997 |
|---|---|---|
| WO | 99/42075 A2 | 8/1999 |
| WO | 01/34649 A3 | 5/2001 |
| WO | 01/83755 A3 | 11/2001 |
| WO | 02/04021 A1 | 1/2002 |
| WO | 02/22212 A2 | 3/2002 |
| WO | 02/28480 A2 | 4/2002 |
| WO | 02/28481 A2 | 4/2002 |
| WO | 02/28904 A3 | 4/2002 |
| WO | 02/28905 A2 | 4/2002 |
| WO | 02/060485 A2 | 8/2002 |
| WO | 02/078766 A2 | 10/2002 |
| WO | 02/088186 A1 | 11/2002 |
| WO | 03/029296 A1 | 4/2003 |
| WO | 03/040170 A1 | 5/2003 |
| WO | 03/045978 A3 | 6/2003 |
| WO | 2005/044294 A2 | 5/2005 |
| WO | 2005/044304 A2 | 5/2005 |
| WO | 2005/044305 A2 | 5/2005 |
| WO | 2005/044306 A2 | 5/2005 |
| WO | 2005/044307 A2 | 5/2005 |
| WO | 2005/044854 A2 | 5/2005 |
| WO | 2005/044855 A2 | 5/2005 |
| WO | 2006/073443 A2 | 7/2006 |
| WO | 2007/124299 A2 | 11/2007 |
| WO | 2007129895 A2 | 11/2007 |
| WO | 2008/150494 A1 | 12/2008 |

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-2794.

Colman, Effects of amino acid sequence changes on antibody-antigen interactions. Res Immunol. Jan. 1994;145(1):33-36.

Ellmark, P., et al. "Modulation of the CD40-CD40 Ligand Interaction Using Human Anti-CD40 Single-Chain Antibody Fragments Obtained from the n-CoDeR Phage Display Library," Immunology, 2002, pp. 456-463 vol. 106, No. 4.

Funakoshi, S., et al., Differential in Vitro and in Vitro Antitumor Effects Mediated by Anti-CD40 and AntiCD20 Monoclonal Antibodies Against Human B-Cell Lymphomas, Journal of Immunotherapy, 1996, vol. 19, No. 2 pp. 93-101.

Gisselbrecht, C., et al., "Interleukin-2 Treatment in Lymphoma: A Phase II Multicenter Study," Blood, 1994, pp. 2081-2085, vol. 83, No. 8.

Hager A-C Malmborg, et al. :Affinity and Epitope Profiling of Mouse Anti-CD40 Monoclonal Antibodies, Scandinavian Journal of Immunology, 2003, pp. 517-524, vol. 57, No. 6.

Horton et al., "Fc-engineered anti-CD40 antibody enhances multiple effector functions and exhibits potent in vitro and in vivo antitumor activity against hematologic malignancies," Blood 116(16):3004-3012 (2010).

Kussie et al., A single engineered amino acid substitution changes antibody fine specificity. J Immunol. Jan. 1, 1994;152(1):146-152.

Li et al., "Promises and Obstacles for the Blockade of CD40-CD40L Interactions in Allotransplantation," Transplantation 86( 1) : 10-15 (2008).

Little, M., et al., "Of Mice and Men: Hybridoma and Recombinant Antibodies," Immunology Today, 2000, pp. 364-370, vol. 21.

Little., et al., "Of Mice and Men: Hybridoma and Recombinant Antibodies," Immunology Today, 2000, pp. 364-370, vol. 21.

Maloney, D.G., et al., "IDEC-C2B8: Results of a Phase I Multiple-Dose Trial in Patients with Relapsed Non-Hodgkin's Lymphoma," Journal of Clinical Oncology, 1997, vol. 15, No. 10, pp. 3266-3274.

Presta, Leonard, "Engineering of therapeutic antiodies to minimize immunogenicity and optimize function," Advanced Drug Delivery Reviews 58(5-6):640-656 (2006).

Rosenberg, S.A., et al., "A Progress Report on the Treatment of 157 Patients with Advanced Cancer Using Lymphokine-Activated Killer Cells and Interleukin-2 or High-Dose Interleukin-2 Alone," the New England Journal of Medicine, 1987, pp. 889-897, vol. 316, No. 15.

Rudikoff et al. Proc Natl Acad Sci USA 79: 1979-1983 (1982).

Siberil et al., "FcR: The key to optimize therapeutic antibodies?" Critical Reviews in Oncology/Hematology 62(1):26-33 (2007).

Singh et al., The Role of Polar Interactions in the Molecular Recognition of CD40L with its Receptor CD40, Protein Science, 1998, pp. 1124-1135, vol. 7.

Strohl, Optimization of Fc-mediated effector functions of monoclonal antibodies. Curr Opin Biotechnol. Dec. 2009;20(6):685-91. Epub Nov. 4, 2009.

Tai, Y., et al., "Mechanisms by which SGN-40, a Humanized Anti-CD40 Antibody, Induces Cytotoxicity in Human Multiple Myeloma Cells: Clinical Implications," Cancer Research, 2004, pp. 2846-2852, vol. 64, No. 8.

Vajdos et al., Comprehensive functional maps of the antigen-binding site of an anti-ErbB2 antibody obtained with shotgun scanning mutagenesis. J Mol Biol. Jul. 5, 2002;320(2):415-28.

Weng Wen-Kai, et al., "Human anti-CD40 Antagonistic Antibodies Inhibit the Proliferation of Human B Cell Non-Hodgkin's Lymphoma", Blood 2001, p. 466a, vol. 98, No. 11, Part 1, Abstract #1947.

* cited by examiner

SILENT FC VARIANTS OF ANTI-CD40 ANTIBODIES

This application is a continuation and claims benefit under 35 U.S.C. §120 of U.S. application Ser. No. 14/452,647, filed Aug. 6, 2014, which is a continuation and claims the benefit under 35 U.S.C. §120 of U.S. application Ser. No. 13/295,141, filed Nov. 14, 2011, which claims benefit under 35 U.S.C. §119(e) of U.S. Provisional Application No. 61/413,567, filed Nov. 15, 2010, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Aug. 4, 2014, is named PAT054423-US-CON_Seq_Listing.txt and is 46,823 bytes in size.

The present invention relates to silent constant fragment (Fc) variants of anti-CD40 antibodies and compositions and methods of use of said antibodies for treating pathological disorders such as autoimmune and inflammatory disorders and/or for preventing or reducing the risk of graft rejection in transplantation.

Despite availability of several immunosuppressive treatments for autoimmune diseases, there remains a large unmet need for more efficacious and safer drugs in a large fraction of the patient population. For example, despite the reported efficacy of B cell depleting/inhibiting therapies like Rituximab and Belimumab in rheumatoid arthritis, systemic lupus erythematosus, Sjögren's syndrome, and multiple sclerosis, these therapies are only effective in a portion of diseased individuals, and, with Rituximab, with an accompanying risk of progressive multifocal leukoencephalopathy. Further, multiple other leukocyte cell types are often involved in the pathology of these autoimmune diseases such as macrophages, dendritic cells and T cells, therefore therapeutic intervention targeting additional cell types or key immunological pathways that would inhibit their function could provide benefit. Given the multiple immunologically relevant roles of CD40-CD154 in the activation and function or these cell types, it is likely that an anti-CD40 antibody would confer therapeutic benefit to patients suffering autoimmune diseases outlined above beyond that currently provided by current therapies. Further, the central role for CD40-CD154 interactions in intestinal inflammatory disorders such as Crohn's disease and ulcerative colitis, and mechanistic links of the CD40 pathway to pathology in more rare disorders such as autoimmune vasculitis, pemphigus vulgaris, and ITP also highlights the potential of anti-CD40 antibodies in these indications.

The currently available immunosuppressants used after solid organ transplantation provide excellent short-term efficacy. Acute rejections within the de novo period are observed in 5%-20% of the recipients (depending on organ, patient population, and regimen) and the proportion of grafts lost to acute rejection within the de novo period is below 5% for any setting. Currently the key unmet need is the tolerability of immunosuppression with patient and graft survival in the long term. After renal transplant, 33% patients die and/or lose their graft within 5 years; the average age of death of transplant recipient is 58 years. Calcineurin inhibitors (CNI) remain the mainstay of immunosuppressive therapy for the vast majority of transplant patients. While nephrotoxicity and cardiovascular morbidity associated with CNIs is one of the drivers of chronic allograft nephropathy as well as patient death with a functioning graft, alternative primary immunosuppression have not been able to replace CNIs. Overall, there is still room for improvement in long-term transplant immunosuppression. B-cell mediated immunological damage of transplanted kidneys may contribute to poor long-term outcomes and the need for new agents to target B-cell rejection is increasingly recognized by the medical community.

Chir12.12 is a fully humanized, non-agonist anti-CD40 antibody (IgG1, kappa) that blocks CD154 (also known as CD40 ligand; CD40L)-mediated leukocyte activation and can mediate antibody-dependent cellular cytotoxicity (ADCC) of human leukocytes and B cell lymphomas in vitro (see WO2006/073443). WO2005/044306 also describes anti-CD40 antagonist antibodies, including Chir12.12 for use in particular in the treatment of autoimmune and inflammatory disorders. Further Chir12.12 is effective in delaying kidney allograft rejection when dosed as a monotherapy in *Macaca fascicularis* (Cynomolgus monkeys) [Li et al. (2008) Transplantation; 86 (1):10-15]. However, Chir12.12 can also mediate depletion of peripheral B cells in non-human primates (NHPs).

Anti-CD40 mAbs with silenced ADCC activity are predicted to have an improved safety profile relative to the parental anti-CD40 antibodies, and in particular may be more suitable for non-oncologic indications, such as autoimmune diseases and use in a transplant setting.

The present invention therefore provides Fc silent anti-CD40 monoclonal antibodies that retain the non-agonistic, CD40L blocking attributes of the parental anti-CD40 antibody Chir12.12.

In particular, the invention provides an isolated antibody or a protein comprising an antigen-binding portion of an antibody directed against the target CD40 polypeptide (SEQ ID NO:28), characterized in that said antibody or protein
  a) binds to CD40 polypeptide with a $K_D$ of 10 nM or less, and,
  b) comprises a silent IgG Fc region.

In one embodiment, said antibody or protein inhibits CD40L induced signalling with an $IC_{50}$ of 50 ng/ml or less.

In another embodiment, the isolated antibody or protein according to the invention has no or low agonist activity with respect to CD40 signalling.

In another embodiment, the antibody or protein according to the present invention comprises a silent IgG Fc region selected from the group consisting of the amino acid sequence of SEQ ID NO:17, SEQ ID NO:18 or SEQ ID NO:19.

In another embodiment, the isolated antibody or protein of the invention comprises heavy chain ($V_H$) and light chain ($V_L$) variable regions having at least 60, 70, 80, 90, 95, 96, 97, 98, 99 or 100 percent sequence identity to $V_H$ of Chir12.12 (SEQ ID NO:9) and $V_L$ of Chir12.12 antibody (SEQ ID NO:10) respectively.

Specific examples of the antibodies according to the invention are
  mAb1 comprising heavy chain amino acid sequence of SEQ ID NO: 11 and light chain amino acid sequence of SEQ ID NO:12,
  mAb2 comprising heavy chain amino acid sequence of SEQ ID NO: 13 and light chain amino acid sequence of SEQ ID NO:14, or,
  mAb3 comprising heavy chain amino acid sequence of SEQ ID NO: 15 and light chain amino acid sequence of SEQ ID NO:16.

The isolated antibody or protein according to the invention may be used as a medicament. In particular, they are suitable for use in the treatment of autoimmune disorders, inflammatory disorders and/or in preventing or reducing the risk of graft rejection in transplantation.

The isolated antibody or protein according to the invention may be used in particular in the treatment of Multiple Sclerosis, Systemic Lupus Erythematosus, Sjögren's syndrome, Rheumatoid Arthritis, transplant rejection and graft-versus-host disease.

The invention also relates to pharmaceutical compositions comprising the above antibodies or proteins according to the invention, in combination with at least a pharmaceutically acceptable excipient, diluent or carrier. Said pharmaceutical compositions may additionally comprise other active ingredients.

The invention also relates to a lyophilisate or a liquid formulation of an antibody or protein according to the invention.

The invention further relates to the isolated nucleic acid encoding the antibody or protein according to the invention and the corresponding cloning or expression vector comprising at least one nucleic acid selected from the group consisting of SEQ ID NOs: 22 to 27.

The invention also relates to a host cell comprising one or more cloning or expression vectors as defined above.

The invention further provides a process for the production of an antibody or a protein of the invention, comprising culturing the host cell as defined above, purifying and recovering said antibody or protein.

In order that the present invention may be more readily understood, certain terms are first defined. Additional definitions are set forth throughout the detailed description.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" or "signaling activity" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction. Penultimate processes typically include nuclear events, resulting in a change in gene expression.

The term CD40 refers to human CD40, for example as defined in SEQ ID NO: 28, unless otherwise described.

The term "antibody" as referred to herein includes whole antibodies and any antigen binding fragments (i.e., "antigen-binding portion") or single chains thereof.

A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen (e.g., a portion of CD40). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR), or any fusion proteins comprising such antigen-binding portion.

Furthermore, although the two domains of the Fv fragment, $V_L$ and $V_H$, are coded for by separate genes, they can be joined, using recombinant methods, by a synthetic linker that enables them to be made as a single chain protein in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

As used herein, the term "IgG Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody. Accordingly, a composition of antibodies of the invention may comprise antibody populations with all K447 residues removed, antibody populations with no K447 residues removed, and antibody populations having a mixture of antibodies with and without the K447 residue.

An "isolated antibody", as used herein, refers to an antibody that is substantially free of other antibodies having different antigenic specificities (e.g., an isolated antibody that specifically binds to CD40 is substantially free of antibodies that specifically bind to other antigens than CD40). An isolated antibody that specifically binds to CD40 may, however, have cross-reactivity to other antigens, such as CD40 molecules from other (non-human) species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "humanized antibody", as used herein, is intended to include antibodies that contain minimal sequence derived from non-human immunoglobulin sequences. For the most part, humanized antibodies are human immunoglobulins (recipient antibody) in which residues from a hypervariable region (also known as complementarity determining region or CDR) of the recipient are replaced by residues from a hypervariable region of a non-human species (donor antibody) such as mouse, rat, rabbit, or non-human primate having the desired specificity, affinity and capacity. The phrase "complementarity determining region" refers to amino acid sequences which together define the binding affinity and specificity of the natural Fv region of a native immunoglobulin binding site. See, e.g. Chothia et al. (1987) J. Mol. Biol. 196:901-917: Kabat et al. (1991) US Dept. of Health and Human Services, NIH Publication No. 91-3242). The phrase "constant region" refers to the portion of the antibody molecule that confers effector functions. In previous work, directed towards producing non-immunogenic antibodies for use in therapy of human disease, mouse constant regions were substituted by human constant regions. The constant regions of the subject humanized antibodies were derived from human immunoglobulins. Humanization can be performed following the method of Winter and co-coworkers (Jones et al. (1986) Nature 321:522-525; Riechmann et al. (1988) Nature 332:323-327: Verhoeyen et al. (1988) Science 239: 1534-1536), by substituting rodent and mutant rodent CDRs or CDR sequences for the corresponding sequences of human antibody. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may comprise residues that are not found in the recipient antibody or in the donor antibody. The humanized antibody of the invention will also comprise at least a portion of an immunoglobulin constant region (Fc). Typically, that of a human immunoglobulin and in the present case, a silent Fc IgG region.

The antibodies of the invention may include amino acid residues not encoded by human sequences (e.g., mutations introduced by random or site-specific mutagenesis in vitro or by somatic mutation in vivo). In particular, the term "humanized antibody" include antibodies that comprise a silent variant of Fc IgG region.

The term "humanized monoclonal antibody" refers to antibodies displaying a single binding specificity which have variable regions in which the variable regions are humanized from non-human sequences.

The term "recombinant antibody", as used herein, includes all human or humanized antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human or humanized antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human or humanized antibodies have variable regions in which the framework and CDR regions may be derived from human germline immunoglobulin sequences. In certain embodiments, however, such recombinant human or humanized antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM, IgE, IgG such as IgG1 or IgG4) that is provided by the heavy chain constant region genes. Different isotypes have different effector function. For example, wild type human IgG1 and IgG3 isotypes mediate antibody-dependent cell-mediated cytotoxicity (ADCC) activity.

The phrases "an antibody recognizing an antigen" and "an antibody specific for an antigen" and "an antibody directed against an antigen" are used interchangeably herein with the term "an antibody which binds specifically to an antigen".

As used herein, an antibody or a protein that "specifically binds to CD40 polypeptide" is intended to refer to an antibody or protein that binds to human CD40 polypeptide with a $K_D$ of 100 nM or less, 10 nM or less, 1 nM or less.

An antibody that "cross-reacts with an antigen other than CD40" is intended to refer to an antibody that binds that antigen with a $K_D$ of 1 µM or less, 100 nM or less, 10 nM or less, 1 nM or less. An antibody that "does not cross-react with a particular antigen" is intended to refer to an antibody that binds to that antigen, with a $K_D$ of 100 nM or greater, or a $K_D$ of 1 µM or greater, or a $K_D$ of 10 µM or greater. In certain embodiments, such antibodies that do not cross-react with the antigen exhibit essentially undetectable binding against these proteins in standard binding assays.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction.

The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a BIACORE® system.

As used herein, the term "Affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

As used herein, the term "CD40 antagonist" is intended to refer to an antibody or protein that inhibits CD40 induced signaling activity in the presence of CD40L in a human cell assay such as the CD40L-mediated PBMC proliferation assay. Such assay is described in more detail in the examples below. In some embodiments, the antibodies or proteins of the invention inhibit CD40L induced signaling with an IC50 of 500 ng/ml or less, preferably with an IC50 of 50 ng/ml or less, for example with an IC50 of 20 ng/ml or less, as measured in CD40L-mediated PBMC proliferation assay.

As used herein, an antibody with "no agonist activity" is intended to refer to an antibody that does not significantly increase CD40 mediated signaling activity in the absence of CD40L in a cell-based assay, such as the CD40L-mediated PBMC proliferation assay. Such assay is described in more details in the examples below.

As used herein, the term "ADCC" or "antibody-dependent cellular cytotoxicity" activity refers to cell depleting activity. ADCC activity can be measured by the ADCC assay as described in more details in the Examples below.

As used herein, the term "silent" antibody refers to an antibody that exhibits no or low ADCC activity as measured in an ADCC assay as described in the Examples.

In one embodiment, the term "no or low ADCC activity" means that the silent antibody exhibits an ADCC activity that is below 50% specific cell lysis, for example below 10% specific cell lysis as measured in the ADCC assay as described in the Examples. No ADCC activity means that the silent antibody exhibits an ADCC activity (specific cell lysis) that is below 1%. In a specific embodiment, a silent antibody according to the invention does not exhibit any significant ADCC activity as measured in an ADCC assay as described in the Examples.

Silenced effector functions can be obtained by mutation in the Fc region of the antibodies and have been described in the art: LALA and N297A (Strohl, W., 2009, Curr. Opin. Biotechnol. vol. 20(6):685-691); and D265A (Baudino et al., 2008, J. Immunol. 181: 6664-69; Strohl, W., supra). Examples of silent Fc IgG1 antibodies comprise the so-called LALA mutant comprising L234A and L235A mutation in the IgG1 Fc amino acid sequence. Another example of a silent IgG1 antibody comprises the D265A mutation. Another silent IgG1 antibody comprises the N297A mutation, which results in aglycosylated/non-glycosylated antibodies.

As used herein, the term "selectivity" for an antibody or protein of the invention refers to an antibody or protein that binds to a certain target polypeptide but not to closely related polypeptides.

As used herein, the term "high affinity" for an antibody refers to an antibody having a $K_D$ of 1 nM or less for a target antigen. As used herein, the term "subject" includes any human or nonhuman animal.

The term "nonhuman animal" includes all vertebrates, e.g., mammals and non-mammals, such as non-human primates, sheep, dogs, cats, horses, cows, chickens, amphibians, reptiles, etc.

As used herein, the term, "optimized" means that a nucleotide sequence has been altered to encode an amino acid sequence using codons that are preferred in the production cell or organism, generally a eukaryotic cell, for example, a cell of *Pichia*, a cell of *Trichoderma*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in CHO mammalian cells, however optimized expression of these sequences in other eukaryotic cells is also envisioned herein. The amino acid sequences encoded by optimized nucleotide sequences are also referred to as optimized.

As used herein, the percent identity between the two sequences is a function of the number of identical positions shared by the sequences (i. e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. Alternatively, the percent identity between two amino acid sequences can be determined using the Needleman and Wunsch (J. Mol, Biol. 48:444-453, 1970) algorithm which has been incorporated into the GAP program in the GCG software package from ACCELRYS®, using either a Blossom 62 matrix or a PAM250 matrix, and a gap weight of 16, 14, 12, 10, 8, 6, or 4 and a length weight of 1, 2, 3, 4, 5, or 6.

The percent identity between two nucleotide amino acid sequences may also be determined using for example algorithms such as the BLASTN program for nucleic acid sequences using as defaults a word length (W) of 11, an expectation (E) of 10, M=5, N=4, and a comparison of both strands.

Recombinant Antibodies

Antibodies of the invention include the humanized recombinant antibodies mAb1-mAb3, isolated and structurally characterized by their full length heavy and light chain amino acid sequences as described in the Table 1 below:

TABLE 1

Full length heavy and light chain amino acid sequences of mAb1-mAb3

| Antibody | Full Length Heavy Chain Amino acid sequence | Full Length Light Chain Amino acid sequence |
| --- | --- | --- |
| mAb1 | SEQ ID NO: 11 | SEQ ID NO: 12 |
| mAb2 | SEQ ID NO: 13 | SEQ ID NO: 14 |
| mAb3 | SEQ ID NO: 15 | SEQ ID NO: 16 |

The corresponding variable regions, $V_H$ and $V_L$ amino acid sequences of such isolated antibodies mAb1-mAb3 of the invention all derived from the same antibody Chir12.12 previously described for example in WO2006/073443 and consisting of $V_H$ amino acid sequence of SEQ ID NO:7 and $V_L$ amino acid sequence of SEQ ID NO:8.

One important difference of the antibodies of the invention compared to original CHIR12.12 is that they have an Fc region, consisting of a silent Fc IgG region, for example silent Fc IgG1 region.

In particular, Table 2 summarizes the modification of Fc IgG1 region performed to obtain the antibodies mAb1-mAb3 as compared to original CHIR12.12 antibody.

TABLE 2

Modification of Fc IgG1 region to obtain mAb1-mAb3

| Antibody | Modification of Fc IgG1 region | Fc region Amino acid sequence |
|---|---|---|
| mAb1 | N297A | SEQ ID NO: 17 |
| mAb2 | D265A | SEQ ID NO: 18 |
| mAb3 | L234A/L235A | SEQ ID NO: 19 |

Other antibodies of the invention include those having amino acids that have been mutated by amino acid deletion, insertion or substitution, yet have at least 60, 70, 80, 90, 95, 96, 97, 98, 99 or 100 percent identity with the $V_H$ and $V_L$ regions of CHIR12.12, respectively SEQ ID NO:7 and SEQ ID NO:8 and comprising a silent IgG Fc region, for example a silent IgG1 Fc region.

In some embodiments, the antibody of the invention is a mutant variant of any one of mAb1-mAb3, wherein said mutant variant antibody include mutant amino acid sequences wherein no more than 1, 2, 3, 4 or 5 amino acids have been mutated by amino acid deletion, insertion or substitution in the $V_H$ and $V_L$ regions when compared with the $V_H$ and $V_L$ regions of CHIR12.12, respectively SEQ ID NO:7 and SEQ ID NO:8 and retaining the same constant regions as mAb1, mAb2 or mAb3.

Full length light and heavy chain nucleotide coding sequences of mAb1-mAb3 are shown in Table 3 below.

TABLE 3

Full length heavy and light chain DNA coding sequences

| Antibody | Full Length Heavy Chain DNA coding sequence | Full Length Light Chain DNA coding sequence |
|---|---|---|
| mAb1 | SEQ ID NO: 22 | SEQ ID NO: 23 |
| mAb2 | SEQ ID NO: 24 | SEQ ID NO: 25 |
| mAb3 | SEQ ID NO: 26 | SEQ ID NO: 27 |

Other nucleic acids encoding antibodies of the invention include nucleic acids that have been mutated by nucleotide deletion, insertion or substitution, yet have at least 60, 70, 80, 90, 95, 96, 97, 98, 99 or 100 percent identity to the $V_H$ and $V_L$ corresponding coding regions of CHIR12.12, as depicted in the sequences described for example in SEQ ID NO:20 and SEQ ID NO:21 respectively and comprising a coding sequence of a silent IgG Fc region, for example, a silent IgG1 Fc region.

In some embodiments, it includes variant nucleic acids wherein no more than 1, 2, 3, 4 or 5 nucleotides have been changed by nucleotide deletion, insertion or substitution in the $V_H$ and $V_L$ coding regions with the $V_H$ and $V_L$ coding regions depicted in the sequences described for example in SEQ ID NO:20 and SEQ ID NO:21 respectively, and retaining the same coding sequences of the constant regions as mAb1, mAb2 or mAb3 corresponding coding sequences.

Homologous Antibodies

In addition to the recombinant antibodies of the invention, mAb1-mAb3, the invention also encompasses homologous antibodies or proteins retaining the desired functional properties of mAb1-mAb3 antibodies.

In particular, said homologous antibodies or proteins according to the invention are antibodies or proteins comprising an antigen-binding portion of an antibody directed against a target CD40 polypeptide (SEQ ID NO:28), characterized in that said antibody or protein a) binds to CD40 polypeptide with a $K_D$ of 10 nM or less, and, b) comprises a silent IgG Fc region and wherein said homologous antibodies or proteins retain the desired functional properties of the original mAb1-mAb3 antibodies.

Desired functional properties of the original mAb1-mAb3 antibodies may be selected from one ore more of the following properties:

(i) it specifically binds to CD40, for example, a $K_D$ being 100 nM or less, 10 nM or less, or 1 nM or less, as measured in the BIACORE® assay;

(ii) it is a CD40 antagonist, for example, it inhibits CD40L induced signaling as measured in CD40L-mediated PBMC proliferation assay;

(iii) it exhibits no or low agonist activity, as measured in a CD40L-mediated PBMC proliferation assay;

(iv) it cross-reacts with Cynomolgus monkey CD40 polypeptide;

(v) it has no or low ADCC activity; and, (vi) it has suitable properties for drug development.

In one specific embodiment, said homologous antibodies or proteins according to the invention comprise a silent IgG1 Fc region, for example, a silent IgG1 Fc region selected from the group consisting of SEQ ID NO:17, SEQ ID NO:18 or SEQ ID NO:19.

In one specific embodiment, the invention relates to an antibody or protein which has variable region heavy and light chain nucleotide sequences, or variable region heavy and light chain amino acid sequences, or all 6 CDRs amino acid sequences or nucleotide coding sequences that are homologous to the corresponding amino acid or nucleotide sequences of the antibodies mAb1-mAb3 described above, in particular in Table 1, and said antibody or protein comprise a silent IgG Fc region selected from the group consisting of the Fc region of mAb1 (SEQ ID NO:17), the Fc region of mAb2 (SEQ ID NO:18) and the Fc region of mAb3 (SEQ ID NO:19), wherein said homologous antibody or protein specifically binds to CD40, and the antibody or protein exhibits the following functional properties: it is a CD40 antagonist, it exhibits no or low agonist activity, and it has no or low ADCC activity.

For example, the invention relates to antibodies or proteins homologous to mAb1-mAb3, comprising a silent IgG Fc region selected from the group consisting of the Fc region of mAb1 (SEQ ID NO:17), the Fc region of mAb2 (SEQ ID NO:18) and the Fc region of mAb3 (SEQ ID NO:19), and comprising a variable heavy chain ($V_H$) and a variable light chain ($V_L$) sequences where the CDR sequences share at least 60, 70, 90, 95, 96, 97, 98, 99 or 100 percent sequence identity to the corresponding CDR sequences of mAb1-mAb3, respectively SEQ ID NOs:1-6, wherein said homologous antibody or protein specifically binds to CD40, and the homologous antibody or protein exhibits the following functional properties: it is a CD40 antagonist, it exhibits no or low agonist activity, and it has no or low ADCC activity.

In a related specific embodiment, the homologous antibody or protein a) binds to CD40 with a $K_D$ of 1 nM or less;

b) inhibits CD40L induced signaling with an IC50 of 50 ng/ml or less as measured in CD40L-mediated PBMC proliferation assay described in the Examples;

c) has no or low agonist activity as measured in a bioassay such as CD40L-mediated PBMC proliferation assay as described in the Examples; and, d) has no or low ADCC activity.

The invention further relates to antibodies or proteins homologous to mAb1-mAb3, comprising a silent IgG Fc region selected from the group consisting of the Fc region of mAb1 (SEQ ID NO:17), the Fc region of mAb2 (SEQ ID NO:18) and the Fc region of mAb3 (SEQ ID NO:19), and comprising a variable heavy chain ($V_H$) and a variable light chain ($V_L$) sequences which share at least 80, 90, 95, 96, 97, 98, 99 or 100 percent sequence identity to the corresponding ($V_H$) and ($V_L$) sequences of mAb1-mAb3, respectively SEQ ID NO:7 and SEQ ID NO:8, wherein said homologous antibody or protein specifically binds to CD40, and the antibody or protein exhibits the following functional properties: it is a CD40 antagonist, it exhibits no or low agonist activity, and it has no or low ADCC activity.

In a related specific embodiment, said homologous antibody or protein
a) binds to CD40 with a $K_D$ of 1 nM or less;
b) inhibits CD40L induced signaling with an IC50 of 50 ng/ml or less as measured in CD40L-mediated PBMC proliferation assay described in the Examples;
c) has no or low agonist activity as measured in a bioassay such as CD40L-mediated PBMC proliferation assay described in the Examples; and,
d) has no or low ADCC activity.

In another example, the invention relates to antibodies or proteins homologous to mAb1-mAb3 comprising a silent IgG Fc region selected from the group consisting of the Fc region of mAb1 (SEQ ID NO:17), the Fc region of mAb2 (SEQ ID NO:18) and the Fc region of mAb3 (SEQ ID NO:19), and wherein: the variable heavy and light chains are encoded by a nucleotide sequence that is at least 80%, at least 90%, at least 95%, or 100% identical to the corresponding coding nucleotide sequence of the variable heavy and light chains of mAb1-mAb3, wherein said homologous antibody or protein specifically binds to CD40, and the antibody or protein exhibits the following functional properties: it is a CD40 antagonist, it exhibits no or low agonist activity, and it has no or low ADCC activity.

In a related specific embodiment, said homologous antibody or protein
a) binds to CD40 with a $K_D$ of 1 nM or less;
b) inhibits CD40L induced signaling with an IC50 of 50 ng/ml or less as measured in CD40L-mediated PBMC proliferation assay described in the Examples;
c) has no or low agonist activity as measured in a bioassay such as CD40L-mediated PBMC proliferation assay described in the Examples; and,
d) has no or low ADCC activity.

Antibodies with mutant amino acid sequences can be obtained by mutagenesis (e.g., site-directed or PCR-mediated mutagenesis) of the coding nucleic acid molecules, followed by testing of the encoded altered antibody for retained function (i.e., the functions set forth above) using the functional assays described in the Examples below.

In certain embodiments, the antibodies or proteins homologous to mAb1-mAb3 as described above have conservative sequence modifications.

As used herein, the term "conservative sequence modifications" is intended to refer to amino acid substitutions in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), non-polar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

Modifications can be introduced into an antibody of the invention by standard techniques known in the art, such as site-directed mutagenesis and PCR-mediated mutagenesis.

Nucleic Acid Molecules Encoding Antibodies or Proteins of the Invention

Another aspect of the invention pertains to nucleic acid molecules that encode the antibodies or proteins of the invention as described above.

Examples of light and heavy chains nucleotide sequences of any one of mAb1 to mAb3 can be derived from the Table 3 (showing the entire nucleotide coding sequences of heavy and light chains of mAb1 to mAb3).

Other examples of light and heavy chains nucleotide sequences according to the invention are any sequence coding for the full length heavy and/or light amino acid sequences of mAb1, mAb2 or mAb3 as described in Table 1.

The invention also pertains to nucleic acid molecules that derive from the latter sequences having been optimized for protein expression in mammalian cells, for example, CHO cell lines.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the invention can be obtained using standard molecular biology techniques. Once DNA fragments encoding, for example, $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding the antibody constant region of mAb1-mAb3 comprising Fc region as defined in SEQ ID NOs:17-19.

The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., el al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region may be selected among IgG1 isotypes comprising Fc region as defined in SEQ ID NOs:17-19.

The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

Generation of Transfectomas Producing Monoclonal Antibodies

Antibodies or proteins of the invention can be produced in a host cell transfectoma using, for example, a combination of recombinant DNA techniques and gene transfection methods as is well known in the art (e.g., Morrison, S. (1985) Science 229:1202).

For example, to express the antibodies, DNAs encoding partial or full-length light and heavy chains can be obtained by standard molecular biology or biochemistry techniques (e.g., DNA chemical synthesis, PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes by inserting them into expression vectors already encoding heavy chain constant and light chain constant regions of the desired sequence corresponding to said constant regions of mAb1, mAb2 or mAb3 such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains are transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, for example mammalian host cells, yeast or filamentous fungi, is discussed because such eukaryotic cells, and in particular mammalian cells, are more likely than prokaryotic cells to assemble and secrete a properly folded and immunologically active antibody.

In one specific embodiment, a cloning or expression vector according to the invention comprises either at least one of the following coding sequences (a)-(c), operatively linked to suitable promoter sequences:

(a) SEQ ID NO:22 and SEQ ID NO:23 encoding respectively the full length heavy and light chains of mAb1;
(b) SEQ ID NO:24 and SEQ ID NO:25 encoding respectively the full length heavy and light chains of mAb2; or,
(c) SEQ ID NO:26 and SEQ ID NO:27 encoding respectively the full length heavy and light chains of mAb3.

Mammalian host cells for expressing the recombinant antibodies of the invention include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g., as described in R. J. Kaufman and P. A. Sharp, 1982 Mol. Biol. 159:601-621), CHOK1 dhfr+ cell lines, NSO myeloma cells, COS cells and SP2 cells. In particular, for use with NSO myeloma cells, another expression system is the GS gene expression system shown in PCT Publications WO 87/04462, WO 89/01036 and EP 0 338 841.

When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods (See for example Abhinav et al. 2007, Journal of Chromatography 848: 28-37).

In one specific embodiment, the host cell of the invention is a host cell transfected with an expression vector having the coding sequences selected from the group consisting of (a)-(c) suitable for the expression of mAb1-mAb3 respectively, operatively linked to suitable promoter sequences:
(a) SEQ ID NO:22 and SEQ ID NO:23;
(b) SEQ ID NO:24 and SEQ ID NO:25; and,
(c) SEQ ID NO:26 and SEQ ID NO:27.

The latter host cells may then be further cultured under suitable conditions for the expression and production of an antibody of the invention selected from the group consisting of mAb1-mAb3 respectively.

Bispecific Molecules

In another aspect, the present invention features bispecific or multispecific molecules comprising an anti-CD40 antibody or protein of the invention. An antibody or protein of the invention can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody or protein of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for CD40, for example, one antigen-binding portion of any one of mAb1-mAb3 and a second binding specificity for a second target epitope. For example, the second target epitope is another epitope of CD40 different from the first target epitope. Another example is a bispecific molecule comprising at least one first binding specificity for CD40, for example, one antigen-binding portion of any one of mAb1-mAb3 and a second binding specificity for an epitope within CD40.

Additionally, for the invention in which the bispecific molecule is multi-specific, the molecule can further include a third binding specificity, in addition to the first and second target epitope.

The bispecific molecules of the present invention can be prepared by conjugating the constituent binding specificities, using methods known in the art. For example, each binding-specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particular embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb x mAb, mAb x Fab, Fab x F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

Multivalent Antibodies

In another aspect, the present invention provides multivalent antibodies comprising at least two identical or different antigen-binding portions of the antibodies of the invention binding to CD40, for example, selected from antigen-binding portions of any one of mAb1-mAb3. In one embodiment, the multivalent antibodies provide at least two, three or four antigen-binding portions of the antibodies. The antigen-binding portions can be linked together via protein fusion or covalent or non-covalent linkage. Alternatively, methods of linkage have been described for the bispecific molecules. Tetravalent compounds can be obtained for example by cross-linking antibodies of the antibodies of the invention with an antibody that binds to the constant regions of the antibodies of the invention, for example the Fc or hinge region.

Methods of Therapy Using the Antagonist Anti-CD40 Antibodies of the Invention

Methods of the invention are directed to the use of the anti-CD40 antibodies or proteins of the invention to treat subjects (i.e., patients) having an autoimmune disease and/or inflammatory disease, or a predisposition to developing an autoimmune disease and/or inflammatory disease, wherein the disease and/or inflammation is mediated by CD40L-mediated CD40 signaling on cells expressing the CD40 antigen.

Methods for detecting CD40 expression in cells are well known in the art and include, but are not limited to, PCR techniques, immunohistochemistry, flow cytometry, Western blot, ELISA, and the like.

The methods of the invention are especially useful for treating inflammatory and/or autoimmune diseases wherein CD40L-mediated CD40 stimulation is involved.

Inflammatory diseases are characterized by inflammation and tissue destruction, or a combination thereof. "Inflammatory disease" includes any inflammatory immune-mediated process where the initiating event or target of the immune response involves non-self-antigen (s), including, for example, alloantigens, xenoantigens, viral antigens, bacterial antigens, unknown antigens, or allergens.

Further, for purposes of the present invention, the term "inflammatory disease(s)" includes "autoimmune disease(s)". As used herein, the term "autoimmunity" is generally understood to encompass inflammatory immune-mediated processes involving "self" antigens. In autoimmune diseases, self-antigen(s) trigger host immune responses.

Also, the present invention includes treatment of inflammation associated with tissue transplant rejection. "Transplant rejection" or "graft rejection" refers to any host-mounted immune response against a graft including but not limited to HLA antigens, blood group antigens, and the like.

The invention can also be used to treat graft versus host disease, such as that associated with bone marrow transplantation, for example. In such graft versus host disease, the donor bone marrow includes lymphocytes and cells that mature into lymphocytes. The donors lymphocytes recognize the recipient's antigens as non-self and mount an inflammatory immune response. Hence, as used herein, "graft versus host disease" or "graft versus host reaction" refers to any T cell mediated immune response in which donor lymphocytes react to the host's antigens.

The antagonist anti-CD40 antibodies or proteins described herein, for example mAb1, mAb2 or mAb3, can be used in accordance with the methods of the invention to treat autoimmune and/or inflammatory disorders including, but not limited to, systemic lupus erythematosus (SLE), discoid lupus, lupus nephritis, sarcoidosis, inflammatory arthritis, including juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis *nodosa*, primary biliary cirrhosis, inflammatory bowel disease, Crohn's disease, celiac's disease (gluten-sensitive enteropathy), primary Sjögren's syndrome (pSS), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue, immune dysfunction syndrome (CFIDS), polymyositis and dermatomyositis, cryoglobulinemia, thrombolysis, cardiomyopathy, pemphigus vulgaris, pulmonary interstitial fibrosis, Type I and Type II diabetes mellitus, type 1, 2, 3, and 4 delayed-type hypersensitivity, allergy or allergic disorders, unwanted/unintended immune responses to therapeutic proteins (see for example, U. S. Patent Application No. US 2002/0119151 and Koren, et al. (2002) Curr. Pharm. Biotechnol. 3: 349-60), asthma, Churg-Strauss syndrome (allergic granulomatosis), atopic dermatitis, allergic and irritant contact dermatitis, urtecaria, IgE-mediated allergy, atherosclerosis, ANCA-associated Vasculitides, vasculitis, idiopathic inflammatory myopathies, hemolytic disease, Alzheimer's disease, chronic inflammatory demyelinating polyneuropathy, and the like.

Genetic ablation or pharmacological inhibition of the CD40-CD154 pathway has previously demonstrated therapeutic benefit in either the clinic or in preclinical models of SLE, pSS, ITP, MS, Crohn's disease, Pemphigus vulgaris, autoimmune vasculitis and RA (Law C L, Grewal I S. (2009). Adv. Exp. Med. Biol. 2009; 647:8-36); the medical need of which is detailed below.

In preferred embodiments the anti-CD40 antibodies or proteins of the invention are useful in treating: (i) systemic lupus erythematosus (lupus nephritis), preferably in providing effective steroid-sparing therapies for induction and maintenance of remission, and prevention of end-stage renal disease; (ii) primary Sjögren's syndrome, preferably in prevention of salivary and lacrimary gland destruction, and induction and maintenance of remission of extraglandular manifestations; (iii) autoimmune thrombocytopenic purpura, preferably treatment of patients refractory to standard of care; (iv) ANCA-associated Vasculitides, preferably inducing and maintaining remission in patients refractory to corticosteroids, and steroid-sparing treatment; (v) Pemphigus Vulgaris, preferably in induction and maintenance of remission in patients refractory to corticosteroids, and steroid-sparing treatment; (vi) Multiple Sclerosis, preferably in providing more effective treatments for prevention of relapses and disability progression, and achieving disease-free status; and (vii) Crohn's disease, preferably in providing more effective therapies for maintenance of remission, and treatment of patients refractory to anti-TNF.

In some other embodiments, the anti-CD40 antibodies or proteins of the invention are useful in treating pulmonary inflammation including but not limited to lung graft rejection, asthma, sarcoidosis, emphysema, cystic fibrosis, idiopathic pulmonary fibrosis, chronic bronchitis, allergic rhinitis and allergic diseases of the lung such as hypersensitivity pneumonitis, eosinophilic pneumonia, bronchiolitis obliterans due to bone marrow and/or lung transplantation or other causes, graft atherosclerosis/graft phlebosclerosis, as well as pulmonary fibrosis resulting from collagen, vascular, and autoimmune diseases such as rheumatoid arthritis, scleroderma and lupus erythematosus.

"Treatment" is herein defined as the application or administration of an anti-CD40 antibody or protein according to the invention, for example, mAb1, mAb2 or mAb3 antibody, to a subject, or application or administration a pharmaceutical composition comprising said anti-CD40 antibody or protein of the invention to an isolated tissue or cell line from a subject, where the subject has an autoimmune disease and/or inflammatory disease, a symptom associated with an autoimmune disease and/or inflammatory disease, or a predisposition toward development of an autoimmune disease and/or inflammatory disease, where the purpose is to cure, heal, alleviate, relieve, alter, remedy, ameliorate, improve, or affect the autoimmune disease and/or inflammatory disease, any associated symptoms of the autoimmune disease and/or inflammatory disease, or the predisposition toward the development of the autoimmune disease and/or inflammatory disease.

By "treatment" is also intended the application or administration of a pharmaceutical composition comprising an anti-CD40 antibodies or protein of the invention, for example, mAb1, mAb2 or mAb3 antibody, to a subject, or application or administration of a pharmaceutical composition comprising said anti-CD40 antibody or protein of the invention to an isolated tissue or cell line from a subject, where the subject has an autoimmune disease and/or inflammatory disease, a symptom associated with an autoimmune disease and/or inflammatory disease, or a predisposition toward development of an autoimmune disease and/or inflammatory disease, where the purpose is to cure, heal, alleviate, relieve, alter, remedy, ameliorate, improve, or affect the autoimmune disease and/or inflammatory disease, any associated symptoms of the autoimmune disease and/or inflammatory disease, or the predisposition toward the development of the autoimmune disease and/or inflammatory disease.

By "anti-inflammatory activity" is intended a reduction or prevention of inflammation. Therapy with at least one anti-CD40 antibody or protein according to the invention causes a physiological response that is beneficial with respect to treatment of an autoimmune disease and/or inflammatory disease, where the disease involves cells expressing the CD40 antigen. It is recognized that the methods of the invention may be useful in preventing phenotypic change in cells such as proliferation, activation, and the like.

In accordance with the methods of the present invention, at least one anti-CD40 antibody or protein of the invention as defined above herein is used to promote a positive therapeutic response with respect to treatment or prevention of an autoimmune disease and/or inflammatory disease.

By "positive therapeutic response" with respect to an autoimmune disease and/or inflammatory disease is intended an improvement in the disease in association with the anti-inflammatory activity of these antibodies or proteins, and/or an improvement in the symptoms associated with the disease. That is, an anti-proliferative effect, the prevention of further proliferation of the CD40-expressing cell, a reduction in the inflammatory response including but not limited to reduced secretion of inflammatory cytokines, adhesion molecules, proteases, immunoglobulins (in instances where the CD40 bearing cell is a B cell), combinations thereof, and the like, increased production of anti-inflammatory proteins, a reduction in the number of autoreactive cells, an increase in immune tolerance, inhibition of autoreactive cell survival, and/or a decrease in one or more symptoms mediated by stimulation of CD40-expressing cells can be observed. Such positive therapeutic responses are not limited to the route of administration and may comprise administration to the donor, the donor tissue (such as for example organ perfusion), the host, any combination thereof, and the like.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the antagonist anti-CD40 antibody or protein of the invention may experience the beneficial effect of an improvement in the symptoms associated with the disease.

By "therapeutically effective dose or amount" or "effective amount" is intended an amount of anti-CD40 antibody or protein of the invention that, when administered brings about a positive therapeutic response with respect to treatment of a subject with an autoimmune disease and/or inflammatory disease.

In some embodiments of the invention, a therapeutically effective dose of the anti-CD40 antibody or protein of the invention, for example, mAb1, mAb2 or mAb3 is in the range from 0.01 mg/kg to 40 mg/kg, from 3 mg/kg to 20 mg/kg or from 7 mg/kg to 12 mg/kg. It is recognized that the method of treatment may comprise a single administration of a therapeutically effective dose or multiple administrations of a therapeutically effective dose of the antagonist anti-CD40 antibody or protein of the invention.

A further embodiment of the invention is the use of anti-CD40 antibodies or proteins of the invention for diagnostic monitoring of protein levels in tissue as part of a clinical testing procedure, e.g., to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

The anti-CD40 antibodies or proteins of the invention, for example, mAb1, mAb2 or mAb3 can be used in combination with any known therapies for autoimmune and inflammatory diseases, including any agent or combination of agents that are known to be useful, or which have been used or are currently in use, for treatment of autoimmune and inflammatory diseases. Such therapies and therapeutic agents include, but are not limited to, surgery or surgical procedures (e.g. splenectomy, lymphadenectomy, thyroidectomy, plasmaphoresis, leukophoresis, cell, tissue, or organ transplantation, intestinal procedures, organ perfusion, and the like), radiation therapy, therapy such as steroid therapy and non-steroidal therapy, hormone therapy, cytokine therapy, therapy with dermatological agents (for example, topical agents used to treat skin conditions such as allergies, contact dermatitis, and psoriasis), immunosuppressive therapy, and other anti-inflammatory monoclonal antibody therapy, and the like. In this manner, the antagonist anti-CD40 antibodies or proteins described herein are administered in combination with at least one other therapy, including, but not limited to, surgery, organ perfusion, radiation therapy, steroid therapy, non-steroidal therapy, antibiotic therapy, antifungal therapy, hormone therapy, cytokine therapy, therapy with dermatological agents (for example, topical agents used to treat skin conditions such as allergies, contact dermatitis, and psoriasis), immunosuppressive therapy, other anti-inflammatory monoclonal antibody therapy, combinations thereof, and the like.

Thus, where the combined therapies comprise administration of an anti-CD40 antibody or protein of the invention such as mAb1, mAb2 or mAb3 antibody, in combination with administration of another therapeutic agent, as with steroids as one example, the methods of the invention encompass co-administration, using separate formulations or a single pharmaceutical formulation, and consecutive administration in either order. Where the methods of the present invention comprise combined therapeutic regimens, these therapies can be given simultaneously, i.e., the anti-CD40 antibody or protein of the invention is administered concurrently or within the same time frame as the other therapy (i.e., the therapies are going on concurrently, but the anti-CD40 antibody or protein of the invention is not administered precisely at the same time as the other therapy). Alternatively, the anti-CD40 antibody of the present invention or protein of the invention may also be administered prior to or subsequent to the other therapy. Sequential administration of the different therapies may be performed regardless of whether the treated subject responds to the first course of therapy to decrease the possibility of remission or relapse.

In some embodiments of the invention, the anti-CD40 antibodies or proteins of the invention, for example mAb1, mAb2 or mAb3 antibody, are administered in combination with immunosuppressive drugs or anti-inflammatory drugs, wherein the antibody or protein and the therapeutic agent(s) may be administered sequentially, in either order, or simultaneously (i.e., concurrently or within the same time frame). Examples of suitable immunosuppressive drugs that can be administered in combination with the antagonistic anti-CD40 antibodies or proteins of the invention, for example mAb1, mAb2 or mAb3 antibody, include, but are not limited to, methotrexate, cyclophosphamide, mizoribine, chlorambucil, cyclosporine, such as, for example, aerosolized cyclosporine (see, U. S. Patent Application Publication No. US 2002/0006901), tacrolimus (FK506; PROGRAF®), mycophenolate mofetil, and azathioprine (6-mercaptopurine), sirolimus (rapamycin), deoxyspergualin, leflunomide and its malononitriloamide analogs; and immunosuppressive proteins, including, for example, anti-CTLA4 antibodies and Ig fusions, anti-B lymphocyte stimulator antibodies (e.g., LYMPHOSTAT-B™) and Ig fusions (BLyS-Ig), anti-CD80 antibodies and etanercept (ENBREL®), as well as anti-T cell antibodies such as anti-CD3 (ORTHOCLONE OKT3®), anti-CD4, and the like. Examples of suitable anti-inflammatory agents include, but are not limited to, corticosteroids such as, for example, clobetasol, halobetasol, hydrocortisone, triamcinolone, betamethasone, fluocinole, fluocinonide, prednisone, prednisolone, methylprednisolone; non-steroidal anti-inflammatory drugs (NSAIDs) such as, for example, sulfasalazine, medications containing mesalamine (known as 5-ASA agents), celecoxib, diclofenac, etodolac, fenprofen, flurbiprofen, ibuprofen, ketoprofen, meclofamate, meloxicam, nabumetone, naproxen, oxaprozin, piroxicam, rofecoxib, salicylates, sulindac, and tolmetin; phosphodiesterase-4 inhibitors, anti-inflammatory antibodies such as adalimumab (HUMIRA®, a TNF-α antagonist) and infliximab (REMICADE®, a TNF-α antagonist), and the like. Also included are immune modulating agents of current or potential use in treating autoimmune disease, such as thalidomide or its analogs such as lenalidomide.

Transplant rejection and graft versus host disease can be hyperacute (humoral), acute (T cell mediated), or chronic (unknown etiology), or a combination thereof. Thus, the anti-CD40 antibodies or proteins of the invention, for example mAb1, mAb2 or mAb3 antibody, are used in some embodiments to prevent and/or ameliorate rejection and/or symptoms associated with hyperacute, acute, and/or chronic transplant rejection of any tissue, including, but not limited to, liver, kidney, pancreas, pancreatic islet cells, small intestine, lung, heart, corneas, skin, blood vessels, bone, heterologous or autologous bone marrow, and the like. Graft tissues may be obtained from any donor and transplanted into any recipient host, and thus the transplant procedure may comprise transplanting animal tissue to humans (e.g. xenografts), transplanting tissue from one human to another human (e.g. allografts), and/or transplanting tissue from one part of a human's body to another (e.g. autografts).

Treatment with the antibodies or proteins of the invention may also reduce transplantation sequelae such as fever, anorexia, hemodynamic abnormalities, leukopenia, white cell infiltration of the transplanted organ/tissue, as well as opportunistic infections.

In some embodiments, the anti-CD40 antibodies or proteins of the invention, for example mAb1, mAb2 or mAb3 antibody, may be used alone or in combination with immunosuppressive drugs to treat and/or prevent transplant rejection such as hyperacute, acute, and/or chronic rejection and/or graft versus host disease.

Thus, in some embodiments where the anti-CD40 antibodies or proteins of the invention are used to treat graft rejection, the antibodies, for example mAb1, mAb2 or mAb3 antibody, may be used in combination with suitable immunosuppressive drugs, including, but not limited, to methotrexate; cyclophosphamide; mizoribine; chlorambucil; cyclosporine, such as, for example, aerosolized cyclosporine (see, U. S. Patent Application Publication No. US20020006901), tacrolimus (FK506; PROGRAF®), mycophenolate mofetil, and azathioprine (6-mercaptopurine), sirolimus (rapamycin), deoxyspergualin, leflunomide and its malononitriloamide analogs; immune modulators, including for example thalidomide and its analogs; and immunosuppressive proteins, including, for example, anti-CTLA antibodies and Ig fusions, anti-B lymphocyte stimulator antibodies (e.g., LYMPHOSTAT-B™) and Ig fusions (BLyS-Ig), anti-CD80 antibodies and etanercept (ENBREL®), as well as anti-T cell antibodies such as anti-CD3 (ORTHOCLONE OKT3®), anti-CD4, and the like.

As such, it is specifically contemplated that the compositions and methods of the invention are used in combination with other drugs to further improve symptoms and outcomes in transplant recipients, such as those receiving lung or kidney grafts, for example. Thus, in some embodiments, the anti-CD40 antibodies or proteins of the invention, for example mAb1, mAb2 or mAb3 antibody, are used to treat transplant rejection (such as, for example hyperacute, acute, and/or chronic rejection or graft versus host disease in lung or renal transplant recipients) alone or in combination with parenterally and/or non-parenterally administered cyclosporine, including for example oral cyclosporine, injectable cyclosporine, aerosolized (e.g. inhaled) cyclosporine, and combinations thereof. In some embodiments where at least a component of the therapy is aerosolized cyclosporine, the cyclosporine is delivered to the lung of the recipient by inhalation of cyclosporine in aerosol spray form using, for example, a pressurized delivery device or nebulizer. The cyclosporine may be administered in either dry powder or wet form. The cyclosporine may be administered as a sub therapeutic dose.

In some other embodiments, the anti-CD40 antibodies or proteins of the invention, for example mAb1, mAb2 or mAb3 antibody, may be used alone or in combination with immunosuppressive drugs to treat and/or prevent rheumatoid arthritis. Thus in some embodiments where the anti-CD40 antibodies or proteins of the invention; for example mAb1, mAb2 or mAb3 antibody, are used to treat rheumatoid arthritis, said antibodies or proteins may be used in combination with suitable immunosuppressive drugs, including, but not limited to, methotrexate, cyclophosphamide, mizoribine, chlorambucil, cyclosporine, tacrolimus (FK506; PROGRAF®), mycophenolate mofetil, and azathioprine (6-mercaptopurine), sirolimus (rapamycin), deoxyspergualin, leflunomide and its malononitriloamide analogs; and immunosuppressive proteins, including, for example, anti-CTLA antibodies and Ig fusions, anti-B lymphocyte stimulator antibodies (e.g., LYMPHOSTAT-B™) and Ig fusions (BLyS-Ig), anti-CD20 antibodies (e.g. RITUXAN®); the fully human antibody HuMax-CD20, R-1594, IMMU-106, TRU-015, AME-133, tositumomab/1-131, tositumomab (BEXXAR®, ibritumomab tituxetan (ZEVALIN®); anti-CD80 antibodies, and etanercept (ENBREL®), as well as anti-T cell antibodies such as anti-CD3 (ORTHOCLONE OKT3®), anti-CD4, and the like. As discussed above, treatment effectiveness may be assessed using any means and includes, but is not limited to, effectiveness as measured by clinical responses defined by the American College of Rheumatology criteria, the European League of Rheumatism criteria, or any other criteria. See for example, Felson et al. (1995) Arthritis. Rheum. 38: 727-35 and van Gestel et al. (1996) Arthritis Rheum. 39: 34-40.

In yet other embodiments, the anti-CD40 antibodies or proteins of the invention, for example mAb1, mAb2 or mAb3 antibody, may be used alone or in combination with immunosuppressive drugs to treat and/or prevent multiple sclerosis. Thus in some embodiments where the anti-CD40 antibodies or proteins of the invention, for example mAb1, mAb2 or mAb3 antibody, are used to treat multiple sclerosis, the antibodies may be used in combination with suitable immunosuppressive drugs, including, but not limited to, methotrexate, cyclophosphamide, mizoribine, chlorambucil, cyclosporine, tacrolimus (FK506; PROGRAF®), mycophenolate mofetil, and azathioprine (6-mercaptopurine), sirolimus (rapamycin), deoxyspergualin, leflunomide and its malononitriloamide analogs; and immunosuppressive proteins, including, for example, anti-CTLA antibodies and Ig fusions, anti-B lymphocyte stimulator antibodies (e.g., LYMPHOSTAT-B™) and Ig fusions (BLyS-Ig), anti-CD20 antibodies (e.g., RITUXAN®; the fully human antibody HuMax-CD20, R-1594, IMMIJ-106, TRU-015, AME-133, tositumomab/1-131, tositumomab (BEXXAR®), ibritumomab tituxetan (ZEVALIN®); anti-CD80 antibodies, and etanercept (ENBREL®), as well as anti-T cell antibodies such as anti-CD3 (ORTHOCLONE OKT3®), anti-CD4, agents involved in S1P receptor modulation, including for example fingolimod; and the like.

Pharmaceutical Formulations and Modes of Administration

The anti-CD40 antibodies or proteins of this invention are administered at a concentration that is therapeutically effective to prevent or treat autoimmune diseases and/or inflammatory diseases and/or to prevent or reduce risks associated to graft rejection in transplantation.

To accomplish this goal, the antibodies may be formulated using a variety of acceptable excipients known in the art. Typically, the antibodies or proteins are administered by injection, for example, either intravenously, intraperitoneally, or subcutaneously. Methods to accomplish this administration are known to those of ordinary skill in the art. It may also be possible to obtain compositions that may be topically or orally administered, or which may be capable of transmission across mucous membranes.

Intravenous administration occurs preferably by infusion over a period of about 1 to about 10 hours, more preferably over about 1 to about 8 hours, even more preferably over about 2 to about 7 hours, still more preferably over about 4 to about 6 hours, depending upon the anti-CD40 antibody or protein being administered. The initial infusion with the pharmaceutical composition may be given over a period of about 4 to about 6 hours with subsequent infusions delivered more quickly. Subsequent infusions may be administered over a period of about 1 to about 6 hours, including, for example, about 1 to about 4 hours, about 1 to about 3 hours, or about 1 to about 2 hours.

A pharmaceutical composition of the invention is formulated to be compatible with its intended route of administration. Examples of possible routes of administration include parenteral, (e.g., intravenous (IV), intramuscular (IM), intradermal, subcutaneous (SC), or infusion), oral and pulmonary (e.g., inhalation), nasal, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

The anti-CD40 antibodies or proteins of the invention are typically provided by standard technique within a pharmaceutically acceptable buffer, for example, sterile saline, sterile buffered water, propylene glycol, combinations of the foregoing, etc. Methods for preparing parenterally administrable agents are described in Remington's Pharmaceutical Sciences (18th ed.; Mack Publishing Company, Eaton, Pa., 1990). See also, for example, WO 98/56418, which describes stabilized antibody pharmaceutical formulations suitable for use in the methods of the present invention.

The amount of at least one antagonist anti-CD40 antibody or proteins of the invention to be administered is readily determined by one of ordinary skill in the art. Factors influencing the mode of administration and the respective amount of at least one antagonist anti-CD40 antibody or protein include, but are not limited to, the particular disease undergoing therapy, the severity of the disease, the history of the disease, and the age, height, weight, health, and physical condition of the individual undergoing therapy. Similarly, the amount of antagonist anti-CD40 antibody or protein to be administered will be dependent upon the mode of administration and whether the subject will undergo a single dose or multiple doses of this agent. Generally, a higher dosage of anti-CD40 antibody or protein is preferred with increasing weight of the patient undergoing therapy. The dose of anti-CD40 antibody or protein to be administered is in the range from about 0.003 mg/kg to about 50 mg/kg, preferably in the range of 0.01 mg/kg to about 40 mg/kg.

Thus, for example, the dose can be 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, or 50 mg/kg.

In another embodiment of the invention, the method comprises administration of multiple doses of antagonist anti-CD40 antibody or fragment thereof. The method may comprise administration of 1, 2, 3, 4, 5, 6, 7, 8, 9, 10, 15, 20, 25, 30, 35, 40, or more therapeutically effective doses of a pharmaceutical composition comprising an antagonist anti-CD40 antibody or fragment thereof. The frequency and duration of administration of multiple doses of the pharmaceutical compositions comprising anti-CD40 antibody or protein can be readily determined by one of skill in the art. Moreover, treatment of a subject with a therapeutically effective amount of an antibody or protein can include a single treatment or, preferably, can include a series of treatments. In a preferred example, a subject is treated with antagonist anti-CD40 antibody or protein of the invention in the range of between about 0.1 to 20 mg/kg body weight, once per week for between about 1 to 10 weeks, preferably between about 2 to 8 weeks, more preferably between about 3 to 7 weeks, and even more preferably for about 4, 5, or 6 weeks. Treatment may occur annually to prevent relapse or upon indication of relapse. It will also be appreciated that the effective dosage of antibody or antigen-binding fragment thereof used for treatment may increase or decrease over the course of a particular treatment. Changes in dosage may result and become apparent from the results of diagnostic assays as described herein.

Thus, in one embodiment, the dosing regimen includes a first administration of a therapeutically effective dose of at least one anti-CD40 antibody or protein of the invention on days 1, 7, 14, and 21 of a treatment period. In another embodiment, the dosing regimen includes a first administration of a therapeutically effective dose of at least one anti-CD40 antibody or protein of the invention on days 1, 2, 3, 4, 5, 6, and 7 of a week in a treatment period. Further embodiments include a dosing regimen having a first administration of a therapeutically effective dose of at least one anti-CD40 antibody or protein of the invention on days 1, 3, 5, and 7 of a week in a treatment period; a dosing regimen including a first administration of a therapeutically effective dose of at least one anti-CD40 antibody or protein of the invention on days 1 and 3 of a week in a treatment period; and a preferred dosing regimen including a first administration of a therapeutically effective dose of at least one anti-CD40 antibody or protein of the invention on day 1 of a week in a treatment period. The treatment period may comprise 1 week, 2 weeks, 3 weeks, a month, 3 months, 6 months, or a year. Treatment periods may be subsequent or separated from each other by a day, a week, 2 weeks, a month, 3 months, 6 months, or a year. ranges from 0.003 mg/kg to 50 mg/kg, from 0.01 mg/kg to 40 mg/kg, from 0.01 mg/kg to 30 mg/kg, from 0.1 mg/kg to 30 mg/kg, from 0.5 mg/kg to 30 mg/kg, from 1 mg/kg to 30 mg/kg, from 3 mg/kg to 30 mg/kg, from 3 mg/kg to 25 mg/kg, from 3 mg/kg to 20 mg/kg, from 5 mg/kg to 15 mg/kg, or from 7 mg/kg to 12 mg/kg. Thus, for example, the dose of any one antagonist anti-CD40 antibody or antigen-binding fragment thereof, for example the anti-CD40 monoclonal antibody or protein of the invention, can be 0.003 mg/kg, 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, 50 mg/kg, or other such doses falling within the range of 0.003 mg/kg to 50 mg/kg. The same therapeutically effective dose of an anti-CD40 antibody or protein of the invention can be administered throughout each week of antibody dosing.

Alternatively, different therapeutically effective doses of an antagonist anti-CD40 antibody or protein of the invention can be used over the course of a treatment period.

In some embodiments, the initial therapeutically effective dose of an antagonist anti-CD40 antibody or antigen-binding fragment thereof as defined elsewhere herein can be in the lower dosing range (i.e., 0.003 mg/kg to 20 mg/kg) with subsequent doses falling within the higher dosing range (i.e., from 20 mg/kg to 50 mg/kg).

In alternative embodiments, the initial therapeutically effective dose of an antagonist anti-CD40 antibody or antigen-binding fragment thereof as defined elsewhere herein can be in the upper dosing range (i.e., 20 mg/kg to 50 mg/kg) with subsequent doses falling within the lower dosing range (i.e., 0.003 mg/kg to 20 mg/kg). Thus, in one embodiment, the initial therapeutically effective dose of the antagonist anti-CD40 antibody or antigen-binding fragment thereof is 20 mg/kg to 35 mg/kg, including about 20 mg/kg, about 25 mg/kg, about 30 mg/kg, and about 35 mg/kg, and subsequent therapeutically effective doses of the antagonist anti-CD40 antibody or protein of the invention are about 5 mg/kg to about 15 mg/kg, including about 5 mg/kg, 8 mg/kg, 10 mg/kg, 12 mg/kg, and about 15 mg/kg.

In some embodiments of the invention, anti-CD40 therapy is initiated by administering a "loading dose" of the antibody or protein of the invention to the subject in need of anti-CD40 therapy. By "loading dose" is intended an initial dose of the anti-CD40 antibody or protein of the invention that is administered to the subject, where the dose of the antibody or protein of the invention administered falls within the higher dosing range (i.e., from about 20 mg/kg to about 50 mg/kg). The "loading dose" can be administered as a single administration, for example, a single infusion where the antibody or antigen-binding fragment thereof is administered IV, or as multiple administrations, for example, multiple infusions where the antibody or antigen-binding fragment thereof is administered IV, so long as the complete "loading dose" is administered within about a 24-hour period. Following administration of the "loading dose", the subject is then administered one or more additional therapeutically effective doses of the anti-CD40 antibody or protein of the invention. Subsequent therapeutically effective doses can be administered, for example, according to a weekly dosing schedule, or once every two weeks, once every three weeks, or once every four weeks. In such embodiments, the subsequent therapeutically effective doses generally fall within the lower dosing range (i.e. 0.003 mg/kg to 20 mg/kg).

Alternatively, in some embodiments, following the "loading dose", the subsequent therapeutically effective doses of the anti-CD40 antibody or protein of the invention are administered according to a "maintenance schedule", wherein the therapeutically effective dose of the antibody or protein of the invention is administered once a month, once every 6 weeks, once every two months, once every 10 weeks, once every three months, once every 14 weeks, once every four months, once every 18 weeks, once every five months, once every 22 weeks, once every six months, once every 7 months, once every 8 months, once every 9 months, once every 10 months, once every 11 months, or once every 12 months. In such embodiments, the therapeutically effective doses of the anti-CD40 antibody or protein of the invention fall within the lower dosing range (i.e., 0.003 mg/kg to about 20 mg/kg), particularly when the subsequent doses are administered at more frequent intervals, for example, once every two weeks to once every month, or within the higher dosing range (i.e., from 20 mg/kg to 50 mg/kg), particularly when the subsequent doses are administered at less frequent intervals, for example, where subsequent doses are administered one month to 12 months apart.

Any pharmaceutical composition comprising an anti-CD40 antibody or protein of the invention having the desired functional properties described herein as the therapeutically active component can be used in the methods of the invention. Thus liquid, lyophilized, or spray-dried compositions comprising one or more of the anti-CD40 antibodies or proteins of the invention, for example, mAb1, mAb2 or mAb3 antibodies, may be prepared as an aqueous or non-aqueous solution or suspension for subsequent administration to a subject in accordance with the methods of the invention.

Each of these compositions will comprise at least one of the anti-CD40 antibodies or proteins of the present invention as a therapeutically or prophylactically active component.

By "therapeutically or prophylactically active component" is intended the anti-CD40 antibody or protein of the invention is specifically incorporated into the composition to bring about a desired therapeutic or prophylactic response with regard to treatment, prevention, or diagnosis of a disease or condition within a subject when the pharmaceutical composition is administered to that subject. Preferably the pharmaceutical compositions comprise appropriate stabilizing agents, bulking agents, or both to minimize problems associated with loss of protein stability and biological activity during preparation and storage.

Formulants may be added to pharmaceutical compositions comprising an anti-CD40 antibody or protein of the invention. These formulant may include, but are not limited to, oils, polymers, vitamins, carbohydrates, amine acids, salts, buffers, albumin, surfactants, or bulking agents. Preferably carbohydrates include sugar or sugar alcohols such as mono-, di-, or polysaccharides, or water soluble glucans. The saccharides or glucans can include fructose, glucose, mannose, sorbose, xylose, maltose, sucrose, dextran, pullulan, dextrin, α- and β-cyclodextrin, soluble starch, hydroxyethyl starch, and carboxymethylcellulose, or mixtures thereof.

"Sugar alcohol" is defined as a $C_4$ to $C_8$ hydrocarbon having a hydroxyl group and includes galactitol, inositol, mannitol, xylitol, sorbitol, glycerol, and arabitol. These sugars or sugar alcohols may be used individually or in combination. The sugar or sugar alcohol concentration may be between 1.0% and 7% w/v, more preferably between 2.0% and 6.0% w/v. For example, amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. Surfactants that can be added to the formulation are shown in EP Nos. 270,799 and 268,110.

Additionally, antibodies can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546. Preferred polymers are polyoxyethylated polyols and polyethylene glycol (PEG). PEG is soluble in water at room temperature and has the ageneral formula: R (O—CH2-CH2) n O—R where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1,000 and 40,000, more preferably between 2,000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention.

They include polyoxyethylated sorbitol, polyoxyethylated glucose, polyoxyethylated glycerol (POG), and the like. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al. (1988, J. Bio. Chem. 263: 15064-15070) and a discussion of POG/IL-2 conjugates is found in U.S. Pat. No. 4,766,106.

Another drug delivery system for increasing circulatory half-life is the liposome.

Methods of preparing liposome delivery systems are discussed in Gabizon et al. (1982) Cancer Research 42: 4734; Cafiso (1981) Biochem Biophys Acta 649: 129; and Szoka (1980) Ann. Rev. Bioplays. Eng. 9: 467. Other drug delivery systems are known in the art and are described in, e.g., Poznansky et al. (1980) Drug Delivery Systems (R. L. Juliano, ed., Oxford, N.Y.) pp. 253-315; Poznansky (1984) Pharm Revs 36: 277.

The formulant to be incorporated into a pharmaceutical composition should provide for the stability of the antagonist anti-CD40 antibody or protein of the invention. That is, the anti-CD40 antibody or protein of the invention should retain its physical and/or chemical stability and have the desired functional properties, i.e., one or more of the desired functional properties defined herein above.

Methods for monitoring protein stability are well known in the art. See, for example, Jones (1993) Adv. Drug Delivery Rev. 10: 29-90; Lee, ed. (1991) Peptide and Protein Drug Delivery (Marcel Dekker, Inc., New York, N.Y.); and the stability assays disclosed herein below. Generally, protein stability is measured at a chosen temperature for a specified period of time. In preferred embodiments, a stable antibody pharmaceutical formulation provides for stability of the antagonist anti-CD40 antibody or protein of the invention when stored at room temperature (about 25° C.) for at least 1 month, at least 3 months, or at least 6 months, and/or is stable at about 2-8 C for at least 6 months, at least 9 months, at least 12 months, at least 18 months, at least 24 months.

A protein such as an antibody, when formulated in a pharmaceutical composition, is considered to retain its physical stability at a given point in time if it shows no visual signs (i.e., discoloration or loss of clarity) or measurable signs (for example, using size-exclusion chromatography (SEC) or UV light scattering) of precipitation, aggregation, and/or denaturation in that pharmaceutical composition. With respect to chemical stability, a protein such as an antibody, when formulated in a pharmaceutical composition, is considered to retain its chemical stability at a given point in time if measurements of chemical stability are indicative that the protein (i.e., antibody) retains the biological activity of interest in that pharmaceutical composition. Methods for monitoring changes in chemical stability are well known in the art and include, but are not limited to, methods to detect chemically altered forms of the protein such as result from clipping, using, for example, SDS-PAGE, SEC, and/or matrix-assisted laser desorption ionization/time of flight mass spectrometry; and degradation associated with changes in molecular charge (for example, associated with deamidation), using, for example, ion-exchange chromatography. See, for example, the methods disclosed herein below.

An anti-CD40 antibody or protein of the invention, when formulated in a pharmaceutical composition, is considered to retain a desired biological activity at a given point in time if the desired biological activity at that time is within about 30%, preferably within about 20% of the desired biological activity exhibited at the time the pharmaceutical composition was prepared as determined in a suitable assay for the desired biological activity. Assays for measuring the desired biological activity of the antagonist anti-CD40 antibodies or proteins disclosed herein, can be performed as described in the Examples herein. See also the assays described in Schutze et al. (1998) Proc. Natl. Acad. Sci. USA 92: 8200-8204; Denton et al. (1998) Pediatr Transplant. 2: 6-15; Evans et al. (2000) J: Immunol. 164: 688-697; Noelle (1998) Agents Actions Suppl. 49: 17-22; Lederman et al. (1996) Curr Opin. Hematol. 3: 77-86; Coligan et al. (1991) Current Protocols in Immunology 13: 12; Kwekkeboom et al. (1993) Immunology 79: 439-444; and U.S. Pat. Nos. 5,674,492 and 5,847,082.

In some embodiments of the invention, the anti-CD40 antibody, for example, selected among mAb1-mAb3 recombinant antibodies, is formulated in a liquid pharmaceutical formulation. The anti-CD40 antibody or protein of the invention can be prepared using any method known in the art, including those methods disclosed herein above. In one embodiment, the anti-CD40 antibody, for example, selected among the mAb1-mAb3 antibodies, is recombinantly produced in a CHO cell line.

Following its preparation and purification, the anti-CD40 antibody can be formulated as a liquid pharmaceutical formulation in the manner set forth herein. Where the antagonist anti-CD40 antibody is to be stored prior to its formulation, it can be frozen, for example, at −20° C., and then thawed at room temperature for further formulation.

The liquid pharmaceutical formulation comprises a therapeutically effective amount of the anti-CD40 antibody or protein of the invention, for example, mAb1, mAb2 or mAb3 antibody. The amount of antibody present in the formulation takes into consideration the route of administration and desired dose volume.

In this manner, the liquid pharmaceutical composition comprises the anti-CD40 antibody, for example, mAb1, mAb2 or mAb3 antibody, at a concentration of 0.1 mg/ml to 300.0 mg/ml, 1.0 mg/ml to 200 mg/ml, 5.0 mg/ml to 100.0 mg/ml, 7.5 mg/ml to 50 mg/ml, or 15.0 mg/ml to 25.0 mg/ml.

The liquid pharmaceutical composition comprises the anti-CD40 antibody, for example, mAb1, mAb2 or mAb3 antibody and a buffer that maintains the pH of the formulation in the range of pH 5.0 to pH 7.0.

Any suitable buffer that maintains the pH of the liquid anti-CD40 antibody formulation in the range of about pH 5.0 to about pH 7.0 can be used in the formulation, so long as the physicochemical stability and desired biological activity of the antibody are retained as noted herein above. Suitable buffers include, but are not limited to, conventional acids and salts thereof, where the counter ion can be, for example, sodium, potassium, ammonium, calcium, or magnesium. Examples of conventional acids and salts thereof that can be used to buffer the pharmaceutical liquid formulation include, but are not limited to, succinic acid or succinate, histidine or histidine hydrochloride, citric acid or citrate, acetic acid or acetate, tartaric acid or tartarate, phosphoric acid or phosphate, gluconic acid or gluconate, glutamic acid or glutamate, aspartic acid or aspartate, maleic acid or maleate, and malic acid or malate buffers. The buffer concentration within the formulation can be from 1 mM to 50 mM, including about 1 mM, 2 mM, 5 mM, 8 mM, 10 mM, 15 mM, 20 mM, 25 mM, 30 mM, 35 mM, 40 mM, 45 mM, 50 mM, or other such values within the range of 1 mM to 50 mM.

In some embodiments of the invention, the liquid pharmaceutical formulation comprises a therapeutically effective amount of the anti-CD40 antibody, for example, the mAb1, mAb2 or mAb3 antibody, and succinate buffer or citrate buffer or histidine buffer or histidine hydrochloride buffer at a concentration that maintains the pH of the formulation in the range of about pH 5.0 to pH 7.0. By "succinate buffer" or "citrate buffer" is intended a buffer comprising a salt of succinic acid or a salt of citric acid, respectively. By "histidine buffer" is intended a buffer comprising a salt of the amino acid histidine.

In a preferred embodiment, the buffer is a histidine buffer, e.g., histidine hydrochloride. As noted above, the histidine buffer concentration within the formulation can be from 1 mM to 50 mM, including about 1 mM, 2 mM, 5 mM, 8 mM, 10 mM, 15 mM, 20 mM, 25 mM, 30 mM, 35 mM, 40 mM, 45 mM, 50 mM, or other such values within the range of 1 mM to 50 mM.

In a preferred embodiment, the succinate or citrate counterion is the sodium cation, and thus the buffer is sodium succinate or sodium citrate, respectively. However, any cation is expected to be effective. Other possible succinate or citrate cations include, but are not limited to, potassium, ammonium, calcium, and magnesium. As noted above, the succinate or citrate buffer concentration within the formulation can be from 1 mM to 50 mM, including about 1 mM, 2 mM, 5 mM, 8 mM, 10 mM, 15 mM, 20 mM, 25 mM, 30 mM, 35 mM, 40 mM, 45 mM, 50 mM, or other such values within the range of 1 mM to 50 mM.

In other embodiments, the liquid pharmaceutical formulation comprises the antagonist anti-CD40 antibody, for example, the mAb1, mAb2 or mAb3 antibody, at a concentration of 0.1 mg/ml to 300.0 mg/ml, or 1.0 mg/ml to 200 mg/ml, 5.0 mg/ml to 100.0 mg/ml, 7.5 mg/ml to 50 mg/ml, or 15.0 mg/ml to 25.0 mg/ml, and histidine or succinate or citrate buffer, for example, sodium succinate or sodium citrate buffer or histidine hydrochloride, at a concentration of 1 mM to 50 mM, 5 mM to 40 mM, 10 mM to 35 mM, preferably about 30 mM.

Where it is desirable for the liquid pharmaceutical formulation to be near isotonic, the liquid pharmaceutical formulation comprising a therapeutically effective amount of the anti-CD40 antibody or protein of the invention, for example, the mAb1, mAb2 or mAb3 antibody, and a buffer to maintain the pH of the formulation within the range of about pH 5.0 to about pH 7.0 can further comprise an amount of an isotonizing agent sufficient to render the formulation near isotonic. By "near isotonic" is intended the aqueous formulation has an osmolarity of 240 mmol/kg to 800 mmol/kg, preferably about 240 to about 600 mmol/kg, more preferably about 240 to about 440 mmol/kg, more preferably about 250 to about 330 mmol/kg, even more preferably about 260 to about 320 mmol/kg, still more preferably about 270 to about 310 mmol/kg.

Methods of determining the isotonicity of a solution are known to those skilled in the art. See, for example, Setnikar et al. (1959) J. Am. Pharm. Assoc. 48:628. Those skilled in the art are familiar with a variety of pharmaceutically acceptable solutes useful in providing isotonicity in pharmaceutical compositions. The isotonizing agent can be any reagent capable of adjusting the osmotic pressure of the liquid pharmaceutical formulation of the present invention to a value nearly equal to that of a body fluid. It is desirable to use a physiologically acceptable isotonizing agent.

Thus, the liquid pharmaceutical formulation comprising a therapeutically effective amount of the antagonist anti-CD40 antibody, for example, the mAb1, mAb2 or mAb3 antibody and a buffer to maintain the pH of the formulation within the range of about pH 5.0 to about pH 7.0, can further comprise components that can be used to provide isotonicity, for example, sodium chloride; amino acids such as alanine, valine, and glycine; sugars and sugar alcohols (polyols), including, but not limited to, glucose, dextrose, fructose, sucrose, maltose, mannitol, trehalose, glycerol, sorbitol, and xylitol; acetic acid, other organic acids or their salts, and relatively minor amounts of citrates or phosphates. The ordinary skilled person would know of additional agents that are suitable for providing optimal tonicity of the liquid formulation.

In some preferred embodiments, the liquid pharmaceutical formulation comprising a therapeutically effective amount of the anti-CD40 antibody, for example, the mAb1, mAb2 or mAb3 antibody, and a buffer to maintain the pH of the formulation within the range of about pH 5.0 to about pH 7.0, further comprises sodium chloride as the isotonizing agent.

The concentration of sodium chloride in the formulation will depend upon the contribution of other components to tonicity. In some embodiments, the concentration of sodium chloride is 50 mM to 300 mM. In one such embodiment, the concentration of sodium chloride is about 150 mM. In other such embodiments, the concentration of sodium chloride is about 150 mM, the buffer is sodium succinate or sodium citrate buffer at a concentration of 5 mM to 15 mM, the liquid pharmaceutical formulation comprises a therapeutically effective amount of the anti-CD40 antibody or protein of the invention, for example, the mAb1, mAb2 or mAb3 antibody, and the formulation has a pH of 5.0 to pH 7.0.

In other embodiments, the liquid pharmaceutical formulation comprises the anti-CD40 antibody or protein of the invention, for example, mAb1, mAb2 or mAb3 antibody, at a concentration of 0.1 mg/ml to 50.0 mg/ml or 5.0 mg/ml to 25.0 mg/ml, about 150 mM sodium chloride, and about 10 mM, 20 mM 30 mM, 40 mM or 50 mM sodium succinate or sodium citrate, at a pH of about pH 5.5.

Protein degradation due to freeze thawing or mechanical shearing during processing of a liquid pharmaceutical formulation of the present invention can be inhibited by incorporation of surfactants into the formulation in order to lower the surface tension at the solution-air interface. Thus, in some embodiments, the liquid pharmaceutical formulation comprises a therapeutically effective amount of the anti-CD40 antibody or protein of the invention, for example, the mAb1, mAb2 or mAb3 antibody, a buffer to maintain the pH of the formulation within the range of about pH 5.0 to about pH 7.0, and further comprises a surfactant. In other embodiments, the liquid pharmaceutical formulation comprises a therapeutically effective amount of the anti-CD40 antibody or protein of the invention, for example, the mAb1, mAb2 or mAb3 antibody, a buffer to maintain the pH of the formulation within the range of about pH 5.0 to about pH 7.0, an isotonizing agent such as sodium chloride at a concentration of about 50 mM to about 300 mM, and further comprises a surfactant.

Typical surfactants employed are nonionic surfactants, including polyoxyethylene sorbitol esters such as polysorbate 80 (TWEEN® 80) and polysorbate 20 (TWEEN® 20); polyoxypropylene-polyoxyethylene esters such as PLURIONIC® F68; polyoxyethylene alcohols such as BRIJ® 35; simethicone; polyethylene glycol such as PEG400; lysophosphatidylcholine; and polyoxyethylene-p-t-octylphenol such as TRITON® X-100.

Classic stabilization of pharmaceuticals by surfactants or emulsifiers is described, for example, in Levine et al. (1991) J. Parenteral Sci. Technol. 45 (3): 160-165, herein incorporated by reference. A preferred surfactant employed in the practice of the present invention is polysorbate 80. Where a surfactant is included, it is typically added in an amount from 0.001% to 1.0% (w/v).

Thus, in some embodiments, the liquid pharmaceutical formulation comprises a therapeutically effective amount of the anti-CD40 antibody or protein of the invention, for example, the mAb1, mAb2 or mAb3 antibody, the buffer is sodium succinate or sodium citrate or histidine buffer or histidine hydrochloride buffer at a concentration of 1 mM to 50 mM, 3 mM to 40 mM, or 5 mM to 35 mM; or 7.5 mM to 30 mM; the formulation has a pH of pH 5.0 to pH 7.0; and the formulation further comprises a surfactant, for example, polysorbate 80, in an amount from 0.001% to 1.0% or 0.001% to 0.5%. Such formulations can optionally comprise an isotonizing agent, such as sodium chloride at a concentration of 50 mM to 300 mM, 50 mM to 200 mM, or 50 mM to 150 mM.

In other embodiments, the liquid pharmaceutical formulation comprises the anti-CD40 antibody or protein of the invention, for example, the mAb1, mAb2 or mAb3 antibody, at a concentration of 0.1 mg/ml to 200.0 mg/ml or 1 mg/ml to 100.0 mg/ml or 2 mg/ml to 50.0 mg/ml or 5.0 mg/ml to 25.0 mg/ml, including about 20.0 mg/ml; 50 mM to 200 mM sodium chloride, including about 150 mM sodium chloride; sodium succinate or sodium citrate at 5 mM to 20 mM, including about 10 mM sodium succinate or sodium citrate; sodium chloride at a concentration of 50 mM to 200 mM, including about 150 mM; histidine or histidine chloride at 5 mM to 50 mM, including about 30 mM histidine or histidine chloride; and optionally a surfactant, for example, polysorbate 80, in an amount from 0.001% to 1.0%, including 0.001% to 0.5%; where the liquid pharmaceutical formulation has a pH of about pH 5.0 to about pH 7.0.

The liquid pharmaceutical formulation can be essentially free of any preservatives and other carriers, excipients, or stabilizers noted herein above. Alternatively, the formulation can include one or more preservatives, for example, antibacterial agents, pharmaceutically acceptable carriers, excipients, or stabilizers described herein above provided they do not adversely affect the physicochemical stability of the antagonist anti-CD40 antibody or antigen-binding fragment thereof. Examples of acceptable carriers, excipients, and stabilizers include, but are not limited to, additional buffering agents, co-solvents, surfactants, antioxidants including ascorbic acid and methionine, chelating agents such as EDTA, metal complexes (for example, Zn-protein complexes), and biodegradable polymers such as polyesters. A thorough discussion of formulation and selection of pharmaceutically acceptable carriers, stabilizers, and isomolytes can be found in Remington's Pharmaceutical Sciences (18th ed.; Mack Publishing Company, Eaton, Pa., 1990).

After the liquid pharmaceutical formulation or other pharmaceutical composition described herein is prepared, it can be lyophilized to prevent degradation. Methods for lyophilizing liquid compositions are known to those of ordinary skill in the art. Just prior to use, the composition may be reconstituted with a sterile diluent (Ringers solution, distilled water, or sterile saline, for example) that may include additional ingredients.

Upon reconstitution, the composition is preferably administered to subjects using those methods that are known to those skilled in the art.

Use of Antagonist Anti-CD40 Antibodies in the Manufacture of Medicaments

The present invention also provides an antagonist anti-CD40 antibody or proteins of the invention for use in treating an autoimmune disease and/or inflammatory disease in a subject, wherein the medicament is coordinated with treatment with at least one other therapy.

By "coordinated" is intended the medicament is to be used either prior to, during, or after treatment of the subject with at least one other therapy. Examples of other therapies include, but are not limited to, those described herein above, i.e., surgery or surgical procedures (e.g. splenectomy, lymphadenectomy, thyroidectomy, plasmaphoresis, leukophoresis, cell, tissue, or organ transplantation, organ perfusion, intestinal procedures, and the like), radiation therapy, therapy such as steroid therapy and non-steroid therapy, hormone therapy, cytokine therapy, therapy with dermatological agents (for example, topical agents used to treat skin conditions such as allergies, contact dermatitis, and psoriasis), immunosuppressive therapy, and other anti-inflammatory monoclonal antibody therapy, and the like, where treatment with the additional therapy, or additional therapies, occurs prior to, during, or subsequent to treatment of the subject with the medicament comprising the antagonist anti-CD40 antibody or proteins of the invention as noted herein above.

In one such embodiment, the present invention provides for mAb1, mAb2 or mAb3 antibody for use in the treatment of an autoimmune disease and/or inflammatory disease in a subject, wherein the medicament is coordinated with treatment with at least one other therapy as noted herein above.

In some embodiments, the medicament comprising the antagonist anti-CD40 antibody, for example, the monoclonal antibody mAb1, mAb2 or mAb3 disclosed herein, or antigen-binding fragment thereof is coordinated with treatment with two other therapies.

Where the medicament comprising the antagonist anti-CD40 antibody is coordinated with two other therapies, use of the medicament can be prior to, during, or after treatment of the subject with either or both of the other therapies.

The invention also provides for an antagonist anti-CD40 antibody, for example, the antibody mAb1, mAb2 or mAb3 disclosed herein, for use in treating an autoimmune disease and/or inflammatory disease in a subject, wherein the medicament is used in a subject that has been pretreated with at least one other therapy.

By "pretreated" or "pretreatment" is intended the subject has been treated with one or more other therapies prior to receiving the medicament comprising the antagonist anti-CD40 antibody or protein of the invention.

The following examples are offered by way of illustration and not by way of limitation.

FIGURE LEGENDS

EXAMPLES

Figure 1:
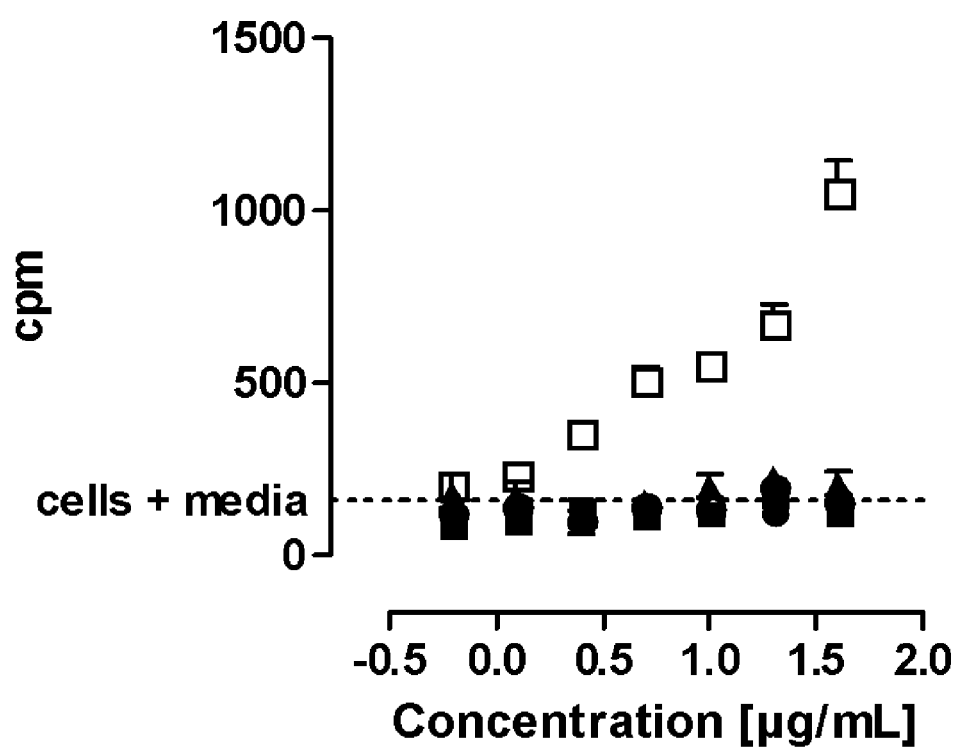
FIG. 1 shows incorporation of $^3$H-thymidine after 72 hours of human PBMC culture stimulated with a dose response of Chir12.12 (empty circle), mAb1 (filled circle), mAb2 (filled square), mAb3 (filled triangle) or human CD40L (empty square).

Materials
1. Monoclonal Antibodies

Chir12.12 (1.9 mg/ml), mAb1 (0.88 mg/ml), mAb2 (1.9 mg/ml), and mAb3 (1.9 mg/ml) were provided in 50 mM Citrate pH 7.0, 140 mM NaCl. An IgG isotype control was also used for select experiments (SIGMA-ALDRICH®, St. Louis, USA).

2. B Cell Activation Stimuli

AfiniPure F(ab')2 fragment rabbit anti-human IgM was obtained from Jackson Immuno Research (Suffolk, UK), and CpG2006 was obtained from MICROSYNTH™ (Balgach, Switzerland). Recombinant human CD40L was generated using standard procedures known to those of ordinary skill in the art. Supernatant containing human IL-4 was generated using standard procedures known to those of ordinary skill in the art.

3. In Vitro Tissue Culture Reagents

PBMC culture media: RPMI-1640, 10% FBS, 1% Penicillin/Streptomycin, 1% non-essential amino acids, 1% Sodium pyruvate, 5 mM β-mercaptoethanol (all from INVITROGEN™, San Diego, USA).

Methods
1. CD40L-Mediated PBMC Proliferation Assay
1.1 Purification of Human Peripheral Blood Mononuclear Cells (PBMCs)

Primary PBMCs were purified from whole blood buffy coats obtained from healthy volunteers (Blutspendezentrum, Basel). Buffy coats were diluted 1:4 with Ca2+ and Mg2+ free PBS containing 5 mM EDTA and 25 ml was aliquoted into 50 ml FALCON™ tubes. Diluted buffy coats were underlayed with 14 ml of FICOLL-PAQUE® PLUS(GE HEALTHCARE®) per FALCON™ tube and centrifuged at room temperature for 20 min at 2250 rpm (no brake). Following centrifugation, the interphase layer was transferred to a single 50 ml FALCON™ tube. Interphase layers from multiple tubes (from a single donor) were combined up to a volume of 30 ml. PBS supplemented with 5 mM EDTA was added and cells were spun at room temperature for 5 min at 2250 rpm. The supernatant was discarded prior to addition of 15 ml red blood cell (RBC) lysis buffer and incubation at room temperature for 5 min. Subsequently 20 ml of PBS/5 mM EDTA was added and cells were spun again (RT/5 min at 2250 rpm). Cells were washed twice in PBS/5 mM EDTA (with intervening centrifugation steps) and re-suspended in 35 ml PBMC media prior to viable cell number determination using Trypan Blue dye exclusion. Cells not used immediately for in vitro stimulation were cryopreserved.

1.2 In Vitro PBMC Stimulation Assay

Seven point two-fold dilution series of each anti-CD40 or isotype control mAb were made in triplicate in Costar 96 well plates in the presence or absence of a constant dose of 5 µg/ml anti-IgM F(ab')2, 1 µM CpG2006, supernatant containing human IL-4 (75 ng/ml), or 40 µg/ml recombinant huCD40L (final concentrations indicated). Starting concentrations of each anti-CD40 mAb ranged from 20 µg/ml to 100 µg/ml depending on the experiment. CD40L was used in dose response as a positive control for all experiments. Doses of anti-IgM, CpG2006, IL-4 and CD40L were selected based on prior experiments where the ability of these reagents (alone or in combination) to induce PBMC or B cell proliferation was assessed in dose response (data not shown). PBMCs (final density of $8 \times 10^4$ per well) were subsequently added to each well prior to incubation for 3 days at 37° C./5% $CO_2$. $^3$H-thymidine (1 µCi/50 µl/well) was added to each well for the final 6 hours of culture prior to harvesting and determination of thymidine incorporation using a MICROBETA® Trilux scintillation counter. Note that cells plus media and cells plus media plus anti-IgM, IL-4, CpG2006 or CD40L control cultures (in the absence of anti-CD40 mAbs) were included in each experiment.

Scintillation data was analyzed using EXCEL® and GRAPHPAD PRISM® software. Results are presented as mean counts per minute (cpm) (+/- standard error of the mean) versus a log transformation of the anti-CD40mAb concentration. Positive controls and cell plus media background levels are indicated on each graph. IC50 or EC50 values were calculated subject to successful curve-fitting of data by Prism.

PBMCs were stimulated as indicated above with 20 µg/ml CD40L in the presence or absence of a dose response of the test anti-CD40 mAb for 3 days. Proliferation was assessed by $^3$H-thymidine incorporation after 72 hours of culture. Results are presented as the mean of triplicate cultures with SEM and are representative of 4 donors (independent experiments). IC50 values for anti-CD40 mAb mediated inhibition are tabulated in µg/ml.

2. In Vitro PBMC Agonist Assay

Human PBMCs were stimulated as indicated in paragraph 1.2 above with a dose response of Chir12.12, mAb1, mAb2 or mAb3 for 3 days either in the absence of co-stimulation or in the presence of either 5 µg/ml anti-IgM F(ab')2 or 1 µM CpG2006. Proliferation was assessed by $^3$H-thymidine incorporation after 72 hours of culture. Results are presented as the mean of triplicate cultures with SEM and are representative of 4 donors (independent experiments).

3. ADCC Assay

50 µl of a PBMC suspension ($10 \times 10^6$ cells/mL) was added to round-bottom wells (CORNING® Incorporated—COSTAR® #3790), 50 µl calcein-stained RAJI® cells at ($2 \times 10^5$ cells/mL) and 100 µl of antibody dilution or controls were added. Maximum lysis was determined in 2% TRITON® 100.

Cells were collected at the bottom of the plate (3 minutes at 250 g) and incubated at 37° C. in humidified $CO_2$ atmosphere (5%) for 1 hour. Cells were separated from the medium by centrifugation (3 minutes at 750 g) and 100 µl of supernatant were transferred into a clear bottom black plate (CORNING® Incorporated—COSTAR® #3904) for measurement.

Fluorescence was determined at 535 nm after excitation at 485 nm with a SPECTRAMAX® GEMINI™ spectrometer (MOLECULAR DEVICES®). Specific lysis was calculated using the following formula:

(experimental release−spontaneous release)/(maximum release−spontaneous release)×100.

4. Binding of Anti-Human CD40 Antibody Variants to Human BJAB Cell Line

Flow cytometry was used, in order to compare the binding of the different anti-CD40 antibody Fc variants in their binding to human BJAB cells. Therefore, $2 \times 10^5$ cells were seeded per well in a 96-well V-bottom plate. The plates were washed twice with 200 µL of FACS buffer (PBS, 5% FCS, 2 mM EDTA) for 2 min at 4° C. at 1350×g. Supernatants were discarded and cells were resuspended in 100 mL FACS buffer containing 8 human serum (iINVITROMEX™, Cat. No. S4190) and incubated for 10 min. After two washes anti-human CD40 Fc variants were added in 50 µL FACS buffer with 1% human serum starting at a concentration of 10 µg/mL in a 1:2 dilution. Cells were incubated for 30 min on ice followed by two washing steps. 50 µL of polyclonal rabbit anti-human IgG FITC, F(ab')2 (DAKO®, Cat. No. F 0315) were added to each well and incubated for 30 min on ice. At the end of the incubation cells were washed twice, resuspended in 100 µL FACS buffer and acquired on a FACS Cantoll™.

After acquisition the mean fluorescence intensity of the FITC channel was acquired in FloJo™ Graphing and curve fitting was performed with GRAPHPAD PRISM® 5.0. Due to changing intensities between individual experiments, values were normalized. Therefore, the highest value of each antibody test series was equaled 100%. Non-linear curve fittings were performed with the percent values.

5. CD40L-Mediated Cytokine Production Assay in Monocyte-Derived Dendritic Cells (MoDCs)

5.1 Preparation of Human Monocyte-Derived Dendritic Cells

Human PBMCs were prepared from human buffy coats provided by the Swiss Red Cross. The buffy coat was diluted 1:5 in PBS (INVITROGEN™, Cat. No. 20012019) and distributed in 35 mL aliquots to 50 mL FALCON™ tubes. Subsequently, 13 mL of FICOLL® (GE HEALTHCARE®, Cat. No. 17 1440-02) were underlain in each tube. Cells were centrifuged at 1680×g at RT for 20 min without break. The PBMC containing layer was collected and washed twice in a large volume of PBS for 5 min at 1000×g. Finally cells were resuspended in 10 mL PBS and counted.

Human monocytes were negatively isolated from the $100 \times 10^7$ PBMCs using the human monocyte isolation kit II from MILTENYI BIOTECH™ (MILTENYI BIOTECH™, Germany, Cat. No. 130-091-153) on an AUTOMACS® instrument according to the manufacturer's instructions. After the isolation cells were washed twice for 5 min at 1000×g at 4° C. in culture medium (RPMI1640 (INVITROGEN™, Cat. No. 61870010), 10% FCS (INVITROGEN™, Cat. No. 16000044, US origin), 1 mM sodium pyruvate (INVITROGEN™, Cat. No. 11360039), 1×NEAA (INVITROGEN™, Cat. No. 11140035) 1× Penicillin/Streptomycin (INVITROGEN™, Cat. No. 15140122)). Isolated monocytes were counted, plated in 6 well plates at a density of $0.4 \times 10^6$/mL and cultured for seven days at 37° C., 5% CO2. To differentiate the monocytes to dendritic cells recombinant, human IL-4 [80 ng/mL] and human GM-CSF [100 ng/mL] (both produced in house) were added to the culture medium at the start of the culture.

5.2 Stimulation of Dendritic Cells (DCs) for Cytokine Release

Immature DCs were harvested after 7 days of culture by rinsing the 6 well plates, pooling the cells and washing them twice for 5 min at 1400×g in culture medium. Subsequently, 2×105 iDCs were seeded in 96-well flat-bottom plates (BD™, Cat. No. 353072) in 100 µL. For the positive control cells were stimulated with MegaCD40L™ (ALEXIS®, Cat. No. ALX-522-110-C010) at a concentration of 1 µg/mL, the negative control consisted of iDCs in medium only. In the antagonism assay anti-human CD40 antibody Fc variants were added at 10 µg/mL in a 1:2 dilution together with 1 µg/mL MegaCD40L™ for a dose-response. Supernatants of the stimulated cells were collected 24 h later for the measurement of TNFα. In the agonism assay anti-human CD40 antibody Fc variants were added at 10 µg/mL in a 1:2 dilution only and supernatants were collected after 48 h for the measurement of TNFα. Cells were seeded and stimulated in triplicates for all assays.

5.3 Measurement of TNF Alpha by ELISA

To measure the amount of TNFα in the supernatants, ELISA was performed as follows. Anti-TNFα capture antibody (BD™ Pharmingen, Cat. No. 551220) was coated on ELISA plates (GREINER™, NUNC® MAXISORP™ F96, Cat. No. 442404) at 5 µg/mL in 50 µL per well overnight at 4° C. For every washing step plates were washed 3× with 250 µL in a BIOTEK® ELx 405 plate washer. After the first wash, 200 µL of Superblock TBS (THERMO SCIENTIFIC®, PIERCE®, Cat. No. 37535) were incubated for 1 h at 37° C. Next, TNFα standard (recombinant human TNFα, R&D SYSTEMS®, Cat. No. 210-TA) or sample were added in 25 µl. The standard started at a final concentration of 20 ng/mL in a 1:2 dilution series. In addition, 25 µL of detection antibody (anti-human TNFα biotin, BD™ Pharmingen, Cat. No. 554511) was added in a 1:500 dilution. Plates were incubated overnight at 4° C. After washing, Avidin-POD conjugate (EXTRAVIDIN® alkaline phosphatase, SIGMA-ALDRICH®, Cat. No. E-2636) was diluted 1:5000 in Superblock TBS, added in 50 µL and incubated for 1 h at RT. Plates were washed and 50 µL of the substrate p-Nitrophenylphosphat (SIGMA-ALDRICH®, Cat. No. C-3041) was added to develop for 15 min. ELISA plates were read at 450 nm with the software SoftMax Pro on a SPECTRAMAX® M5 (MOLECULAR DEVICES®).

6. Toxicology Study

The primary initial purpose of the toxicology study was to investigate the potential toxicity of high dose (100 mg/kg) mAb1 in comparison to Chir12.12.

Thirty cynomolgus monkeys of Mauritian origin were used for this study. At the initiation of dosing, the animals were approximately 4 to 5 years of age and weighed 4.5 to 6.6 kg for the males and 3.1 to 4.3 kg for the females.

mAb1 (50 mg/mL) was administered intravenously to one group of cynomolgus monkeys (5 males/5 females; group 2) at a dose level of 100 mg/kg and a dose volume of 2 mL/kg once weekly for 5 weeks (test item applications on days 1, 8, 15, 22, 29, and 36). A further group of cynomolgus monkeys (5 males/5 females; group 3) received the parent antibody Chir12.12 intravenously by slow bolus infusion at a dose level of 100 mg/kg and a dose volume of 5 mL/kg. mAb1 placebo at a dose volume of 2 mL/kg was given to another group of cynomolgus monkeys which served as controls (5 males/5 females; group 1). All animals were subjected to necropsy one or two days after the last dosing.

It was decided to incorporate Keyhole Limpet Hemocyanin (KLH)-immunization in order to evaluate the efficacy of both anti-CD40 Abs. On day 2 animals were immunized with 1 mg KLH in Alum followed by a booster injection of 0.5 mg KLH in Alum on day 23. Serum was sampled pre-immunization/booster as well as on days 7 and 14 after immunization and booster, respectively. KLH specific IgM/IgG titers were determined with ELISA using cynomolgus monkey anti KLH IgM/IgG reference serum as standard. Blood was sampled on 3 pre-dose occasions and on day 15, 29 and at necropsy (day 37/38) for immunophenotyping of naive B cells (CD20+CD21+CD27−). Absolute naive CD20 B cell counts were calculated from the total lymphocyte count per blood sample and the relative naive CD20 B cell count by flow cytometry.

TABLE 4

Summary of toxicology study

| Group number | Group description | Dose level (mg/kg/dose) | Dose volume* (mL/kg) | Animals/group Male | Animals/group Female | Necropsy after 5 weeks |
|---|---|---|---|---|---|---|
| 1 | Control | 0 | 2 | 5 | 5 | 5 M/5 F |
| 2 | mAb1 | 100 | 2 | 5 | 5 | 5 M/5 F |
| 3 | Chir12.12 | 100 | 5 | 5 | 5 | 5 M/5 F |

*Based on most recent individual body weight

Assessment of toxicity was based on mortality, clinical observations (clinical signs including post-dosing observations, feces evaluation, fur inspection, and food consumption), body weights, ophthalmic examinations, cardiovascular investigations, clinical pathology (including coagulation, external platelet activation examinations, hematology, clinical chemistry and urine analysis), organ weights, and macroscopic and microscopic necropsy findings. Blood immunophenotyping was performed three times predose, on days 15 and 29 of the dosing phase as well as on the day of necropsy. Furthermore, immunophenotyping of spleen tissue and draining lymph nodes of the Keyhole Limpet Hemocyanin (KLH) injection site was performed at necropsy. In addition, the T-cell dependent antibody response (TDAR) to KLH was examined to directly compare the influence of the fully ADCC-capable Chir12.12 with the mAb1. Blood was collected from all animals for toxicokinetic evaluation and for a possible anti-drug-antibody (ADA) evaluation.

7. Additional In Vitro Profiling of mAb1

7.1 PBMC Purification

Human peripheral blood mononuclear cells were prepared as described previously in section 1.1.

7.2 Human Tonsil B Cell Purification

The tonsil capsule and connective tissue was removed and tonsil material after was cut the tonsil into ~5 mm big pieces prior to being mashed through a metal cell strainer with regular washing with B cell media. Tonsilar cells were then filtered twice through a 70 μM cell strainer in order to remove cellular debris. B cells were isolated from fresh PBMCs using an EASYSEP™ Negative Selection Human B cell Enrichment Kit (STEMCELL TECHNOLOGIES™, Vancouver, BC, Canada). B cells were purified using an EASYSEP™ Negative Selection Human B cell Enrichment Kit as per manufacturer's instructions (STEMCELL TECHNOLOGIES™, Vancouver, BC, Canada).

7.3 Assessment of CD40 Binding EC50 Values Using Human and Non-Human Primate PBMCs or B Cells PBMCs (rhesus, cynomolgus or human) or tonsil B cells (human only) were incubated at 4° C. for 30 min with purified labeled mAb1 or isotype control antibodies in dose response (final concentration range 2.5 μg/ml-0.00125 μg/ml). Cells were subsequently washed prior to being incubated with an anti-human (non-human primate cross-reactive) and a biotinylated anti-human IgG antibody with minimal cross-reactivity to NHPs (R10; note that it was possible to distinguish membrane IgG expressing human B cells either by including an anti-IgM stain or via differential intensity of FACS staining). Cells were again incubated at 4° C. for 30 min prior to being washed and subject to final staining with streptavidin-FITC for 20 min at 4° C. Cells were subsequently washed and evaluation of CD40 expression on CD20+ cells was performed by flow cytometry.

7.4 Assessment of the Inhibition of CD154-Induced Proliferation of Human and Non-Human Primate PBMCs or B Cells Seven point two-fold dilution series of each anti-CD40 or isotype control mAb were made in triplicate in 96 well plates in the presence of EC80 concentrations of human recombinant CD154 and IL-4. Starting concentrations of each anti-CD40 mAb ranged from 20 μg/ml to 100 μg/ml depending on the experiment. Cells and media controls were used as negative controls for all experiments. PBMCs (rhesus, cynomolgus or human) or tonsil B cells (human only) were subsequently added to each well prior to incubation for 3 days at 37° C./5% $CO_2$. $^3$H-thymidine (1 μCi/50 μl/well) was added to each well for the final 6 hours of culture prior to harvesting and determination of thymidine incorporation using a scintillation counter.

8. Efficacy of mAb1 Combined with Cyclosporine A in a Kidney Allo-Transplantation Model in Cynomolgus Monkey 8.1 Animals All the cynomolgus monkeys (*Macaca fascicularis*) used were 7.5-9 years old males (#5529/#5533, #5523/#5524 and #5536/#5538), captive-bred, 7.7±0.9 kg and originating from Philippines (SICONBREC™, Makati City, Philippines). At the time of transplantation, animals presented normal hematology, serum/urine chemistry and were negative for tuberculosis, *Salmonella/Shigella*, for antibodies against viral agents (HerpesB, Simian T-Cell Leukemia Virus, Simian immunodeficiency virus, simian type D retrovirus, Hepatitis B) and for relevant ecto/endoparasites. However, all animals presented antibodies against Cytomegalovirus and Hepatitis A virus (HAV) (tested in 2010; animal #5536 was negative for HAV). Coprology from animal #5523 was tested positive for *Balantidium coli* in December 2010.

During the first week post-surgery, animals where housed in single telemetry cages allowing visual contact with others. The rest of the time, animals #5536/#5538 were housed together and the 4 remaining animals were kept isolated during the whole experiment (incompatible animals). All animals were housed under maintained temperature (20-24° C.), at least 40% of humidity and natural light cycle. All were fed at least twice daily with mixture of fruits and vegetables. Water and KLIBA NAFAG™ 3446 pellets (Kaiseraugst, Germany) were provided ad libitum.

All experiments were performed according the Swiss Animal Welfare Regulations and under the license BS1555.

TABLE 5

Animal characteristics

| Species | Strain | Category | Vendor | Gender | Weight | Age |
|---|---|---|---|---|---|---|
| Cynomolgus (*Macaca fascicularis*) | any strain | not specified | BioPRIM | M/F | 7.7 ± 0.9 | 7.5-9 |

8.2 Experimental Conditions 8.2.1 Kidney Transplantation and Postoperative Monitoring Donor/recipient pairs were selected according to ABO match, DRB exon2 mismatch (Blancher A, Tisseyre P, Dutaur M, et al. (2006) Immunogenetics; 58(4):269-82) and responses in one-way Mixed lymphocyte reaction (MLR), having MLR-stimulation indices (MLR-SIs) >7 and <47 (Bigaud M, Maurer C, Vedrine, et al. (2004) J. Pharmacol. Toxicol. Methods; 50(2):153-9). The results of this selection are shown in Table 6 and consisted in duo-transplant (swap transplant between 2 donors). Each recipient was implanted with a telemetric probe (DATA SCIENCES INTERNATIONAL™, USA) for monitoring arterial blood pressure, heart rate and motor activity.

For surgery, general anesthesia was induced by ketamine; 10 mg/kg, intramuscularly, (i.m.) associated with atropine (0.05 mg/kg i.m.) and maintained by ventilation with $N_2O/O_2$ (50:50) and propofol intravenously (i.v.) (4-10 mg/kg/h; supplemented by 5-10 mg bolus whenever required). Donor kidneys were harvested, flushed with cold (4° C.) University of Wisconsin solution (cold preservation time≤4 hours) and transplanted heterotopically, using standard microvascular techniques to create an end-to-side anastomosis between the graft renal vein and the recipient vena cava and between the graft renal artery and the recipient distal aorta (anastomosis time≤40 minutes). An uretero-cystoneostomy was performed upon appearance of urine from the graft. The native kidneys were removed. Post-operative analgesia was provided by buprenorphine, 0.01-0.02 mg/kg, i.m., three times daily); antibiotics (cefotaxime, 25 mg/kg, i.m., twice daily or ceftriaxon, 50 mg/kg, i.m. in 1% lidocaine, four times daily). Analgesia and antibiotics were provided during 5 days. Whenever platelet counts experienced a marked increased or decreased, aspirin was administered at dose of 5 mg/kg i.m. daily (Aspegic, Sanofi-Aventis, Meyrin, Switzerland).

Recipients were monitored for changes in clinical and cardiovascular conditions, body weight, food and water intake (supplemented to max. 100-150 ml/kg/day), urine output, hematology (using BECKMAN COULTER® ACT5Diff), serum and urine chemistry (using a VETSCAN™ analyzer for daily SCrea/SUrea/SAmylase determination and a BECKMAN SYNCHRON CX5™ analyzer for final confirmation of serum and urine samples). Serum creatinine (SCrea) and urea (SUrea) levels were used as markers of graft function. Transcutaneous ultrasound-guided biopsies were performed with a 16G needle, as described previously (Gaschen L, Kunkler A, Menninger K, et al. (2001) Vet. Radiol. Ultrasound; 42(3):259-64), under general anesthesia on day 30 (animals #5529 and #5533, only). In addition, special monitoring for blood coagulability and platelet aggregation was also performed in animals #5529/#5533 and #5523/#5524 before and after transplant.

Recipients were ultimately euthanized in case of (i) severe graft failure (e.g. Screa>500 μmol/l or Surea>20 mmol/l) associated or not with increased ultrasound score; or (ii) general health problems and/or overt clinical signs of distress. At necropsy, the kidney allografts were collected (including ureter and anastomosis), together with all other major organs, and processed for subsequent histological analysis.

TABLE 6

General information about the donor/recipient combinations and treatment regimens used

| Recipient | Body weight (kg) | Donor | ABO | MLR-SI (one way) | mAb1/CsA (mg/kg, i.v./p.o.) | Transplant-date |
|---|---|---|---|---|---|---|
| 5529 ♂ | 7.35 | 5533 ♂ | B/B | 16 | 30/20 | 21.09.10 |
| 5533 ♂ | 6.1 | 5529 ♂ | B/B | 9 | 30/20 | 21.09.10 |
| 5523 ♂ | 8.2 | 5524 ♂ | B/B | 7 | 30/20 | 18.01.11 |
| 5524 ♂ | 8.3 | 5523 ♂ | B/B | 18 | 30/20 | 18.01.11 |
| 5536 ♂ | 8 | 5538 ♂ | B/B | 47 | 30/20 | 07.06.11 |
| 5538 ♂ | 8.45 | 5536 ♂ | B/B | 11 | 30/20 | 07.06.11 |

8.2.2 mAb1 and Cyclosporine A (CsA) Treatments mAb1 was provided in liquid form being freshly thawed on the day of infusion from −80° C. The application of 30 mg/kg/i.v. was done once weekly, excepting for the first three doses on day −1, 0 and 1 (pre- and post-transplant). CsA for oral administration (p.o.) was a microemulsion preconcentrate (SANDIMMUNE®, NEORAL® drink solution, 100 mg/ml, NOVARTIS™ Pharma AG). CsA was applied at a daily dose (starting on day −1) of 20 mg/kg/p.o., in combination with mAb1 (see Table 6).

8.2.3 Monitoring of mAb1 Pharmacokinetics (PK), Immunogenicity (Primate Anti-Human Antibody) and Pharmacodynamics (PD)

Blood samples (500 μl serum) were collected (prior to i.v. dosing) for the determination of mAb1 exposures at day −1, 3, 7 (baseline and 15 min), 14, 28, 42, 56, 70, 84 and 100. For CsA determinations, blood samples were collected before oral dosing or CsA (C0/C24) and 2 hours after the application (C2). C2 corresponds to the peak levels of CsA absorption. All the material was stored at −80° C. until further processing (CsA detection kit, HOTSTARTAQ® Master Mix, QIAGEN® Minnesota, US). Samples for mAb1-immunogenicity were collected (50 μl serum) on days −1, 7, 14, 28, 42, 56, 70, 84 and 100 in kept frozen −80° C. Briefly, ninety-six well microtiter plates were coated with recombinant human CD40. These were stored at 4° C. nominal overnight. Following blocking, Calibrator standards (Cs), Quality Control (QC) samples and sample specimens containing mAb1 were added to the plate. The plate was incubated at +25° C. nominal for 120 minutes with agitation. Following washing of the plate, mouse anti human kappa light chain antibody followed by HRP goat anti mouse (H+L) conjugate was added to the plate to detect any mAb1 bound to the recombinant CD40. This was visualized by the addition of a chromogenic substrate (TMB) and the intensity of the colour produced (absorbance) was directly proportional to the concentration of mAb1 present. The concentration of mAb1 in samples was then back-calculated from a calibration curve. PD samples were obtained on 2-3 days before transplant as baselines (0.5 ml in heparin). Afterwards the collection followed the same scheduled as for PK samples. CD20+ and CD3+ cells were counted with Tru-Count Tubes (BD™, cat #340334) used according to the manufacturer's instructions with an anti-human CD40-APC mAb (Clone 5C3, BD™, cat #555591), an anti-human CD3-PerCP (Clone SP34-2, BD™, cat #552851) and of anti-human CD20-FITC mAb (Clone LT20, IMMUNOTOOLS™, cat #21279203X2). Data was acquired on an LSRII flow cytometer (BD™ Biosciences) using FACSDIVA™ (version 6.1.1) software. Lymphocytes and beads were gated in the FSC/SSC dot blot according to size and granularity and further analyzed for expression of CD20 and CD3.

8.2.4 Histology

All collected tissues (graft biopsies or at necropsy) were examined macroscopically and fixed in 4% buffered formalin. After dehydration, they were embedded in paraffin wax. Three μm-thick sections were cut from paraffin blocks and stained with Hematoxylin and eosin (HE). Three additional stainings (Periodic acid Schiff, trichrome, and Verhoeff) were performed on kidney sections. The biopsy and necropsy samples were examined by an experienced pathologist and scored according to the Banff 07 classification of renal allograft pathology (Solez K, Colvin R B, Racusen L C, et al (2008) Am. J. Transplant; 8(4):753-60). Peer review was also performed by external experts.

In addition, immunohistochemistry for the complement protein C4d was performed using a polyvalent anti-C4d antibody suitable for staining paraffin sections (Regele H, Exner M, Watschinger B, et al. 2001, Nephrol. Dial. Transplant; 16: 2058-2066). C4b is considered a stable and reliable marker of acute humoral rejection (AHR). After fixation and paraffin wax embedding, glass slides (SUPERFROST® Plus, Menzel-Glaeser, Germany) with 3 μm-thick sections were prepared and dried overnight in an oven at 37° C. for optimal adhesion to the slides. Human rejected kidney sections were added as a positive control. Before use the slides were deparaffinized in Xylene (10 min), rehydrated through graded ethanol and placed in distilled water. Antigen retrieval was carried out by pressure-cooking for 10 min at 1 bar in citrate-buffer (pH 6.0) as previously described (Segerer S, Mack M, Regele H, Kerjaschki D, Schlondorff D. Kidney Int. 1999; 56: 52-64). For immunostaining, the following procedure was used: (i) inactivate endogenous peroxidase with 0.5% H2O2 in absolute methanol for 20 min at room temperature; (ii) wash slides in 0.01M PBS, pH 7.4 (SIGMA-ALDRICH® Chemie GmbH, Germany); (iii) incubate slides with 4% fat free powdered milk "Rapilait" in PBS, (MIGROS™ Genossenschaftsbund, Switzerland) for 60 min at room temperature; tap off, do not wash; (iv) incubate one slide with pAb rabbit anti-human C4d (BIO-MEDICA® Medizinprodukte, Vienna, Austria) 1:40 in PBS containing 1% NGtS overnight at +4° C. The second slide serves as negative control by applying rabbit isotype control (ZYMED® Laboratories Inc, USA) instead of primary antibody; (v) wash slides in 0.01M PBS, pH 7.4; (vi) incubate all slides with biotinylated goat anti-rabbit IgG (VECTOR LABORATORIES™, Inc. USA) 1:200 in PBS containing 1% NGtS for 30 min at room temperature; (vii) wash slides in 0.01M PBS, pH 7.4; (viii) incubate with Streptavidin/HRP (VECTOR LABORATORIES™, Inc. USA) in PBS for 30 min at room temperature, (ix) development of HRP activity with AEC+ (DAKOCYTOMATION™ Corp., Carpenteria, USA) for 8-10 min, control staining intensity microscopically, wash in distilled water, (x) counterstain with DAKO® Automation Hematoxylin (DAKOCYTO- MATION™ Corp., Carpenteria, USA) for 2 min and blue in running tap water for 5 min; (xi) mount with an aqueous mounting medium (MEDITE™ Medizintechnik AG, Switzerland).

Example 1: Evaluation of the Agonistic Activity of mAb1, mAb2 and mAb3

The experimental data are based on the use of isolated, unfractionated primary human PBMCs. Whole PBMC preparations (instead of isolated B cells or monocytes) more closely mimics the in vivo situation where an anti-CD40 mAb could have multiple direct and indirect effects on different leukocyte cell types. Using this PBMC proliferation assay it was determined that aglycosylated anti-CD40 mAbs mAb1 (N297A) and mAb2 (D265A), which retained the amino acid sequence of the antigen binding portion unchanged from the parental Chir12.12 antibody, retained the non-agonistic, CD40L blocking properties of the parental Chir12.12 mAb. The antibody mAb3 (LALA mutant) was weakly agonistic in the presence of IL-4.

Figure 2:
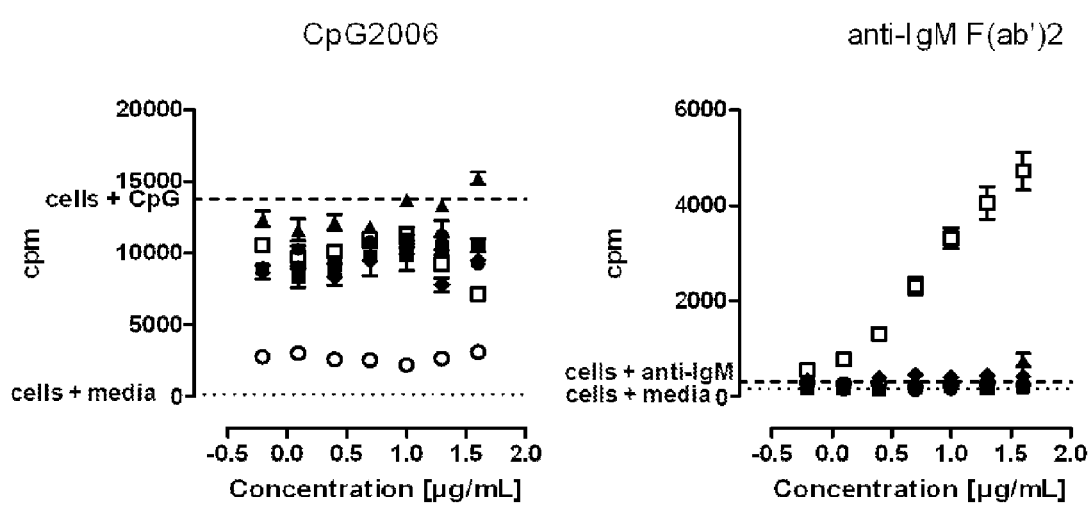
FIG. 2 shows incorporation of $^3$H-thymidine after 72 hours of human PBMC culture stimulated with a dose response of Chir12.12 (empty circle), mAb1 (filled circle), mAb2 (filled square), mAb3 (filled triangle), human CD40L (empty square), isotype control (filled diamond) co-stimulated in the presence of either 5 µg/ml anti-IgM F(ab')$_2$ or 1 µM CpG2006.

In particular, the experimental results show that none of the Fc silent anti-CD40 mAbs were capable of stimulating cell division by human PBMCs (n=4 donors), a result similar to that observed with the parental Chir12.12 mAb (see FIG. 1). PBMCs proliferated in response to CD40L. Neither mAb1 or mAb2 could enhance CpG2006 or anti-IgM F(ab')$_2$ induced proliferation of PBMCs (FIG. 2). Additionally, Chir12.12 failed to enhance anti-IgM F(ab')$_2$ induced proliferation of PBMCs, however unlike mAb1 and mAb2 it completely inhibited CpG induced PBMC proliferation.

Figure 3:
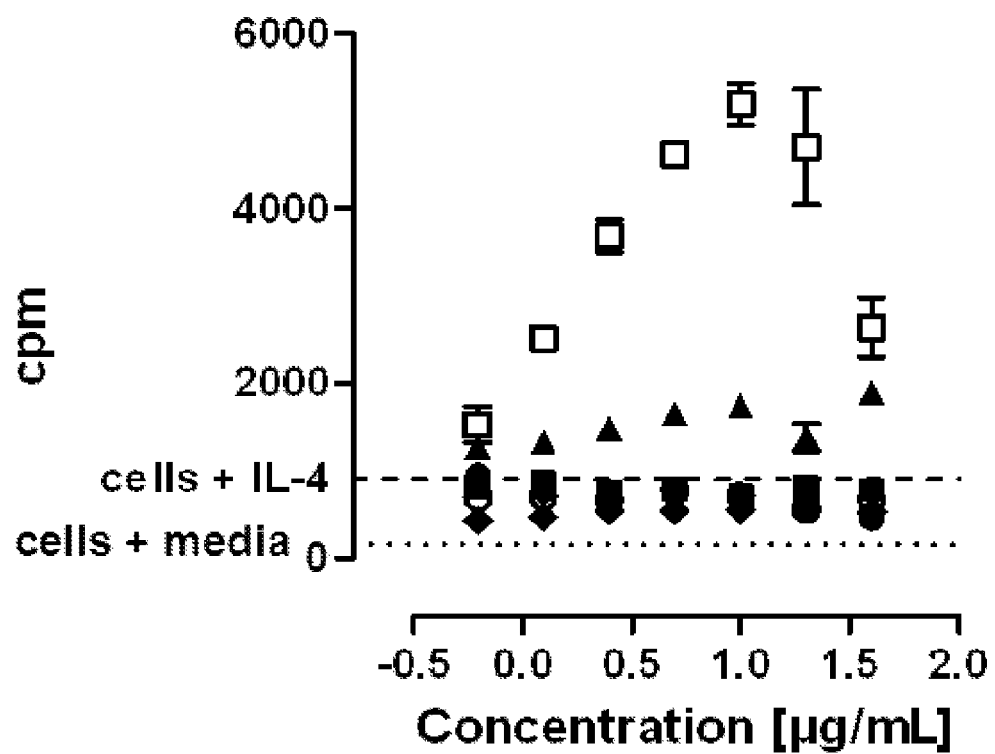
FIG. 3 shows incorporation of $^3$H-thymidine after 72 hours of human PBMC culture stimulated with a dose response of Chir12.12 (empty circle), mAb1 (filled circle), mAb2 (filled square), mAb3 (black triangle), human CD40L (empty square), isotype control (filled diamond) co-stimulated in the presence of 75 ng/ml IL-4.
Figure 4:
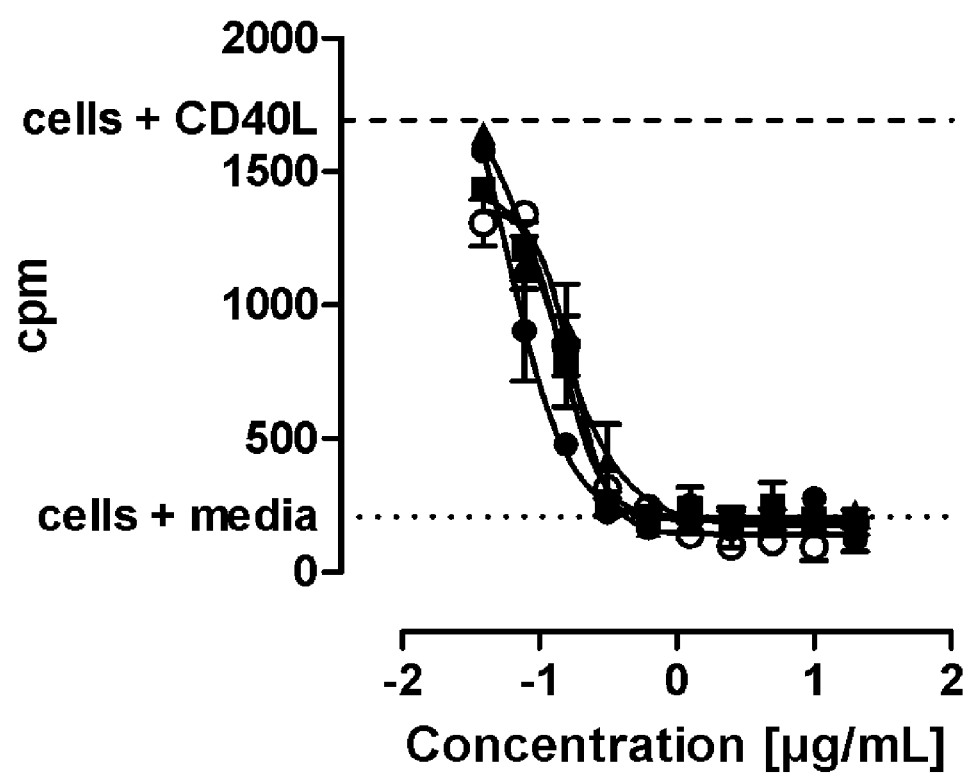
FIG. 4 shows incorporation of $^3$H-thymidine after 72 hours of human PBMC culture stimulated with 20 µg/ml CD40L with a dose response of Chir12.12 (empty circle), mAb1 (filled circle), mAb2 (filled square), mAb3 (black triangle) or human CD40L (empty square).

In the presence of IL-4, mAb3 (LALA mutation) was observed to induce low but reproducible (n=4 donors) levels of thymidine incorporation above that induced by IL-4 alone, whereas mAb1, mAb2 and Chir12.12 did not (FIG. 3). Collectively these results indicated that with the exception of mAb3 (in the presence of IL-4), none of the anti-CD40 mAbs possessed agonistic activity.

The above results also clearly demonstrated that mAb1 and mAb2 did not have agonist activity in the presence of co-stimulatory signals. This is an important finding as it is likely that the leukocytes in a patient with chronic autoimmune disease may have an activated or partially activated phenotype and thus be sensitized to signaling via CD40 or other stimuli. It was noted that Chir12.12 (but not the Fc silent mAbs or CD40L) completely inhibited CpG2006 induced PBMC proliferation. CpG2006 is a synthetic ligand for Toll-like receptor 9 (TLR9), a receptor demonstrated to bind pathogen and host derived ssDNA. In humans TLR9 is expressed by B cells and (to a lesser extent) monocytes in peripheral blood. As CpG containing ODNs have previously been shown to enhance ADCC (Moga, et al. 2008), it can be speculated that CpG2006 is able to enhance ADCC mediated by the germline IgG1 Fc portion of the parental Chir12.12 mAb.

Example 2: Evaluation of the Ability of the Fc Silent Anti-CD40 mAbs to Block CD40L-Mediated PBMC Proliferation Previous data indicated that Chir12.12 could block CD40L-mediated proliferation of primary human B cells and human B cell lymphoma cell lines. We measured inhibition of CD40L-mediated PBMCs proliferation by Chir12.12 and the three antibodies according to the invention mAb1, mAb2, mAb3. Table 7 below presents the IC50 values for such inhibition tabulated in mg/ml (results presented as the mean of triplicate cultures with SEM and representative of 4 donors, independent experiments). The results demonstrate that Chir12.12 can also inhibit CD40L-mediated PBMCs proliferation. Additionally mAb1, mAb2 and mAb3 also completely blocked CD40L-mediated PBMC division with a potency similar to Chir12.12. None of the anti-CD40 mAbs blocked anti-IgM+IL-2 induced PBMC proliferation (data not shown) suggesting that the blocking activity of the anti-CD40 mAbs was target dependent (and not related to Fc function).

TABLE 7

IC50 values for anti-CD40 mAb mediated inhibition of CD40L-mediated proliferation of PBMCs (μg/ml).

| Antibody | IC50 |
| --- | --- |
| Chir12.12 (wt Fc) | 0.176 |
| mAb1 (N297A) | 0.058 |
| mAb2 (D265A) | 0.146 |
| mAb3 (LALA) | 0.118 |

Example 3: Binding of Anti-Human CD40 Antibody Variants to Human BJAB Cell Line

To exclude possible changes in specific binding to CD40, the binding of the three variants mAb1, mAb2 and mAb3 was tested in comparison to the parental Chir12.12 on a B cell line, BJAB, which constitutively expresses CD40. Binding was tested in a dose-titration starting at 10 μg/mL in a 1:2 dilution.

Figure 5:
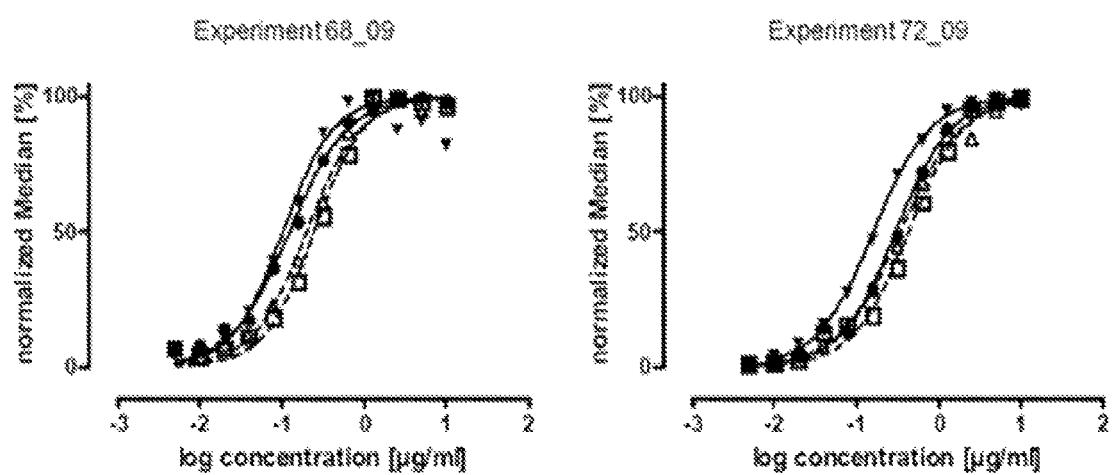
FIG. 5 shows dose-dependent binding of anti-human CD40 antibody to BJAB cell lines, respectively, Chir12.12 (filled circle), mAb1 (empty square), mAb2 (empty triangle), mAb3 (filled triangle).

To compare the curves of the different experiments, the highest median fluorescence intensity of each individual dose-titration was set to 100% binding and a non-linear curve fitting was applied. In two separate experiments all four antibody variants Chir12.12, mAb1, mAb2 and mAb3 showed equivalent binding curves on BJAB cells (FIG. 5). No changes in the binding capabilities of the variants could be observed with the different mutations of the Fc binding region of Chir12.12.

The above results thus demonstrated that the mutation of the Fc binding site did not impact the CD40 binding site of the variable regions of the parental Chir12.12. mAb1, mAb2 and mAb3 retained an equivalent binding of CD40 on BJAB cells.

Example 4: Stimulation/Inhibition of TNF Alpha Release from Human Monocytes Derived Dendritic Cells by the Anti-CD40 Fc Variants Stimulation of TNF Alpha Release from Human MoDCs by the Anti-CD40 Fc Variants Some anti-human CD40 antibodies have been shown to have agonistic effects on different cell population (Gruber 1989). To exclude that the Fc variants mAb1, mAb2, mAb3 and Chir12.12 lead to the activation of MoDCs, we investigated whether the antibodies on their own induce TNFα release when incubated for 48 h with the cells. In contrast to the antagonistic assay, seven day old human MoDCs were cultured for 48 h only in the presence of all four anti-CD40 variants in a dose-response curve starting at 10 μg/mL. Subsequently, supernatants were tested for the amount of TNFα by ELISA. All anti-CD40 variants mAb1, mAb2, mAb3 and Chir12.12 did not induce the release of TNFα from MoDCs as compared to the CD40L-stimulation as a positive control (data not shown). No dose dependency could be observed by all four antibody variants. The amounts of TNFα did not rise significantly above the level of unstimulated MoDCs (Data not shown). Therefore, an agonistic activity of these four antibodies could be excluded.

Inhibition of TNF Alpha Release from Human MoDCs by the Anti-CD40 Fc Variants

The parental Chir12.12 antibody blocks the interaction of CD40-CD40L and therefore should also block cell activation. Stimulation of CD40 on human monocyte-derived dendritic cells with CD40L trimers leads for example to the release of pro-inflammatory cytokines like TNFα (Ma 2009). Again, the change in the Fc region should not impact the blocking function of the variants in comparison to Chir12.12. All four antibodies should inhibit CD40L-mediated TNFα release from human MoDCs with an equivalent IC50.

Therefore, seven day old human MoDCs were stimulated for 24 h with MegaCD40L™, a double trimeric, recombinant construct in the presence of all four blocking anti-CD40 variants. Subsequently, supernatants were tested for the amount of TNFα by ELISA. All Fc-mutated variants mAb1, mAb2 and mAb3 showed the same dose-response inhibition like Chir12.12 in three separate experiments (data not shown). Preliminary results also show a similar inhibition of IL-23 release from human MoDCs (data not shown).

A non-linear curve fitting was applied to estimate an IC50 of all four antibodies and the average IC50 from the experiments was calculated. The average IC50 of the four variants for TNFα release from human MoDCs ranges between 32 ng/mL and 40 ng/mL (Table 8). In summary, the mutations in the Fc region did not impact the antagonistic effects of the antibody variants.

TABLE 8

IC50 of the different Fc variants for the inhibition of TNF alpha

|  | #1 | #2 | #3 | Average | SEM |
| --- | --- | --- | --- | --- | --- |
| Chir12.12 | n.c. | 41 | 30 | 36 | 4 |
| mAb1 | 23 | 44 | 58 | 40 | 10 |
| mAb2 | 41 | 12 | 42 | 33 | 10 |
| mAb3 | 39 | 8 | 47 | 32 | 12 |

IC50 in ng/mL for the different anti-human CD40 Fc variants from three independent experiments. The non-linear curve fitting in #1 for Chir12.12 did not allow a valid estimate of an IC50 (n.c. = not calculated).

It was thus shown by the above results that all four variants were inactive in inducing TNFα release from MoDCs. More importantly, all variants mAb1, mAb2 and mAb3 inhibited CD40L-mediated cytokine production by human MoDCs with similar efficacy in vitro as compared to Chir12.12.

Example 5: Data Summary

The following table 9 summarizes some of the important properties of the antibodies mAb1, mAb2 and mAb3 of the invention in comparison to the parental Chir12.12 antibody.

TABLE 9

Comparative data

| Selection Criteria | Chir 12.12 | mAb1 | mAb2 | mAb3 |
| --- | --- | --- | --- | --- |
| Binding of anti-CD40 Abs to human CD40 (BIACORE ®, Kd nM) | 0.55 | 0.69 | 0.49 | 0.33 |
| ADCC activity (normalized specific lysis) | 100% | <1% | <1% | 40% |
| Agonist activity on huPBMCs (EC50, ng/ml) | >10000 | >10000 | >10000 | >10000 |
| CD40L inhibition - huPBMCs (IC50, ng/ml) | 13 | 15 | 17 | 15 |
| $T_{1/2}$ (days) - Rat PK (10 mg/kg) | 9.3 +/− 0.90 | 8.8 +/− 0.49 | 11.6 +/− 2.3 | n.d |

Example 6: Brief Description of Useful Amino Acid and Nucleotide Sequences for Practicing the Invention

| SEQ ID NO: | Description of the sequence |
| --- | --- |
| 1 | HCDR1 amino acid sequence of CHIR-12.12, mAb1, mAb2, mAb3 |
| 2 | HCDR2 amino acid sequence of CHIR-12.12, mAb1, mAb2, mAb3 |
| 3 | HCDR3 amino acid sequence of CHIR-12.12, mAb1, mAb2, mAb3 |
| 4 | LCDR1 amino acid sequence of CHIR-12.12, mAb1, mAb2, mAb3 |
| 5 | LCDR2 amino acid sequence of CHIR-12.12, mAb1, mAb2, mAb3 |
| 6 | LCDR3 amino acid sequence of CHIR-12.12, mAb1, mAb2, mAb3 |
| 7 | VH amino acid sequence of CHIR-12.12, mAb1, mAb2, mAb3 |
| 8 | VL amino acid sequence of CHIR-12.12, mAb1, mAb2, mAb3 |
| 9 | Amino acid sequence of full length heavy chain of CHIR-12.12 |
| 10 | Amino acid sequence of full length light chain of CHIR-12.12 |
| 11 | Amino acid sequence of full length heavy chain of mAb1 |
| 12 | Amino acid sequence of full length light chain of mAb1 |
| 13 | Amino acid sequence of full length heavy chain of mAb2 |
| 14 | Amino acid sequence of full length light chain of mAb2 |
| 15 | Amino acid sequence of full length heavy chain of mAb3 |
| 16 | Amino acid sequence of full length light chain of mAb3 |
| 17 | Amino acid sequence of Fc region of mAb1 |
| 18 | Amino acid sequence of Fc region of mAb2 |
| 19 | Amino acid sequence of Fc region of mAb3 |
| 20 | DNA encoding Full length heavy chain of CHIR-12.12 |
| 21 | DNA encoding Full length light chain of CHIR-12.12 |
| 22 | DNA encoding Full length heavy chain of mAb1 |
| 23 | DNA encoding Full length light chain of mAb1 |
| 24 | DNA encoding Full length heavy chain of mAb2 |
| 25 | DNA encoding Full length light chain of mAb2 |
| 26 | DNA encoding Full length heavy chain of mAb3 |
| 27 | DNA encoding Full length light chain of mAb3 |
| 28 | Amino acid sequence of human CD40 |

Example 7: Useful Amino Acid and Nucleotide Sequences for Practicing the Invention

| SEQ ID NO: | Detailed amino acid or nucleotide sequences |
|---|---|
| 1 | SYGMH |
| 2 | VISYEESNRYHADSVKG |
| 3 | DGGIAAPGPDY |
| 4 | RSSQSLLYSNGYNYLD |
| 5 | LGSNRAS |
| 6 | MQARQTPFT |
| 7 | QVQLVESGGGVVQPGRSLRLSCAASGFTFSSYGMHWVRQA PGKGLEWVAVISYEESNRYHADSVKGRFTISRDNSKITLY LQMNSLRTEDTAVYYCARDGGIAAPGPDYWGQGTLVTVSS |
| 8 | DIVMTQSPLSLTVTPGEPASISCRSSQSLLYSNGYNYLDW YLQKPGQSPQVLISLGSNRASGVPDRFSGSGSGTDFTLKI SRVEAEDVGVYYCMQARQTPFTFGPGTKVDIR |
| 9 | QVQLVESGGGVVQPGRSLRLSCAASGFTFSSYGMHWVRQA PGKGLEWVAVISYEESNRYHADSVKGRFTISRDNSKITLY LQMNSLRTEDTAVYYCARDGGIAAPGPDYWGQGTLVTVSS ASTKGPSVFPLAPASKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK |
| 10 | DIVMTQSPLSLTVTPGEPASISCRSSQSLLYSNGYNYLDW YLQKPGQSPQVLISLGSNRASGVPDRFSGSGSGTDFTLKI SRVEAEDVGVYYCMQARQTPFTFGPGTKVDIRRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC |
| 11 | QVQLVESGGGVVQPGRSLRLSCAASGFTFSSYGMHWVRQA PGKGLEWVAVISYEESNRYH ADSVKGRFTI SRDNSKITLY LQMNSLRTED TAVYYCARDGGIAAPGPDYW GQGTLVTVSS ASTKGPSVFP LAPSSKSTSG GTAALGCLVKDYFPEPVTVS WNSGALTSGV HTFPAVLQSS GLYSLSSVVT VPSSSLGTQTYICNVNHKPS NTKVDKRVEP KSCDKTHTCP PCPAPELLGG PSVFLFPPKPKDTLMISRTP EVTCVVVDVS HEDPEVKFNW YVDGVEVHNA KTKPREEQYASTYRVVSVLT VLHQDWLNGK EYKCKVSNKA LPAPIEKTIS KAKGQPREPQVYTLPPSREE MTKNQVSLTC LVKGFYPSDI AVEWESNGQP ENNYKTTPPVLDSDGSFFLY SKLTVDKSRW QQGNVFSCSV MHEALHNHYT QKSLSLSPGK |
| 12 | DIVMTQSPLSLTVTPGEPAS ISCRSSQSLL YSNGYNYLDW YLQKPGQSPQVLISLGSNRA SGVPDRFSGS GSGTDFTLKI SRVEAEDVGV YYCMQARQTPFTFGPGTKVD IRRTVAAPSV FIFPPSDEQL KSGTASVVCL LNNFYPREAKVQWKVDNALQ SGNSQESVTE QDSKDSTYSL SSTLTLSKAD YEKHKVYACEVTHQGLSSPV TKSFNRGEC |
| 13 | QVQLVESGGG VVQPGRSLRL SCAASGFTFS SYGMHWVRQA PGKGLEWVAVISYEESNRYH ADSVKGRFTI SRDNSKITLY LQMNSLRTED TAVYYCARDGGIAAPGPDYW GQGTLVTVSS ASTKGPSVFP LAPSSKSTSG GTAALGCLVKDYFPEPVTVS WNSGALTSGV HTFPAVLQSS GLYSLSSVVT VPSSSLGTQTYICNVNHKPS NTKVDKRVEP KSCDKTHTCP PCPAPELLGG PSVFLFPPKPKDTLMISRTP EVTCVVVAVS HEDPEVKFNW YVDGVEVHNA KTKPREEQYNSTYRVVSVLT VLHQDWLNGK EYKCKVSNKA LPAPIEKTIS KAKGQPREPQVYTLPPSREE MTKNQVSLTC LVKGFYPSDI AVEWESNGQP ENNYKTTPPVLDSDGSFFLY SKLTVDKSRW QQGNVFSCSV MHEALHNHYT QKSLSLSPGK |

-continued

| SEQ ID NO: | Detailed amino acid or nucleotide sequences |
|---|---|
| 14 | DIVMTQSPLS LTVTPGEPAS ISCRSSQSLL YSNGYNYLDW YLQKPGQSPQVLISLGSNRA SGVPDRFSGS GSGTDFTLKI SRVEAEDVGV YYCMQARQTPFTFGPGTKVD IRRTVAAPSV FIFPPSDEQL KSGTASVVCL LNNFYPREAKVQWKVDNALQ SGNSQESVTE QDSKDSTYSL SSTLTLSKAD YEKHKVYACEVTHQGLSSPV TKSFNRGEC |
| 15 | QVQLVESGGG VVQPGRSLRL SCAASGFTFS SYGMHWVRQA PGKGLEWVAVISYEESNRYH ADSVKGRFTI SRDNSKITLY LQMNSLRTED TAVYYCARDGGIAAPGPDYW GQGTLVTVSS ASTKGPSVFP LAPSSKSTSG GTAALGCLVKDYFPEPVTVS WNSGALTSGV HTFPAVLQSS GLYSLSSVVT VPSSSLGTQTYICNVNHKPS NTKVDKRVEP KSCDKTHTCP PCPAPEAAGG PSVFLFPPKPKDTLMISRTP EVTCVVVDVS HEDPEVKFNW YVDGVEVHNA KTKPREEQYNSTYRVVSVLT VLHQDWLNGK EYKCKVSNKA LPAPIEKTIS KAKGQPREPQVYTLPPSREE MTKNQVSLTC LVKGFYPSDI AVEWESNGQP ENNYKTTPPVLDSDGSFFLY SKLTVDKSRW QQGNVFSCSV MHEALHNHYT QKSLSLSPGK |
| 16 | DIVMTQSPLS LTVTPGEPAS ISCRSSQSLL YSNGYNYLDW YLQKPGQSPQVLISLGSNRA SGVPDRFSGS GSGTDFTLKI SRVEAEDVGV YYCMQARQTPFTFGPGTKVD IRRTVAAPSV FIFPPSDEQL KSGTASVVCL LNNFYPREAKVQWKVDNALQ SGNSQESVTE QDSKDSTYSL SSTLTLSKAD YEKHKVYACEVTHQGLSSPV TKSFNRGEC |
| 17 | APELLGGPSVFLFPPKPKDTLMISRTPEVTCVVVDVSHEDPEVKFNWYVDGV EVHNAKTKPREEQYASTYRVVSVLTVLHQDWLNGKEYKCKVSNKALPAPIEK TISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQ KSLSLSPGK |
| 18 | APELLGGPSVFLFPPKPKDTLMISRTPEVTCVVVAVSHEDPEVKFNWYVDGV EVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQ KSLSLSPGK |
| 19 | APEAAGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQ KSLSLSPGK |
| 20 | CAGGTGCAGTTGGTGGAGTCTGGGGGAGGCGTGGTCCAGCCTGGGAGG TCCCTGAGACTCTCCTGTGCAGCCTCTGGATTCACCTTCAGTAGCTAT GGCATGCACTGGGTCCGCCAGGCTCCAGGCAAGGGGCTGGAGTGGGTG GCAGTTATATCATATGAGGAAAGTAATAGATACCATGCAGACTCCGTG AAGGGCCGATTCACCATCTCCAGAGACAATTCCAAGATCACGCTGTAT CTGCAAATGAACAGCCTCAGAACTGAGGACACGGCTGTGTATTACTGT GCGAGAGATGGGGGTATAGCAGCACCTGGGCCTGACTACTGGGGCCAG GGAACCCTGGTCACCGTCTCCTCAGCAAGTACCAAGGGCCCATCCGTC TTCCCCCTGGCGCCCGCTAGCAAGAGCACCTCTGGGGGCACAGCGGCC CTGGGCTGCCTGGTCAAGGACTACTTCCCCGAACCGGTGACGGTGTCG TGGAACTCAGGCGCCCTGACCAGCGGCGTGCACACCTTCCCGGCTGTC CTACAGTCCTCAGGACTCTACTCCCTCAGCAGCGTGGTGACCGTGCCC TCCAGCAGCTTGGGCACCCAGACCTACATCTGCAACGTGAATCACAAG CCCAGCAACACCAAGGTGGACAAGAGAGTTGGTGAGAGGCCAGCACAG GGAGGGAGGGTGTCTGCTGGAAGCCAGGCTCAGCGCTCCTGCCTGGAC GCATCCCGGCTATGCAGTCCCAGTCCAGGGCAGCAAGGCAGGCCCCGT CTGCCTCTTCACCCGGAGGCCTCTGCCCGCCCCACTCATGCTCAGGGA GAGGGTCTTCTGGCTTTTTCCCCAGGCTCTGGGCAGGCACAGGCTAGG TGCCCCTAACCCAGGCCCTGCACACAAAGGGGCAGGTGCTGGGCTCAG ACCTGCCAAGAGCCATATCCGGGAGGACCCTGCCCCTGACCTAAGCCC ACCCCAAAGGCCAAACTCTCCACTCCCTCAGCTCGGACACCTTCTCTC CTCCCAGATTCCAGTAACTCCCAATCTTCTCTCTGCAGAGCCCAAATC TTGTGACAAAACTCACACATGCCCACCGTGCCCAGGTAAGCCAGCCCA GGCCTCGCCCTCCAGCTCAAGGCGGGACAGGTGCCCTAGAGTAGCCTG CATCCAGGGACAGGCCCCAGCCGGGTGCTGACACGTCCACCTCCATCT CTTCCTCAGCACCTGAACTCCTGGGGGGACCGTCAGTCTTCCTCTTCC CCCCAAAACCCAAGGACACCCTCATGATCTCCCGGACCCCTGAGGTCA CATGCGTGGTGGTGGACGTGAGCCACGAAGACCCTGAGGTCAAGTTCA ACTGGTACGTGGACGGCGTGGAGGTGCATAATGCCAAGACAAAGCCGC GGGAGGAGCAGTACAACAGCACGTACCGTGTGGTCAGCGTCCTCACCG TCCTGCACCAGGACTGGCTGAATGGCAAGGAGTACAAGTGCAAGGTCT CCAACAAAGCCCTCCCAGCCCCCATCGAGAAAACCATCTCCAAAGCCA AAGGTGGGACCCGTGGGGTGCGAGGGCCACATGGACAGAGGCCGGCTC GGCCCACCCTCTGCCCTGAGAGTGACCGCTGTACCAACCTCTGTCCCT ACAGGGCAGCCCCGAGAACCACAGGTGTACACCCTGCCCCCATCCCGG |

| SEQ ID NO: | Detailed amino acid or nucleotide sequences |
|---|---|
| | GAGGAGATGACCAAGAACCAGGTCAGCCTGACCTGCCTGGTCAAAGGC<br>TTCTATCCCAGCGACATCGCCGTGGAGTGGGAGAGCAATGGGCAGCCG<br>GAGAACAACTACAAGACCACGCCTCCCGTGCTGGACTCCGACGGCTCC<br>TTCTTCCTCTATAGCAAGCTCACCGTGGACAAGAGCAGGTGGCAGCAG<br>GGGAACGTCTTCTCATGCTCCGTGATGCATGAGGCTCTGCACAACCAC<br>TACACGCAGAAGAGCCTCTCCCTGTCTCCGGGTAAA |
| 21 | GATATTGTGATGACTCAGTCTCCACTCTCCCTGACCGTCACCCCTGGA<br>GAGCCGGCCTCCATCTCCTGCAGGTCCAGTCAGAGCCTCCTGTATAGT<br>AATGGATACAACTATTTGGATTGGTACCTGCAGAAGCCAGGGCAGTCT<br>CCACAGGTCCTGATCTCTTTGGGTTCTAATCGGGCCTCCGGGGTCCCT<br>GACAGGTTCAGTGGCAGTGGATCAGGCACAGATTTTACACTGAAAATC<br>AGCAGAGTGGAGGCTGAGGATGTTGGGGTTTATTACTGCATGCAAGCT<br>CGACAAACTCCATTCACTTTCGGCCCTGGGACCAAAGTGGATATCAGA<br>CGAACTGTGGCTGCACCATCTGTCTTCATCTTCCCGCCATCTGATGAG<br>CAGTTGAAATCTGGAACTGCCTCTGTTGTGTGCCTGCTGAATAACTTC<br>TATCCCAGAGAGGCCAAAGTACAGTGGAAGGTGGATAACGCCCTCCAA<br>TCGGGTAACTCCCAGGAGAGTGTCACAGAGCAGGACAGCAAGGACAGC<br>ACCTACAGCCTCAGCAGCACCCTGACGCTGAGCAAAGCAGACTACGAG<br>AAACACAAAGTCTACGCCTGCGAAGTCACCCATCAGGGCCTGAGCTCG<br>CCCGTCACAAAGAGCTTCAACAGGGGAGAGTGT |
| 22 | CAGGTGCAGCTGGTGGAATCTGGCGGCGGAGTGGTGCAGCCTGGCCGG<br>TCCCTGAGACTGTCTTGCGCCGCCTCCGGCTTCACCTTCTCCAGCTAC<br>GGCATGCACTGGGTGCGACAGGCCCTGGCAAGGGACTGGAATGGGTG<br>GCCGTGATCTCCTACGAGGAATCCAACAGATACCACGCTGACTCCGTG<br>AAGGGCCGGTTCACAATCTCCCGGGACAACTCCAAGATCACCCTGTAC<br>CTGCAGATGAACTCCCTGCGGACCGAGGACACCGCCGTGTACTACTGC<br>GCCAGGGACGGAGGAATCGCCGCTCCTGGACCTGATTATTGGGGCCAG<br>GGCACCCTGGTGACAGTGTCCTCCGCTAGCACCAAGGGCCCCTCCGTG<br>TTCCCTCTGGCCCCCTCCAGCAAGTCCACCTCTGGCGGCACCGCCGCT<br>CTGGGCTGCCTGGTGAAAGACTACTTCCCCGAGCCCGTGACCGTGTCC<br>TGGAACTCTGGCGCCCTGACCTCCGGCGTGCACACCTTTCCAGCCGTG<br>CTGCAGTCCTCCGGCCTGTACTCCCTGTCCTCCGTGGTGACCGTGCCC<br>TCTAGCTCTCTGGGCACCCAGACCTACATCTGCAACGTGAACCACAAG<br>CCCTCCAACACCAAGGTGGACAAGCGGGTGGAACCCAAGTCCTGCGAC<br>AAGACCCACACCTGTCCCCCTGCCCTGCCCCTGAACTGCTGGGCGGA<br>CCTTCCGTGTTCCTGTTCCCCCCAAAGCCCAAGGACACCCTGATGATC<br>TCCCGGACCCCCGAAGTGACCTGCGTGGTGGTGGACGTGTCCCACGAG<br>GACCCTGAAGTGAAGTTCAATTGGTACGTGGACGGCGTGGAAGTGCAC<br>AACGCCAAGACCAAGCCCAGAGAGGAACAGTACGCCTCCACCTACCGG<br>GTGGTGTCTGTGCTGACCGTGCTGCACCAGGACTGGCTGAACGGCAAA<br>GAGTACAAGTGCAAGGTCTCCAACAAGGCCCTGCCTGCCCCCATCGAA<br>AAGACCATCTCCAAGGCCAAGGGCCAGCCCCGCGAGCCACAGGTGTAC<br>ACACTGCCCCCAGCCGGGAAGAGATGACCAAGAACCAGGTGTCCCTG<br>ACCTGTCTGGTCAAAGGCTTCTACCCCTCCGATATCGCCGTGGAGTGG<br>GAGTCCAACGGACAGCCCGAGAACAACTACAAGACCACCCCCCCTGTG<br>CTGGACTCCGACGGCTCATTCTTCCTGTACTCCAAGCTGACCGTGGAC<br>AAGTCCCGGTGGCAGCAGGGCAACGTGTTCTCCTGCTCCGTGATGCAC<br>GAGGCCCTGCACAACCACTACACCCAGAAGTCCCTGTCCCTGAGCCCC<br>GGCAAG |
| 23 | GACATCGTGATGACCCAGTCCCCCCTGTCCCTGACCGTGACACCTGGC<br>GAGCCTGCCTCTATCTCCTGCAGATCCTCCCAGTCCCTGCTGTACTCC<br>AACGGCTACAACTACCTGGACTGGTATCTGCAGAAGCCCGGCCAGTCC<br>CCACAGGTGCTGATCTCCCTGGGCTCCAACAGAGCCTCTGGCGTGCCC<br>GACCGGTTCTCCGGCTCTGGCTCTGGCACCGACTTCACACTGAAGATC<br>TCACGGGTGGAAGCCGAGGACGTGGGCGTGTACTACTGCATGCAGGCC<br>CGGCAGACCCCCTTCACCTTCGGCCCTGGCACCAAGGTGGACATCCGG<br>CGTACGGTGGCCGCTCCCAGCGTGTTCATCTTCCCCCCCAGCGACGAG<br>CAGCTGAAGAGCGGCACCGCCAGCGTGGTGTGCCTGCTGAACAACTTC<br>TACCCCCGGGAGGCCAAGGTGCAGTGGAAGGTGGACAACGCCCTGCAG<br>AGCGGCAACAGCCAGGAGAGCGTCACCGAGCAGGACAGCAAGGACTCC<br>ACCTACAGCCTGAGCAGCACCCTGACCCTGAGCAAGGCCGACTACGAG<br>AAGCATAAGGTGTACGCCTGCGAGGTGACCCACCAGGGCCTGTCCAGC<br>CCCGTGACCAAGAGCTTCAACAGGGGCGAGTGC |
| 24 | CAGGTGCAGCTGGTGGAATCTGGCGGCGGAGTGGTGCAGCCTGGCCGG<br>TCCCTGAGACTGTCTTGCGCCGCCTCCGGCTTCACCTTCTCCAGCTAC<br>GGCATGCACTGGGTGCGACAGGCCCTGGCAAGGGACTGGAATGGGTG<br>GCCGTGATCTCCTACGAGGAATCCAACAGATACCACGCTGACTCCGTG<br>AAGGGCCGGTTCACAATCTCCCGGGACAACTCCAAGATCACCCTGTAC<br>CTGCAGATGAACTCCCTGCGGACCGAGGACACCGCCGTGTACTACTGC<br>GCCAGGGACGGAGGAATCGCCGCTCCTGGACCTGATTATTGGGGCCAG<br>GGCACCCTGGTGACAGTGTCCTCCGCTAGCACCAAGGGCCCCTCCGTG<br>TTCCCTCTGGCCCCCTCCAGCAAGTCCACCTCTGGCGGCACCGCCGCT |

| SEQ ID NO: | Detailed amino acid or nucleotide sequences |
|---|---|
| | CTGGGCTGCCTGGTGAAAGACTACTTCCCCGAGCCCGTGACCGTGTCC<br>TGGAACTCTGGCGCCCTGACCTCCGGCGTGCACACCTTTCCAGCCGTG<br>CTGCAGTCCTCCGGCCTGTACTCCCTGTCCTCCGTGGTGACCGTGCCC<br>TCTAGCTCTCTGGGCACCCAGACCTACATCTGCAACGTGAACCACAAG<br>CCCTCCAACACCAAGGTGGACAAGCGGGTGGAACCCAAGTCCTGCGAC<br>AAGACCCACACCTGTCCCCCCTGCCCTGCCCCTGAACTGCTGGGCGGA<br>CCTTCCGTGTTCCTGTTCCCCCCAAAGCCCAAGGACACCCTGATGATC<br>TCCCGGACCCCCGAAGTGACCTGCGTGGTGGTGGCCGTGTCCCACGAG<br>GACCCTGAAGTGAAGTTCAATTGGTACGTGGACGGCGTGGAAGTGCAC<br>AACGCCAAGACCAAGCCCAGAGAGGAACAGTACAACTCCACCTACCGG<br>GTGGTGTCTGTGCTGACCGTGCTGCACCAGGACTGGCTGAACGGCAAA<br>GAGTACAAGTGCAAGGTCTCCAACAAGGCCCTGCCTGCCCCATCGAA<br>AAGACCATCTCCAAGGCCAAGGGCCAGCCCCGCGAGCCACAGGTGTAC<br>ACACTGCCCCCCAGCCGGGAAGAGATGACCAAGAACCAGGTGTCCCTG<br>ACCTGTCTGGTCAAAGGCTTCTACCCCTCCGATATCGCCGTGGAGTGG<br>GAGTCCAACGGACAGCCCGAGAACAACTACAAGACCACCCCCCCTGTG<br>CTGGACTCCGACGGCTCATTCTTCCTGTACTCCAAGCTGACCGTGGAC<br>AAGTCCCGGTGGCAGCAGGGCAACGTGTTCTCCTGCTCCGTGATGCAC<br>GAGGCCCTGCACAACCACTACACCCAGAAGTCCCTGTCCCTGAGCCCC<br>GGCAAG |
| 25 | GACATCGTGATGACCCAGTCCCCCCTGTCCCTGACCGTGACACCTGGC<br>GAGCCTGCCTCTATCTCCTGCAGATCCTCCCAGTCCCTGCTGTACTCC<br>AACGGCTACAACTACCTGGACTGGTATCTGCAGAAGCCCGGCCAGTCC<br>CCACAGGTGCTGATCTCCCTGGGCTCCAACAGAGCCTCTGGCGTGCCC<br>GACCGGTTCTCCGGCTCTGGCTCTGGCACCGACTTCACACTGAAGATC<br>TCACGGGTGGAAGCCGAGGACGTGGGCGTGTACTACTGCATGCAGGCC<br>CGGCAGACCCCCTTCACCTTCGGCCCTGGCACCAAGGTGGACATCCGG<br>CGTACGGTGGCCGCTCCCAGCGTGTTCATCTTCCCCCCCAGCGACGAG<br>CAGCTGAAGAGCGGCACCGCCAGCGTGGTGTGCCTGCTGAACAACTTC<br>TACCCCCGGGAGGCCAAGGTGCAGTGGAAGGTGGACAACGCCCTGCAG<br>AGCGGCAACAGCCAGGAGAGCGTCACCGAGCAGGACAGCAAGGACTCC<br>ACCTACAGCCTGAGCAGCACCCTGACCCTGAGCAAGGCCGACTACGAG<br>AAGCATAAGGTGTACGCCTGCGAGGTGACCCACCAGGGCCTGTCCAGC<br>CCCGTGACCAAGAGCTTCAACAGGGGCGAGTGC |
| 26 | CAGGTGCAGCTGGTGGAATCTGGCGGCGGAGTGGTGCAGCCTGGCCGG<br>TCCCTGAGACTGTCTTGCGCCGCCTCCGGCTTCACCTTCTCCAGCTAC<br>GGCATGCACTGGGTGCGACAGGCCCCTGGCAAGGGACTGGAATGGGTG<br>GCCGTGATCTCCTACGAGGAATCCAACAGATACCACGCTGACTCCGTG<br>AAGGGCCGGTTCACAATCTCCCGGGACAACTCCAAGATCACCCTGTAC<br>CTGCAGATGAACTCCCTGCGGACCGAGGACACCGCCGTGTACTACTGC<br>GCCAGGGACGGAGGAATCGCCGCTCCTGGACCTGATTATTGGGGCCAG<br>GGCACCCTGGTGACAGTGTCCTCCGCTAGCACCAAGGGCCCCTCCGTG<br>TTCCCTCTGGCCCCTTCCAGCAAGTCTACCTCCGGCGGCACAGCTGCT<br>CTGGGCTGCCTGGTCAAGGACTACTTCCCTGAGCCTGTGACAGTGTCC<br>TGGAACTCTGGCGCCCTGACCTCTGGCGTGCACACCTTCCCTGCCGTG<br>CTGCAGTCCTCCGGCCTGTACTCCCTGTCCTCCGTGGTCACAGTGCCT<br>TCAAGCAGCCTGGGCACCCAGACCTATATCTGCAACGTGAACCACAAG<br>CCTTCCAACACCAAGGTGGACAAGCGGGTGGAGCCTAAGTCCTGCGAC<br>AAGACCCACACCTGTCCTCCCTGCCCTGCTCCTGAAGCTGCTGGCGGC<br>CCTTCTGTGTTCCTGTTCCCTCCAAAGCCCAAGGACACCCTGATGATC<br>TCCCGGACCCCTGAAGTGACCTGCGTGGTGGTGGACGTGTCCCACGAG<br>GATCCTGAAGTGAAGTTCAATTGGTACGTGGACGGCGTGGAGGTGCAC<br>AACGCCAAGACCAAGCCTCGGGAGGAACAGTACAACTCCACCTACCGG<br>GTGGTGTCCGTGCTGACCGTGCTGCACCAGGACTGGCTGAACGGCAAA<br>GAGTACAAGTGCAAAGTCTCCAACAAGGCCCTGCCTGCCCCTATCGAA<br>AAGACAATCTCCAAGGCCAAGGGCCAGCCTAGGGAACCCCAGGTGTAC<br>ACCCTGCCACCCAGCCGGGAGGAAATGACCAAGAACCAGGTGTCCCTG<br>ACCTGTCTGGTCAAGGGCTTCTACCCTTCCGATATCGCCGTGGAGTGG<br>GAGTCTAACGGCCAGCCTGAGAACAACTACAAGACCACCCCTCCTGTG<br>CTGGACTCCGACGGCTCCTTCTTCCTGTACTCCAAACTGACCGTGGAC<br>AAGTCCCGGTGGCAGCAGGGCAACGTGTTCTCCTGCTCCGTGATGCAC<br>GAGGCCCTGCACAACCACTACACCCAGAAGTCCCTGTCCCTGTCTCCC<br>GGCAAG |
| 27 | GACATCGTGATGACCCAGTCCCCCCTGTCCCTGACCGTGACACCTGGC<br>GAGCCTGCCTCTATCTCCTGCAGATCCTCCCAGTCCCTGCTGTACTCC<br>AACGGCTACAACTACCTGGACTGGTATCTGCAGAAGCCCGGCCAGTCC<br>CCACAGGTGCTGATCTCCCTGGGCTCCAACAGAGCCTCTGGCGTGCCC<br>GACCGGTTCTCCGGCTCTGGCTCTGGCACCGACTTCACACTGAAGATC<br>TCACGGGTGGAAGCCGAGGACGTGGGCGTGTACTACTGCATGCAGGCC<br>CGGCAGACCCCCTTCACCTTCGGCCCTGGCACCAAGGTGGACATCCGG<br>CGTACGGTGGCCGCTCCCAGCGTGTTCATCTTCCCCCCCAGCGACGAG<br>CAGCTGAAGAGCGGCACCGCCAGCGTGGTGTGCCTGCTGAACAACTTC<br>TACCCCCGGGAGGCCAAGGTGCAGTGGAAGGTGGACAACGCCCTGCAG |

| SEQ ID NO: | Detailed amino acid or nucleotide sequences |
|---|---|
| | AGCGGCAACAGCCAGGAGAGCGTCACCGAGCAGGACAGCAAGGACTCC<br>ACCTACAGCCTGAGCAGCACCCTGACCCTGAGCAAGGCCGACTACGAG<br>AAGCATAAGGTGTACGCCTGCGAGGTGACCCACCAGGGCCTGTCCAGC<br>CCCGTGACCAAGAGCTTCAACAGGGGCGAGTGC |
| 28 | MVRLPLQCVLWGCLLTAVHPEPPTACREKQYLINSQCCSLCQPGQKLV<br>SDCTEFTETECLPCGESEFLDTWNRETHCHQHKYCDPNLGLRVQQKGT<br>SETDTICTCEEGWHCTSEACESCVLHRSCSPGFGVKQIATGVSDTICE<br>PCPVGFFSNVSSAFEKCHPWTSCETKDLVVQQAGTNKTDVVCGPQDRL<br>RALVVIPIIFGILFAILLVLVFIKKVAKKPTNKAPHPKQEPQEINFPD<br>DLPGSNTAAPVQETLHGCQPVTQEDGKESRISVQERQ |

Example 8: Toxicology Results

The primary objective of the toxicology study was to determine the toxicity of mAb1, following once weekly intravenous administration to the cynomolgus monkey for 5 weeks (6 test item applications). The non-silent (ADCC) version of this antibody (Chir12.12) was also used in order to compare the effects of an ADCC-active antibody with the ADCC-silent version (mAb1).

In addition, animals were immunized with KLH in order to evaluate the efficacy of both anti-CD40 Abs.

There were no mortalities or changes in body weights, clinical signs, and estimated food consumption attributable to treatment with mAb1 or Chir12.12. Local reactions at KLH injection sites were comparable in all groups.

Also, there were no test item-related findings in ophthalmic and cardiovascular investigations.

In hematology a slight but statistically significant decrease in the percentage and absolute numbers of basophils was observed in mAb1- and Chir12.12-treated animals: a relation to test item-treatment cannot be excluded. Urine analysis revealed ketones in the urine of 1/5 mAb1-treated females and 2/5 Chir12.12-treated females with unclear relation to dosing. In clinical chemistry a slight trend to elevated lipase concentrations was observed for the Chir12.12-treated males as well as one female treated with Chir12.12, however this was considered to be of limited toxicological relevance.

Blood coagulation was not affected by treatment with mAb1 or Chir12.12 as assessed by prothrombin time, activated partial prothrombin time, and fibrinogen. Platelet counts appeared in the normal range. P-selectin or sCD40L concentrations in plasma did not indicate platelet activation.

In Chir12.12-treated animals, blood immunophenotyping showed a prominent decrease in CD20$^+$ B-cells, which was the expected pharmacological action of this antibody. Especially the CD20$^{low}$CD21$^+$ B-cells (which are considered to be CD40$^{high}$) were depleted by Chir12.12. However, also the CD20$^{high}$CD21$^-$ B-cells were decreased substantially especially towards the end of the study. Preferentially the CD20$^+$CD21$^+$CD27$^-$ naïve B-cells were depleted by the ADCC-active antibody Chir12.12, whereas the CD20$^+$CD21$^+$CD27$^+$ memory B-cells were hardly affected. There was also an approximate decrease of 50% in the absolute number of CD16$^+$ NK-cells in Chir12.12-treated animals. As expected, following treatment with mAb1 (which is ADCC-silent), the prominent decrease in CD20$^+$ B-cells was not observed nor was any decrease in absolute numbers of CD16$^+$ NK-cells. The only B-cells showing a moderate reduction during dosing were the CD20$^{high}$ CD21$^-$ B-cells. These cells are known to be macaque specific and of germinal center origin, therefore this finding is not considered relevant for transition to humans.

Immunophenotyping of spleen and KLH draining lymph nodes at necropsy revealed a similar picture. There was a decrease in the relative number of CD20$^+$ B-cells in Chir12.12-treated animals, however no relevant reduction of CD20$^+$ B-cells was observed for mAb1-treated animals with a slight to moderate reduction of CD21$^-$ B-cells (lymph nodes both sexes, spleen males only). There were no differences in the results of immunophenotyping for the right and left lymph node draining the KLH injection site.

The T-cell dependent antibody reaction (TDAR) showed that, in comparison to the control group, no IgG and IgM response to KLH was observed in the mAb1- or Chir12.12-treated animals. As blocking of B-cell activation by inhibiting CD40-CD40 ligand interaction is the intended pharmacological action of mAb1, and as Chir12.12 is intended to deplete B-cells, this finding is not considered toxicologically relevant.

Toxicokinetic evaluation revealed that trough concentrations increased during the course of the study indicating accumulation of mAb1 and Chir12.12. Mean trough concentrations after the 4$^{th}$ and 5$^{th}$ dose were similar, indicating close-to-steady state conditions after the 5$^{th}$ dose for mAb1 and Chir12.12. Mean exposures (both genders) over the dosing interval (AUC$_T$) after the 4$^{th}$ and 5$^{th}$ dose were 906 and 990 h·mg/mL, respectively for mAb1, and 757 and 751 h·mg/mL, respectively for Chir12.12. The AUC$_T$ values were also indicative of close-to-steady state conditions after the 5$^{th}$ dose.

Macroscopic examinations did not show any evidence of target organ toxicity, and organ weights were also within the normal range for this species.

Microscopically, test item-related findings of both antibodies were seen in all lymphatic organs (spleen and lymph nodes (mesenteric, mandibular, axillary, and inguinal)), where mAb1 and Chir12.12 caused complete suppression of germinal centre development in cortical B-cell areas. CD20 immunostaining of spleen and KLH draining and contralateral lymph node tissue showed reduced size of lymphoid follicles in the spleen as well as B-cell depletion in spleen and lymph nodes, an effect which was much more pronounced in Chir12.12-treated animals compared to the treatment with mAb1. Germinal center findings in mAb1-treated animals correspond to the reduction of CD21$^-$ B-cells seen at immunophenotyping. CD40 immunostaining showed a significant reduction in the staining of CD40 in lymph nodes and spleen following treatment with either mAb1 or Chir12.12.

In conclusion, based on the results of this study, once weekly intravenous administration of mAb1 or Chir12.12 for 5 weeks (6 administrations) at a concentration of 100 mg/kg to male and female cynomolgus monkeys was well tolerated. Immunophenotyping showed a depletion of B-cells in Chir12.12-treated but not mAb1-treated animals with exception of CD21− B-cells, however the TDAR showed an absence of IgG and IgM reaction after KLH immunization in both mAb1- and Chir12.12-treated animals. Histopathology revealed lack of germinal centers in spleen and lymph nodes from mAb1- and Chir12.12-treated animals. The effects on B-cells are the desired pharmacologic actions and therefore not considered to be adverse. The no-observable-adverse-effect level (NOAEL) is considered to be at the dose of 100 mg/kg for both mAb1 and Chir12.12 under the conditions of this study.

Example 9: Additional In Vitro Profiling of mAb1

The binding and functional cross-reactivity of mAb1 was determined between human, Rhesus and Cynomolgus leukocytes. Table 10 shows a direct comparison of the binding EC50s for mAb1 in all three species.

TABLE 10

Human and NHP cross-reactivity of mAb1.

| Assay | Human | Rhesus | Cynomolgus |
|---|---|---|---|
| CD40 binding (CD20+ B cells-FACS) (EC50, µg/ml) | 0.26, 0.28 | 0.22 +/− 0.033 (n = 6) | 0.3, 0.24 |
| CD154 inhibition (hu B cells & PBMCs) (IC50, µg/ml) | 0.058, 0.075 (human tonsil B cells) | 0.03 +/− 0.017 (n = 6) (PBMCs) | 0.015, 0.02 (PBMCs) | mAb1 binds to CD20+ cells (B cells) of all three species with comparable EC50. Additionally, mAb1 could inhibit CD154+IL-4 induced proliferation of human tonsil B cells as well as PBMCs from Cynomolgus and Rhesus. Collectively these results indicated that the ability of mAb1 to bind CD40 and inhibit CD154-induced proliferation of human B cells or non-human primate PBMCs was very similar. The availability of in vitro receptor occupancy (RO) data and functional inhibition enabled the relationship between these two variables to be determined for each species (Table 11).

TABLE 11

Relationship between mAb1 RO and functional inhibition

| | IC$_{50}$ in the functional inhibition test[a] (µg/mL) | Corresponding in vivo RO[b,c] (%) |
|---|---|---|
| Rhesus | 0.02551 | 22.9 |
| Human | 0.067 | 43.8 |

[a]Soluble CD154 + IL4-induced proliferation in rhesus with PBMCs and in human with Tonsil B cells.
[b]assuming in vivo KD in rhesus and in human is the same as the one computed in the PK/PD study in cyno.
[c]assuming mAb1 is well above [target] the Hill-Langmuir equation is applicable.

The results indicate that approximately 2-fold less RO is required by mAb1 Rhesus PBMCs to inhibit PBMC proliferation by 50% in comparison to human B cells. In human, full inhibition could be obtained with ca. 75% (in vivo predicted) RO.

Example 10: Transplant Study

Graft Survival

Combination treatment with mAb1 (30 mg/kg i.v.) and Cyclosporine A, 20 mg/kg orally during allograft kidney transplantation resulted in a significant prolongation of the survival of the 6 animals involved in the study. The grafts were functional during >91*, 31, >92*, >92*, >98* and >98* days (mean: >83.6 days) in animals #5529, #5533, #5523, #5524, #5536 and #5538, respectively (* end of protocol). The survival in untreated animals (or treated with sub-therapeutic IS-doses) ranged from 7-10 days (historical data).

Animal #5533 was euthanized 31 days post-transplant, due to acute kidney failure and anuria. This pathology appeared after maintained hypertensive period and anaesthesia for biopsy collection.

Monitoring Post-Transplant (a) Creatinine (SCrea) and Urea (SUrea) Serum Concentrations SCrea was the main parameter used for the evaluation of the kidney function. In all 6 animals, SCrea levels increased above the baseline levels one day after transplant (from 81.8±14.6 to 221.5±37.1 µmol/l). Such rise in SCrea is a common feature during the first week post-transplant (Table 12).

TABLE 12

Changes in SCrea observed in NHP kidney allograft recipients treated with mAb1 and CsA combination therapy at 30 and 20 mg/kg, respectively

| Days post transplant | sCrea level (µmol/l) | | | | | |
|---|---|---|---|---|---|---|
| | #5536 | #5538 | #5523 | #5524 | #5529 | #5533 |
| −4 | 101 | 109 | 85 | 73 | 81 | 86 |
| −1 | 106 | 89 | 80 | 71 | 95 | 76 |
| 0 | 95 | 105 | 74 | 72 | 76 | 69 |
| 1 | 234 | 238 | 213 | 198 | 277 | 169 |
| 3 | 190 | 261 | 148 | 155 | 243 | 191 |
| 7 | 112 | 189 | 136 | 141 | 110 | 110 |
| 10 | 111 | 172 | 193 | 206 | 102 | 139 |
| 14 | 101 | 166 | 209 | 165 | 103 | 156 |
| 17 | 113 | 181 | 277 | 157 | 94 | 175 |
| 21 | 114 | 162 | 192 | 117 | 111 | 206 |
| 24 | 112 | 156 | 155 | 124 | 111 | 191 |
| 28 | 95 | 133 | 119 | 111 | 100 | 170 |
| 31 | 95 | 139 | 119 | 106 | 122 | 629 |
| 35 | 103 | 135 | 110 | 100 | 104 | |
| 38 | 104 | 128 | 111 | 109 | 108 | |
| 42 | 107 | 113 | 110 | 101 | 114 | |
| 45 | 95 | 124 | 108 | 115 | 113 | |
| 49 | 103 | 118 | 104 | 106 | 101 | |
| 52 | 107 | 129 | 105 | 111 | 102 | |
| 56 | 122 | 103 | 112 | 95 | 101 | |
| 59 | 112 | 105 | 94 | 97 | 99 | |
| 63 | 110 | 120 | 115 | 115 | 99 | |
| 66 | 103 | 132 | 110 | 104 | 107 | |
| 70 | 101 | 116 | 91 | 100 | 105 | |
| 73 | 103 | 124 | 105 | 120 | 109 | |
| 77 | 103 | 109 | 98 | 121 | 105 | |
| 80 | 103 | 101 | 102 | 113 | 109 | |
| 84 | 101 | 104 | 120 | 126 | 110 | |
| 87 | 107 | 103 | 111 | 112 | 108 | |
| 91 | 100 | 112 | 119 | 112 | 105 | |
| 94 | 117 | 133 | | | | |

During the first week, SUrea concentrations experienced quick rises above the baseline measured on day 0 (4.5±1.3 mmol/l) (Table 13). In animals #5529/#5533 and #5536/#5538, SUrea levels were 16-20 mmol/l (day 3-5), whereas in animals #5523 and #5524 were 9 or 8 mmol/l (day 7), respectively.

TABLE 13

Changes in SUrea observed in NHP kidney allograft recipients treated with mAb1 and CsA combination therapy at 30 and 20 mg/kg, respectively

| Days post transplant | sUrea level (mmol/l) | | | | | |
|---|---|---|---|---|---|---|
| | #5536 | #5538 | #5523 | #5524 | #5529 | #5533 |
| −4 | 7 | 5 | 4 | 4 | 8 | 5 |
| −1 | 7 | 6 | 5 | 6 | 9 | 5 |
| 0 | 6 | 4 | 3 | 4 | 6 | 5 |
| 1 | 14 | 12 | 7 | 8 | 13 | 9 |
| 3 | 20 | 17 | 5 | 6 | 16 | 15 |
| 7 | 9 | 14 | 9 | 8 | 9 | 11 |
| 10 | 5 | 10 | 17 | 14 | 6 | 11 |
| 14 | 6 | 8 | 18 | 13 | 5 | 18 |
| 17 | 7 | 10 | 16 | 8 | 5 | 15 |
| 21 | 7 | 10 | 14 | 7 | 4 | 19 |
| 24 | 6 | 9 | 8 | 6 | 4 | 17 |
| 28 | 8 | 10 | 11 | 8 | 4 | 12 |
| 31 | 6 | 9 | 11 | 8 | 4 | 18 |
| 35 | 7 | 10 | 8 | 7 | 6 | |
| 38 | 7 | 8 | 6 | 5 | 6 | |
| 42 | 7 | 9 | 10 | 7 | 6 | |
| 45 | 7 | 9 | 10 | 8 | 6 | |
| 49 | 9 | 9 | 8 | 6 | 8 | |
| 52 | 6 | 8 | 6 | 6 | 7 | |
| 56 | 8 | 9 | 9 | 9 | 6 | |
| 59 | 4 | 8 | 9 | 10 | 8 | |
| 63 | 6 | 9 | 8 | 7 | 7 | |
| 66 | 7 | 11 | 7 | 7 | 7 | |
| 70 | 6 | 9 | 10 | 9 | 7 | |
| 73 | 7 | 9 | 9 | 10 | 5 | |
| 77 | 11 | 14 | 8 | 10 | 7 | |
| 80 | 6 | 7 | 7 | 8 | 7 | |
| 84 | 6 | 7 | 9 | 9 | 6 | |
| 87 | 6 | 8 | 8 | 8 | 6 | |
| 91 | 7 | 8 | 10 | 10 | 5 | |
| 94 | 7 | 8 | | | | |

One week after transplant, renal function tends to normalize and SCrea/Surea become closer to baseline levels. However, animals #5533, #5523 and #5524 (but not #5529, #5536 and #5538) presented an additional increase in SCrea/SUrea between days 7 and 19-25 post-transplant, indicating kidney malfunction. During this period signs like polidipsia/poliuria (#5523 and #5524), high maintained serum calcium (SCa) (#5533) or increase in graft volume (#5523 and #5524) could be observed.

After day 20-25, animals #5529, #5523, #5524, #5536 and #5538 improved and showed excellent kidney function until the end of the study. However, on day 31, animal #5533 displayed a pronounced increase in SCrea/SUrea levels, confirming an acute kidney failure (SCrea; 629 µmol/l and SUrea; 18 mmol/l). This pathology occurred after a maintained hypertensive period and biopsy procedure one day before euthanasia. During this period hypertensive peaks (~170 mmgHg systolic) and a hypotensive episode (~40 mmgHg systolic) were recorded.

(b) Serum Amylase, Lipase Concentrations, Body Weight and Platelet Counts

Serum amylase concentrations slightly increased in all animals about 1.3 fold on days 1-7 after transplantation (311±53 U/L on day 0 and 418±66.8 U/L on day 7 post-transplant) (Table 14). Animal #5533 presented the highest amylase concentration observed in the study on day 1 after-transplant (1050 U/L). Before transplant, there was no difference between amylase levels observed before the first mAb1 dose and 24 hours after (day −1 and day 0).

TABLE 14

Serum amylase concentrations (U/L) in kidney transplanted animals treated with a combination of mAb1 at 30 mg/kg i.v. and CsA at 20 mg/kg p.o.

| Time after-transplant | Average amylase (U/L) | STDEV | Fold increase |
|---|---|---|---|
| Day 0 | 311 | 52.95 | |
| Day 7 | 418.2 | 66.8 | 1.34 |
| Day 14 | 459.2 | 71.5 | 1.48 |
| Day 56 | 526.6 | 121.5 | 1.69 |
| Day 84 | 460.4 | 66.8 | 1.48 |

Lipase serum concentrations experienced, on average, minor changes pre- and post-transplant (Table 15). Only at the end of the experimental protocol, a minor increase could be seen (day 84; 2.18 fold). Animal #5533 showed the highest lipase concentration measured on day 1 (284.4 U/L). Lipase data from animal #5536 and #5538 was not available. Changes in amylase and lipase concentrations were similar to the levels found in other transplant-experiments using different antibodies or low molecular weight compounds (data not shown).

TABLE 15

Serum lipase concentrations (U/L) in four of the kidney transplanted animals treated with a combination of mAb1 at 30 mg/kg i.v. and CsA at 20 mg/kg p.o.

| Time after-transplant | Average lipase (U/L) | STDEV | Fold increase |
|---|---|---|---|
| Day 0 | 12 | 1.3 | |
| Day 7 | 13.05 | 2.26 | 1.09 |
| Day 14 | 12.9 | 1.25 | 1.08 |
| Day 56 | 16.6 | 3.41 | 1.38 |
| Day 84 | 26.2 | 21.06 | 2.18 |

A rapid and marked body weight loss could be mainly observed in animals #5529, #5533 and #5536. In all six transplanted animals, it ranged from −4 to −18% during the first 21 days following transplant. However, body weight loss tended to recover after that time point and towards the end of the study.

Platelet counts were normal (300-400 cells×103/µl) or increased during the post-transplant period 600-800 cells×103/µl. Animal #5529 received aspirin treatment during 3 days (day 7-9) due to quick increase in platelet counts. Animal #5533 presented long term thrombocytosis (>1000 cells×103/µl) and received aspirin treatment between days 7-26.

(c) mAb1 Blood Levels and B-Cell Counts

A reference PK/PD study and analysis was previously conducted in which cynomolgus monkeys were given a single intravenous dose of antibody at 10 mg/kg (data not shown). In this study, concentration vs. time profiles exhibited clear target mediated disposition (TMD), with one animal demonstrating a more rapid clearance as compared to another animal, as a consequence of a likely higher target expression level, emphasizing the role of target expression levels in governing PK. From this study, it was also established that when mAb1 serum concentrations were above ca. 5 microg/mL, this translated into almost 100% CD40 receptor occupancy.

The design of the transplant study (weekly and high mAb1 dose levels—30 mg/kg, and no recovery/washout phase) did not allow for the same level of analysis and modeling as the previously conducted PK/PD study. Nevertheless, the following observations were made (summarised in Table 16); i) mAb1 was not detected in samples collected prior to first dose, ii) mAb1 was detected throughout the all dose dosing phase and, iii) in all collected samples and inter-individual trough concentrations were variable (1200-2500 microg/mL for cynomolgus 5524, 1000-2000 microg/mL for cynomolgus 5523 and 850-2400 microg/mL for cynomolgus 5529). All exposure values were well above (170- to 500-fold) the concentration needed to obtain full receptor occupancy in cynomolgus monkey.

TABLE 16 mAb1 serum concentration for cynomolgus monkey #5533, #5529, #5523 and #5524

| | mAb1 (microg/mL) | | | |
|---|---|---|---|---|
| Time (days) | Cyno_5533 | Cyno_5529 | Cyno_5523 | Cyno_5524 |
| −1 | 0 | 0 | 0 | 0 |
| 3 | 591 | 618 | 1315 | 1384 |
| 7 | 682 | 1003 | 1033 | 1135 |
| 7.01 | 1557 | 1553 | 2452 | 2669 |
| 14 | 925 | 1037 | 1463 | 1744 |
| 28 | 654 | 896 | 1672 | 1965 |
| 42 | | 851 | 1770 | 1259 |
| 56 | | 1896 | 1991 | 1283 |
| 70 | | 2385 | 1641 | 2534 |

TABLE 16-continued mAb1 serum concentration for cynomolgus monkey #5533, #5529, #5523 and #5524

| | mAb1 (microg/mL) | | | |
|---|---|---|---|---|
| Time (days) | Cyno_5533 | Cyno_5529 | Cyno_5523 | Cyno_5524 |
| 84 | | 2191 | 1266 | 2402 |
| 91 | | 2069 | 1066 | 2071 |

Immunogenicity testing (monkey anti-mAb1 antibodies) was also evaluated in this study. All samples came out negative, but high mAb1 levels in this samples, could potentially prevented their detection due to drug interferences.

A partial depletion of CD20+ cells could be observed with time in all treated animals. Similar observations were seen in the previously conducted PK/PD study (data not shown).

Histology Results

Histopathological evaluation of the kidney allografts revealed no acute and chronic rejection in grafts #5523, #5524, #5529 and #5538, and borderline changes in graft #5536 that reached end of the experiment, i.e. (results summarised in Table 17). Minimal perivascular or interstitial infiltrates in animals #5523 #5524 and #5538, and minimal glomerular hypercellularity in animal #5529 were observed.

TABLE 17

Histology results

| Animal No. | Sample | Days post-transplant | Crea/Urea | Diagnosis |
|---|---|---|---|---|
| #5529 | biopsy | 30 | 100/4 | Banff: no rejection |
| 10-0001 | necropsy | 91 | 105/5 | Banff: no rejection (minimal glomerular hypercellularity, minimal intimal fibrosis) Other: Lack of GC formation in secondary lymphoid organs. Cecocolitis (B. coli). No other treatment related changes. |
| #5533 | biopsy | 30 | 170/12 | Banff: IA, diffuse early interstitial fibrosis, tubular vacuolization |
| 10-0002 | necropsy | 31 | 629/18 | Banff: other (tubular dilatation, interstitial infiltrates and fibrosis, minimal tubulitis, abscess around anastomosis, eosinophils around ureter) Other: Lack of GC formation in secondary lymphoid organs. Cecocolitis (B. coli). No other treatment related changes. |
| #5523 | biopsy | no | no | |
| 11-0001 | necropsy | 92 | 119/10 | Banff: no rejectio (minimal perivascular infiltrates, mucoid material in one vein)) Lack of GC formation in secondary lymphoid organs. No other treatment related changes. |
| #5524 | biopsy | no | no | |
| 11-0002 | necropsy | 92 | 112/10 | Banff: no rejection (minimal multifocal interstitial infiltrates), Lack of GC formation in secondary lymphoid organs. No other treatment related changes. |
| #5536 | biopsy | no | no | |
| 11-0002 | necropsy | 98 | 104/8 | Banff: borderline changes (minimal multifocal interstitial infiltrates with minimal focal tubulitis), focal plasma cells Lack of GC formation in secondary lymphoid organs. No other treatment related changes. |
| #5538 | biopsy | no | no | |
| 11-0002 | necropsy | 98 | 114/9 | Banff: no rejection (minimal multifocal interstitial infiltrates present) Lack of GC formation in secondary lymphoid organs. Unilateral focal lympho-histiocytic inflammation in the lung. No other treatment related changes. |

Animal #5533 that was euthanized on day 31 post-transplant showed tubular dilatation, interstitial infiltrates and fibrosis but only minimal tubulitis. In addition, prominent eosinophilic infiltration in vicinity of the ureter and an abscess next to anastomosis were found. All these findings indicated longstanding poor renal function but rejection could not be confirmed.

C4d immunostaining was negative in all cases.

Lack of germinal center development with or without follicular atrophy was observed in lymphoid organs in all animals. Cecocolitis caused by Balantidium coli infection was diagnosed in animals #5529 and #5533.

No other treatment related changes were encountered.

Transplant Study—Discussion

The goal of the transplant study was to assess, in a non-human primate model of kidney allograft rejection, the beneficial effects of mAb1 when given as combination therapy with sub-therapeutic dose of Cyclosporine A. In addition, it was of relevance to assess the absence of side effects in a model where systemic inflammation is induced.

When applied as combination therapy with a subtherapeutic dose of CsA (20 mg/kg p.o.), mAb1 demonstrated efficacy in increasing the survival of kidney allografts in NHPs. The mean graft survival was >83.6 days and 5 out of 6 animals reached the end of the experimental protocol (established in 91-98 days).

Targeting CD40 using a non-agonist blocking anti-CD40 antibody (mAb1) resulted in prolongation of graft survival in kidney or islet transplanted NHPs. In addition, we could assess a better efficacy and safety by using mAb1 (which is Fc-silent) as compared to Chir12.12 previously reported (fully human monoclonal anti-CD40 antibody of the IgG1/kappa isotype with B cell depleting and co-stimulation blocking properties).

During the whole post-transplant period, there was absence of any relevant clinical pathology events (e.g. minor increase in amylase/lipase levels attributed to typical impaired kidney function after transplant). However, animals #5333, #5523 and #5524 presented reduced kidney function between days 7-19. This period of time is typically characterized by a recovery of SCrea/Surea levels, blood pressure and graft volume in post-transplant animals. In these animals, signs of impaired kidney function were seen such as increased SCrea/SUrea (all 3 animals), transitory increase in graft volume (#5523, #5524) or polydipsia/polyuria (#5523, #5524). One hypothesis could be that those animals developed an early rejection process, which became controlled after 3 weeks of mAb1 treatment. This abnormality in the early post-transplant phase could be due to differences induced by the immunological mode of action of a molecule (Fc-silent) targeting CD40 pathway.

One animal (#5533) was euthanized on day 31 due to acute kidney failure (no rejection). This outcome was caused by an incomplete recovery of the kidney function after the transplantation procedure. The signs indicating poor kidney function were high SUrea levels (11-19 mmol/l) or maintained high SCa concentrations (>2.8 mmol/l). The terminal graft loss was accelerated by a maintained hypertension (>140 mmHg systolic) combined with hypotension observed during anesthesia applied during the biopsy collection procedure and high hypertensive peaks registered the night before euthanasia (~170 mmHg systolic) (Palmer B F (2002) N. Engl. J. Med; 347(16):1256-1261). All those events could not be attributed to mAb1 treatment and only to individual differences in the post-transplant phase.

The high efficacy of the combination therapy could be demonstrated also histologically. Five out of six grafts showed excellent graft quality at the end of the experiment. Lack of germinal center development was observed also in a transplant experiment with Chir12.12. No other treatment related tissue changes were observed.

One of the long-term survivor (#5529) developed cecocolitis caused by Balantidium coli. Although, the infection is common in macaques and often asymptomatic, immunosuppression can lead to an onset of acute disease (Schuster F L, Ramirez-Avila L, (2008) Clin. Microbiol. Rev; 21(4): 626-38). In this animal no clinical signs, such as diarrhea or body weight loss, were observed.

Regarding the B-cell counts monitoring, a partial depletion could be observed with time in all treated animals. This partial depletion is probably not due to active Fc-receptor mediated depletion as mAb1 is a silenced antibody, which does not bind FcR nor mediates in vitro ADCC. The partial depletion can be a mirror of the lack of germinal centers, which is observed in the histology at the end of the experiment. This partial depletion may be due to the lack of survival signals.

In conclusion, the results of the transplant study support the use of mAb1 (and by extension, the other antibodies and proteins of the invention) as valid targets for the treatment of kidney rejection in a combination therapy with an excellent safety profile. The excellent safety profile and efficacy further support the use of the antibodies of the invention in the treatment of autoimmune disorders and/or inflammatory disorders, and prevention of transplant rejection mediated by CD40L-mediated CD40 signaling on cells expressing the CD40 antigen.

SUMMARY

Anti-CD40 antibodies have not been reported to induce hemostatic events in patients, however elevations in pancreatic enzymes in B cell lymphoma patients receiving the anti-CD40 Ab Chir12.12 and the possible risk of pancreatitis precludes the use of this Fc-competent anti-CD40 antibody in chronic autoimmune disease and transplantation for safety reasons. We therefore generated Fc-silent IgG1 anti-CD40 antibodies (mAb1, mAb2, and mAb3) unable to mediate antibody-dependent cellular cytotoxicity (ADCC) or complement-dependent cytotoxicity (CDC) both in vitro and in vivo. mAb1 was able to prolong non-human primate renal allograft survival in combination with sub-therapeutic doses of cyclosporine. In addition, mAb1 was able to completely suppress primary and secondary antibody responses to immunization with a T cell-dependent antigen. Crucially, there was no evidence of hemostatic events or abnormal pancreatic histology in either the transplant or immunization study. Collectively these results suggest mAb1 would be a safe and efficacious therapeutic, and could be used to treat patients suffering from B lymphocyte and antigen presenting cell driven autoimmune disease or undergoing allograft transplant where CD40-CD154 interactions are involved in contributing to pathology.

The invention claimed is:

1. An isolated antibody or antigen-binding portion thereof directed against a target CD40 polypeptide (SEQ ID NO:28), wherein said antibody or antigen-binding portion comprises:
   a. an HCDR1 (SEQ ID NO:1), HCDR2 (SEQ ID NO:2), HCDR3 (SEQ ID NO:3), LCDR1 (SEQ ID NO:4), LCDR2 (SEQ ID NO:5) and LCDR3 (SEQ ID NO:6) and
   b. an IgG1 Fc region comprising an amino acid modification of D265A.

2. The isolated antibody or antigen-binding portion of claim 1, wherein said antibody or antigen-binding portion exhibits <10% specific cell lysis as measured in an ADCC assay.

3. The isolated antibody or antigen-binding portion of claim 2, wherein said antibody or antigen-binding portion exhibits <1% specific cell lysis as measured in an ADCC assay.

4. The isolated antibody or antigen-binding portion of claim 1, wherein said IgG1 Fc region comprises an amino acid sequence of SEQ ID NO: 18.

5. The isolated antibody or antigen-binding portion of claim 4, comprising a heavy chain variable region comprising the amino acid sequence of SEQ ID NO: 7 and light chain variable region comprising the amino acid sequence of SEQ ID NO: 8.

6. A pharmaceutical composition, comprising the antibody or antigen-binding portion according to claim 1, in combination with at least a pharmaceutically acceptable excipient, diluent or carrier.

7. A liquid pharmaceutical formulation comprising the antibody or antigen-binding portion according to claim 1 with at least a buffer.

8. A method of inhibiting CD40L-mediated CD40 signaling in a subject said method comprising administering to said subject the isolated antibody or antigen-binding portion of claim 1, or a pharmaceutical composition thereof.

9. The method of claim 8, wherein the subject has an autoimmune or inflammatory disorder.

10. The method of claim 9, wherein the autoimmune or inflammatory disorder is multiple sclerosis, systemic lupus erythematosus, lupus nephritis, inflammatory bowel disease, Crohn's disease, Sjogren's syndrome, myasthenia gravis, rheumatoid arthritis, atherosclerosis, transplant rejection or graft-versus hose disease.

* * * * *

SEQUENCE LISTING

<160> NUMBER OF SEQ ID NOS: 28

<210> SEQ ID NO 1
<211> LENGTH: 5
<212> TYPE: PRT
<213> ORGANISM: Homo sapiens

<400> SEQUENCE: 1

Ser Tyr Gly Met His
1               5

<210> SEQ ID NO 2
<211> LENGTH: 17
<212> TYPE: PRT
<213> ORGANISM: Homo sapiens

<400> SEQUENCE: 2

Val Ile Ser Tyr Glu Glu Ser Asn Arg Tyr His Ala Asp Ser Val Lys
1               5                   10                  15

Gly

<210> SEQ ID NO 3
<211> LENGTH: 11
<212> TYPE: PRT
<213> ORGANISM: Homo sapiens

<400> SEQUENCE: 3

Asp Gly Gly Ile Ala Ala Pro Gly Pro Asp Tyr
1               5                   10

<210> SEQ ID NO 4
<211> LENGTH: 16
<212> TYPE: PRT
<213> ORGANISM: Homo sapiens

<400> SEQUENCE: 4

Arg Ser Ser Gln Ser Leu Leu Tyr Ser Asn Gly Tyr Asn Tyr Leu Asp
1               5                   10                  15

<210> SEQ ID NO 5
<211> LENGTH: 7
<212> TYPE: PRT
<213> ORGANISM: Homo sapiens

<400> SEQUENCE: 5

Leu Gly Ser Asn Arg Ala Ser
1               5

<210> SEQ ID NO 6
<211> LENGTH: 9
<212> TYPE: PRT
<213> ORGANISM: Homo sapiens

<400> SEQUENCE: 6

Met Gln Ala Arg Gln Thr Pro Phe Thr
1               5

<210> SEQ ID NO 7
<211> LENGTH: 120
<212> TYPE: PRT
<213> ORGANISM: Homo sapiens

<400> SEQUENCE: 7

Gln Val Gln Leu Val Glu Ser Gly Gly Gly Val Val Gln Pro Gly Arg

-continued

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Glu Glu Ser Asn Arg Tyr His Ala Asp Ser Val
    50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
            100                 105                 110

Gly Thr Leu Val Thr Val Ser Ser
        115                 120

<210> SEQ ID NO 8
<211> LENGTH: 112
<212> TYPE: PRT
<213> ORGANISM: Homo sapiens

<400> SEQUENCE: 8

Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Val Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Phe Thr Phe Gly Pro Gly Thr Lys Val Asp Ile Arg
            100                 105                 110

<210> SEQ ID NO 9
<211> LENGTH: 450
<212> TYPE: PRT
<213> ORGANISM: Homo sapiens

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Glu Glu Ser Asn Arg Tyr His Ala Asp Ser Val
    50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln

```
            100                 105                 110
Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 10
<211> LENGTH: 219
<212> TYPE: PRT
<213> ORGANISM: Homo sapiens

<400> SEQUENCE: 10

Asp Ile Val Met Thr Gln Ser Pro Leu Ser Leu Thr Val Thr Pro Gly
1               5                   10                  15
```

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Val Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Phe Thr Phe Gly Pro Gly Thr Lys Val Asp Ile Arg
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 11
<211> LENGTH: 450
<212> TYPE: PRT
<213> ORGANISM: Homo sapiens

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Glu Glu Ser Asn Arg Tyr His Ala Asp Ser Val
    50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Ala Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 12
<211> LENGTH: 219
<212> TYPE: PRT
<213> ORGANISM: Homo sapiens

<400> SEQUENCE: 12

Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Val Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala

```
                    85                  90                  95
Arg Gln Thr Pro Phe Thr Phe Gly Pro Gly Thr Lys Val Asp Ile Arg
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 13
<211> LENGTH: 450
<212> TYPE: PRT
<213> ORGANISM: Homo sapiens

<400> SEQUENCE: 13

Gln Val Gln Leu Val Glu Ser Gly Gly Gly Val Val Gln Pro Gly Arg
1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Glu Glu Ser Asn Arg Tyr His Ala Asp Ser Val
    50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Val Ala Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 14
<211> LENGTH: 219
<212> TYPE: PRT
<213> ORGANISM: Homo sapiens

<400> SEQUENCE: 14

Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Val Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Phe Thr Phe Gly Pro Gly Thr Lys Val Asp Ile Arg
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 15
<211> LENGTH: 450
<212> TYPE: PRT
<213> ORGANISM: Homo sapiens

<400> SEQUENCE: 15

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Glu Glu Ser Asn Arg Tyr His Ala Asp Ser Val
    50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
            305                 310                 315                 320
Glu Tyr Lys Cys Lys Val Ser Asn Lys Ala Leu Pro Ala Pro Ile Glu
                    325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 16
<211> LENGTH: 219
<212> TYPE: PRT
<213> ORGANISM: Homo sapiens

<400> SEQUENCE: 16

Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu Tyr Ser
                20                  25                  30

Asn Gly Tyr Asn Tyr Leu Asp Trp Tyr Leu Gln Lys Pro Gly Gln Ser
            35                  40                  45

Pro Gln Val Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Phe Thr Phe Gly Pro Gly Thr Lys Val Asp Ile Arg
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 17
<211> LENGTH: 217
<212> TYPE: PRT
<213> ORGANISM: Homo sapiens

<400> SEQUENCE: 17

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 18
<211> LENGTH: 217
<212> TYPE: PRT
<213> ORGANISM: Homo sapiens

<400> SEQUENCE: 18

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ala Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110
```

```
Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 19
<211> LENGTH: 217
<212> TYPE: PRT
<213> ORGANISM: Homo sapiens

<400> SEQUENCE: 19

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 20
<211> LENGTH: 1956
<212> TYPE: DNA
<213> ORGANISM: Homo sapiens

<400> SEQUENCE: 20
```

| | |
|---|---|
| caggtgcagt tggtggagtc tgggggaggc gtggtccagc ctgggaggtc cctgagactc | 60 |
| tcctgtgcag cctctggatt caccttcagt agctatggca tgcactgggt ccgccaggct | 120 |
| ccaggcaagg ggctggagtg ggtggcagtt atatcatatg aggaaagtaa tagataccat | 180 |
| gcagactccg tgaagggccg attcaccatc tccagagaca attccaagat cacgctgtat | 240 |
| ctgcaaatga acagcctcag aactgaggac acggctgtgt attactgtgc gagagatggg | 300 |
| ggtatagcag cacctgggcc tgactactgg ggccagggaa ccctggtcac cgtctcctca | 360 |
| gcaagtacca agggcccatc cgtcttcccc ctggcgcccg ctagcaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagag agttggtgag | 660 |
| aggccagcac agggagggag ggtgtctgct ggaagccagg ctcagcgctc ctgcctggac | 720 |
| gcatcccggc tatgcagtcc cagtccaggg cagcaaggca ggccccgtct gcctcttcac | 780 |
| ccggaggcct ctgcccgccc cactcatgct cagggagagg gtcttctggc tttttcccca | 840 |
| ggctctgggc aggcacaggc taggtgcccc taacccaggc cctgcacaca aggggcagg | 900 |
| tgctgggctc agacctgcca agagccatat ccgggaggac cctgcccctg acctaagccc | 960 |
| accccaaagg ccaaactctc cactccctca gctcggacac tttctctcct cccagattcc | 1020 |
| agtaactccc aatcttctct ctgcagagcc caaatcttgt gacaaaactc acacatgccc | 1080 |
| accgtgccca ggtaagccag cccaggcctc gccctccagc tcaaggcggg acaggtgccc | 1140 |
| tagagtagcc tgcatccagg acaggcccc agccgggtgc tgacacgtcc acctccatct | 1200 |
| cttcctcagc acctgaactc ctggggggac cgtcagtctt cctcttcccc ccaaaaccca | 1260 |
| aggacaccct catgatctcc cggacccctg aggtcacatg cgtggtggtg gacgtgagcc | 1320 |
| acgaagaccc tgaggtcaag ttcaactggt acgtggacgg cgtggaggtg cataatgcca | 1380 |
| agacaaagcc gcgggaggag cagtacaaca gcacgtaccg tgtggtcagc gtcctcaccg | 1440 |
| tcctgcacca ggactggctg aatggcaagg agtacaagtg caaggtctcc aacaaagccc | 1500 |
| tcccagcccc catcgagaaa accatctcca aagccaaagg tgggacccgt ggggtgcgag | 1560 |
| ggccacatgg acagaggccg gctcggccca ccctctgccc tgagagtgac cgctgtacca | 1620 |
| acctctgtcc ctacagggca gccccgagaa ccacaggtgt acaccctgcc cccatcccgg | 1680 |
| gaggagatga ccaagaacca ggtcagcctg acctgcctgg tcaaaggctt ctatcccagc | 1740 |
| gacatcgccg tggagtggga gagcaatggg cagccggaga caactacaa gaccacgcct | 1800 |
| cccgtgctgg actccgacgg ctccttcttc ctctatagca agctcaccgt ggacaagagc | 1860 |
| aggtggcagc aggggaacgt cttctcatgc tccgtgatgc atgaggctct gcacaaccac | 1920 |
| tacacgcaga agagcctctc cctgtctccg ggtaaa | 1956 |

<210> SEQ ID NO 21
<211> LENGTH: 657
<212> TYPE: DNA
<213> ORGANISM: Homo sapiens

<400> SEQUENCE: 21

| | |
|---|---|
| gatattgtga tgactcagtc tccactctcc ctgaccgtca cccctggaga gccggcctcc | 60 |
| atctcctgca ggtccagtca gagcctcctg tatagtaatg gatacaacta tttggattgg | 120 |
| tacctgcaga agccagggca gtctccacag gtcctgatct cttgtgggttc taatcgggcc | 180 |

```
tccggggtcc ctgacaggtt cagtggcagt ggatcaggca cagattttac actgaaaatc      240
agcagagtgg aggctgagga tgttggggtt tattactgca tgcaagctcg acaaactcca      300
ttcactttcg gccctgggac caaagtggat atcagacgaa ctgtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgt      657
```

<210> SEQ ID NO 22
<211> LENGTH: 1350
<212> TYPE: DNA
<213> ORGANISM: Homo sapiens

<400> SEQUENCE: 22

```
caggtgcagc tggtggaatc tggcggcgga gtggtgcagc ctggccggtc cctgagactg       60
tcttgcgccg cctccggctt caccttctcc agctacggca tgcactgggt gcgacaggcc      120
cctggcaagg gactggaatg ggtggccgtg atctcctacg aggaatccaa cagataccac      180
gctgactccg tgaagggccg gttcacaatc tcccgggaca actccaagat caccctgtac      240
ctgcagatga actccctgcg gaccgaggac accgccgtgt actactgcgc cagggacgga      300
ggaatcgccg ctcctggacc tgattattgg ggccagggca ccctggtgac agtgtcctcc      360
gctagcacca agggcccctc cgtgttccct ctggccccct ccagcaagtc cacctctggc      420
ggcaccgccg ctctgggctg cctggtgaaa gactacttcc ccgagcccgt gaccgtgtcc      480
tggaactctg gcgccctgac ctccggcgtg cacacctttc cagccgtgct gcagtcctcc      540
ggcctgtact ccctgtcctc cgtggtgacc gtgccctcta gctctctggg cacccagacc      600
tacatctgca acgtgaacca caagccctcc aacaccaagg tggacaagcg ggtggaaccc      660
aagtcctgcg acaagaccca cacctgtccc ccctgccctg ccctgaact gctgggcgga       720 ccttccgtgt tcctgttccc cccaaagccc aaggacaccc tgatgatctc ccggacccc      780 gaagtgacct gcgtggtggt ggacgtgtcc cacgaggacc ctgaagtgaa gttcaattgg      840
tacgtggacg gcgtggaagt gcacaacgcc aagaccaagc cagagagga cagtacgcc      900 tccacctacc gggtggtgtc tgtgctgacc gtgctgcacc aggactggct gaacggcaaa      960
gagtacaagt gcaaggtctc caacaaggcc ctgcctgccc catcgaaaa gaccatctcc     1020 aaggccaagg gccagccccg cgagccacag gtgtacacac tgcccccag ccgggaagag     1080 atgaccaaga accaggtgtc cctgacctgt ctggtcaaag cttctaccc ctccgatatc     1140 gccgtggagt gggagtccaa cggacagccc gagaacaact acaagaccac cccccctgtg     1200
ctggactccg acggctcatt cttcctgtac tccaagctga ccgtggacaa gtcccggtgg     1260
cagcagggca acgtgttctc ctgctccgtg atgcacgagg ccctgcacaa ccactacacc     1320
cagaagtccc tgtccctgag ccccggcaag                                     1350
```

<210> SEQ ID NO 23
<211> LENGTH: 657
<212> TYPE: DNA
<213> ORGANISM: Homo sapiens

<400> SEQUENCE: 23

```
gacatcgtga tgacccagtc cccctgtcc ctgaccgtga cacctggcga gcctgcctct     60
atctcctgca gatcctccca gtccctgctg tactccaacg gctacaacta cctggactgg    120
tatctgcaga agcccggcca gtccccacag gtgctgatct ccctgggctc aacagagcc    180 tctggcgtgc ccgaccggtt ctccggctct ggctctggca ccgacttcac actgaagatc    240
tcacgggtgg aagccgagga cgtgggcgtg tactactgca tgcaggcccg gcagacccc    300 ttcaccttcg gccctggcac caaggtggac atcggcgta cggtggccgc tcccagcgtg    360
ttcatcttcc ccccagcga cgagcagctg aagagcggca ccgccagcgt ggtgtgcctg    420
ctgaacaact tctacccccg ggaggccaag gtgcagtgga aggtggacaa cgccctgcag    480
agcggcaaca gccaggagag cgtcaccgag caggacagca aggactccac ctacagcctg    540
agcagcaccc tgaccctgag caaggccgac tacgagaagc ataaggtgta cgcctgcgag    600
gtgacccacc agggcctgtc cagccccgtg accaagagct caacagggg cgagtgc       657
```

`<210>` SEQ ID NO 24
`<211>` LENGTH: 1350
`<212>` TYPE: DNA
`<213>` ORGANISM: Homo sapiens

`<400>` SEQUENCE: 24

```
caggtgcagc tggtggaatc tggcggcgga gtggtgcagc ctggccggtc cctgagactg     60
tcttgcgccg cctccggctt caccttctcc agctacggca tgcactgggt gcgacaggcc    120
cctggcaagg gactggaatg ggtggccgtg atctcctacg aggaatccaa cagataccac    180
gctgactccg tgaagggccg gttcacaatc tcccgggaca ctccaagat caccctgtac    240 ctgcagatga actccctgcg gaccgaggac accgccgtgt actactgcgc cagggacgga    300
ggaatcgccg ctcctggacc tgattattgg ggccagggca ccctggtgac agtgtcctcc    360
gctagcacca agggcccctc cgtgttccct ctggcccct ccagcaagtc cacctctggc    420
ggcaccgccg ctctgggctg cctggtgaaa gactacttcc ccgagccgt gaccgtgtcc    480 tggaactctg gcgccctgac ctccggcgtg cacacctttc cagccgtgct gcagtcctcc    540
ggcctgtact ccctgtcctc cgtggtgacc gtgccctcta gctctctggg cacccagacc    600
tacatctgca acgtgaacca caagccctcc aacaccaagg tggacaagcg ggtggaaccc    660
aagtcctgcg acaagaccca cacctgtccc cctgccctg cctgaact gctgggcgga    720 ccttccgtgt tcctgttccc cccaaagccc aaggacaccc tgatgatctc ccggacccc    780 gaagtgacct gcgtggtggt ggccgtgtcc acgaggacc ctgaagtgaa gttcaattgg    840
tacgtggacg gcgtggaagt gcacaacgcc aagaccaagc ccagagagga acagtacaac    900
tccacctacc gggtggtgtc tgtgctgacc gtgctgcacc aggactggct gaacggcaaa    960
gagtacaagt gcaaggtctc caacaaggcc ctgcctgccc ccatcgaaaa gaccatctcc   1020
aaggccaagg gccagccccg cgagccacag gtgtacacac tgcccccag ccgggaagag   1080 atgaccaaga accaggtgtc cctgacctgt ctggtcaaag cttctaccc ctccgatatc   1140 gccgtggagt gggagtccaa cggacagccc gagaacaact acaagaccac ccccctgtg   1200 ctggactccg acggctcatt cttcctgtac tccaagctga ccgtggacaa gtcccggtgg   1260
cagcagggca acgtgttctc ctgctccgtg atgcacgagg ccctgcacaa ccactacacc   1320
cagaagtccc tgtccctgag ccccggcaag                                     1350
```

`<210>` SEQ ID NO 25
`<211>` LENGTH: 657

```
<212> TYPE: DNA
<213> ORGANISM: Homo sapiens

<400> SEQUENCE: 25
gacatcgtga tgacccagtc ccccctgtcc ctgaccgtga cacctggcga gcctgcctct    60
atctcctgca gatcctccca gtccctgctg tactccaacg gctacaacta cctggactgg   120
tatctgcaga agcccggcca gtccccacag gtgctgatct ccctgggctc aacagagcc    180
tctggcgtgc ccgaccggtt ctccggctct ggctctggca ccgacttcac actgaagatc   240
tcacgggtgg aagccgagga cgtgggcgtg tactactgca tgcaggcccg gcagaccccc   300
ttcaccttcg gccctggcac caaggtggac atccggcgta cggtggccgc tcccagcgtg   360
ttcatcttcc ccccagcga cgagcagctg aagagcggca ccgccagcgt ggtgtgcctg    420
ctgaacaact tctaccccg ggaggccaag gtgcagtgga aggtggacaa cgccctgcag    480
agcggcaaca gccaggagag cgtcaccgag caggacagca aggactccac ctacagcctg   540
agcagcaccc tgaccctgag caaggccgac tacgagaagc ataaggtgta cgcctgcgag   600
gtgacccacc agggcctgtc cagccccgtg accaagagct caacagggg cgagtgc       657

<210> SEQ ID NO 26
<211> LENGTH: 1350
<212> TYPE: DNA
<213> ORGANISM: Homo sapiens

<400> SEQUENCE: 26
caggtgcagc tggtggaatc tggcggcgga gtggtgcagc ctggccggtc cctgagactg    60
tcttgcgccg cctccggctt caccttctcc agctacggca tgcactgggt gcgacaggcc   120
cctggcaagg gactgaatg ggtggccgtg atctcctacg aggaatccaa cagataccac   180
gctgactccg tgaagggccg gttcacaatc tccgggaca actccaagat caccctgtac   240
ctgcagatga actccctgcg gaccgaggac accgccgtgt actactgcgc cagggacgga   300
ggaatcgccg ctcctggacc tgattattgg ggccagggca cctggtgac agtgtcctcc   360
gctagcacca agggccctc cgtgttccct ctggcccctt ccagcaagtc tacctccggc   420
ggcacagctg ctctgggctg cctggtcaag gactacttcc ctgagcctgt gacagtgtcc   480
tggaactctg gcgccctgac ctctggcgtg cacaccttcc ctgccgtgct gcagtcctcc   540
ggcctgtact ccctgtcctc cgtggtcaca gtgccttcaa gcagcctggg cacccagacc   600
tatatctgca acgtgaacca caagccttcc aacaccaagg tggacaagcg ggtggagcct   660
aagtcctgcg acaagaccca cacctgtcct ccctgccctg ctcctgaagc tgctggcggc   720
ccttctgtgt tcctgttccc tccaaagccc aaggacaccc tgatgatctc ccggacccct   780
gaagtgacct gcgtggtggt ggacgtgtcc cacgaggatc ctgaagtgaa gttcaattgg   840
tacgtggacg gcgtggaggt gcacaacgcc aagaccaagc ctcgggagga acagtacaac   900
tccacctacc gggtggtgtc cgtgctgacc gtgctgcacc aggactggct gaacggcaaa   960
gagtacaagt gcaaagtctc caacaaggcc ctgcctgccc ctatcgaaaa gacaatctcc  1020
aaggccaagg gccagcctag ggaaccccag gtgtacaccc tgcccccag ccgggaggaa   1080
atgaccaaga accaggtgtc cctgacctgt ctggtcaagg gcttctaccc ttccgatatc  1140
gccgtggagt gggagtctaa cggccagcct gagaacaact acaagaccac ccctcctgtg  1200
ctggactccg acggctcctt cttcctgtac tccaaactga ccgtggacaa gtcccggtgg  1260
cagcagggca acgtgttctc ctgctccgtg atgcacgagg ccctgcacaa ccactacacc  1320
```

```
cagaagtccc tgtccctgtc tcccggcaag                                    1350
```

<210> SEQ ID NO 27
<211> LENGTH: 657
<212> TYPE: DNA
<213> ORGANISM: Homo sapiens

<400> SEQUENCE: 27

```
gacatcgtga tgacccagtc cccctgtcc ctgaccgtga cacctggcga gcctgcctct      60
atctcctgca gatcctccca gtccctgctg tactccaacg gctacaacta cctggactgg    120
tatctgcaga agcccggcca gtccccacag gtgctgatct ccctgggctc aacagagcc     180
tctggcgtgc ccgaccggtt ctccggctct ggctctggca ccgacttcac actgaagatc    240
tcacgggtgg aagccgagga cgtgggcgtg tactactgca tgcaggcccg gcagaccccc    300
ttcaccttcg gccctggcac caaggtggac atccggcgta cggtggccgc tcccagcgtg    360
ttcatcttcc ccccagcga cgagcagctg aagagcggca ccgccagcgt ggtgtgcctg    420
ctgaacaact tctaccccg ggaggccaag gtgcagtgga aggtggacaa cgccctgcag    480
agcggcaaca gccaggagag cgtcaccgag caggacagca aggactccac ctacagcctg    540
agcagcaccc tgaccctgag caaggccgac tacgagaagc ataaggtgta cgcctgcgag    600
gtgacccacc agggcctgtc cagccccgtg accaagagct tcaacagggg cgagtgc      657
```

<210> SEQ ID NO 28
<211> LENGTH: 277
<212> TYPE: PRT
<213> ORGANISM: Homo sapiens

<400> SEQUENCE: 28

```
Met Val Arg Leu Pro Leu Gln Cys Val Leu Trp Gly Cys Leu Leu Thr
 1               5                  10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205
```

-continued

```
Leu Leu Val Leu Val Phe Ile Lys Lys Val Ala Lys Lys Pro Thr Asn
    210             215             220

Lys Ala Pro His Pro Lys Gln Glu Pro Gln Glu Ile Asn Phe Pro Asp
225             230             235             240

Asp Leu Pro Gly Ser Asn Thr Ala Ala Pro Val Gln Glu Thr Leu His
            245             250             255

Gly Cys Gln Pro Val Thr Gln Glu Asp Gly Lys Glu Ser Arg Ile Ser
            260             265             270

Val Gln Glu Arg Gln
            275
```